(12) United States Patent
Zachar

(10) Patent No.: US 10,946,153 B2
(45) Date of Patent: Mar. 16, 2021

(54) MECHANICAL USER CONTROL ELEMENTS FOR FLUID INPUT MODULE

(71) Applicant: TELEFLEX LIFE SCIENCES PTE. LTD., Singapore (SG)

(72) Inventor: Oron Zachar, Tel Aviv (IL)

(73) Assignee: TELEFLEX LIFE SCIENCES PTE. LTD., Singapore (SG)

( * ) Notice: Subject to any disclaimer, the term of this patent is extended or adjusted under 35 U.S.C. 154(b) by 794 days.

(21) Appl. No.: 15/595,250

(22) Filed: May 15, 2017

(65) Prior Publication Data

US 2017/0326317 A1   Nov. 16, 2017

Related U.S. Application Data

(60) Provisional application No. 62/336,894, filed on May 16, 2016.

(51) Int. Cl.
*A61M 16/04* (2006.01)
*A61M 1/00* (2006.01)

(52) U.S. Cl.
CPC ...... *A61M 16/0463* (2013.01); *A61M 1/0084* (2013.01); *A61M 16/044* (2013.01);
(Continued)

(58) Field of Classification Search
CPC ............ A61M 16/0463; A61M 16/044; A61M 1/0035; A61M 1/0064; A61M 1/0058;
(Continued)

(56) References Cited

U.S. PATENT DOCUMENTS 3,211,150 A   10/1965   John
3,502,069 A   3/1970    Silverman
(Continued)

FOREIGN PATENT DOCUMENTS

EP   0 692 273       4/2004
EP   1239907 B1     9/2007
(Continued)

OTHER PUBLICATIONS

An International Search Report dated Oct. 16, 2012, which issued during the prosecution of Applicant's PCT/IB2012/051532.
(Continued)

*Primary Examiner* — Colin W Stuart
*Assistant Examiner* — Douglas Y Sul
(74) *Attorney, Agent, or Firm* — BakerHostetler

(57) ABSTRACT

A cleaning catheter includes an inflatable element and an input module, which includes an inflation chamber coupled in fluid communication with the inflatable element. A flow regulator defines a suction port coupleable in fluid communication with a suction source. A mechanical suction-control button is configured to assume at least first and second spatial positions. A mechanical inflation-control button is configured to mechanically and non-electrically increase pressure in the interior of the inflation chamber during a transition of the mechanical inflation-control button from a first spatial position to a second spatial position; and a reversibly-engageable linking element, which is moveable with respect to the mechanical suction-control button and the mechanical inflation-control button, and is configured to assume at least a first spatial position, in which the linking element does not engage the mechanical suction-control button when the mechanical suction-control button is in its second spatial position; and a second spatial position.

23 Claims, 23 Drawing Sheets

(52) U.S. Cl.
CPC ......... *A61M 1/0039* (2013.01); *A61M 1/0064* (2013.01); *A61M 2209/10* (2013.01)

(58) Field of Classification Search
CPC ............ A61M 1/0039; A61M 2209/10; A61M 2025/0019; Y10T 137/87169–87241; Y10T 137/85994; Y10T 137/86099
USPC ........................................ 137/565.12, 565.25
See application file for complete search history.

(56) References Cited

U.S. PATENT DOCUMENTS

| | | | |
|---|---|---|---|
| 3,671,979 A | 6/1972 | Moulopoulos | |
| 3,780,736 A | 12/1973 | Chen | |
| 3,985,141 A | 10/1976 | Stanley et al. | |
| 4,016,885 A | 4/1977 | Bruner | |
| 4,064,882 A | 12/1977 | Johnson et al. | |
| 4,088,135 A | 5/1978 | O'Neill | |
| 4,134,407 A | 1/1979 | Elam | |
| 4,159,722 A | 7/1979 | Walker | |
| 4,166,468 A | 9/1979 | Haynie | |
| 4,182,344 A | 1/1980 | Benson | |
| 4,240,433 A | 12/1980 | Bordow | |
| 4,245,639 A | 1/1981 | La Rosa | |
| 4,324,262 A | 4/1982 | Hall | |
| 4,351,328 A | 9/1982 | Bodai | |
| 4,469,100 A | 9/1984 | Hardwick | |
| 4,501,273 A | 2/1985 | McGinnis | |
| 4,510,933 A | 4/1985 | Wendt et al. | |
| 4,555,242 A | 11/1985 | Saudagar | |
| 4,569,344 A | 2/1986 | Palmer | |
| 4,606,347 A | 8/1986 | Fogarty et al. | |
| 4,607,635 A | 8/1986 | Heyden | |
| 4,630,606 A | 12/1986 | Weerda et al. | |
| 4,638,539 A | 1/1987 | Palmer | |
| 4,649,914 A | 3/1987 | Kowalewski | |
| 4,691,702 A | 9/1987 | Chantzis | |
| 4,758,223 A | 7/1988 | Rydell | |
| 4,762,125 A | 8/1988 | Leiman et al. | |
| 4,805,611 A | 2/1989 | Hodgkins | |
| 4,813,935 A | 3/1989 | Haber et al. | |
| 4,850,982 A | 7/1989 | Erlich et al. | |
| 4,886,496 A | 12/1989 | Conoscenti et al. | |
| 4,932,959 A | 6/1990 | Horzewski et al. | |
| 4,946,440 A | 8/1990 | Hall | |
| 4,961,738 A | 10/1990 | Mackin | |
| 5,003,657 A | 4/1991 | Boiteau | |
| 5,029,580 A | 7/1991 | Radford et al. | |
| 5,067,497 A | 11/1991 | Greear | |
| 5,073,164 A | 12/1991 | Hollister et al. | |
| 5,101,817 A | 4/1992 | Etter | |
| 5,125,893 A | 6/1992 | Dryden | |
| 5,134,996 A | 8/1992 | Bell | |
| 5,139,018 A | 8/1992 | Brodsky et al. | |
| 5,181,908 A | 1/1993 | Bell | |
| 5,188,618 A | 2/1993 | Thomas | |
| 5,215,522 A | 6/1993 | Page et al. | |
| 5,218,970 A | 6/1993 | Turnbull et al. | |
| 5,254,098 A | 10/1993 | Ulrich et al. | |
| 5,269,756 A | 12/1993 | Dryden | |
| 5,277,177 A | 1/1994 | Page et al. | |
| 5,279,549 A | 1/1994 | Ranford | |
| 5,309,902 A | 5/1994 | Kee et al. | |
| 5,325,851 A | 7/1994 | Reynolds et al. | |
| 5,336,172 A | 8/1994 | Bales et al. | |
| 5,337,730 A | 8/1994 | Maguire | |
| 5,349,950 A | 9/1994 | Ulrich et al. | |
| 5,360,403 A | 11/1994 | Mische | |
| 5,361,753 A | 11/1994 | Pothmann et al. | |
| 5,364,345 A | 11/1994 | Lowery et al. | |
| 5,364,358 A | 11/1994 | Hewitt et al. | |
| 5,460,613 A | 10/1995 | Ulrich et al. | |
| 5,487,383 A | 1/1996 | Levinson | |
| 5,490,503 A | 2/1996 | Hollister | |
| 5,545,179 A | 8/1996 | Williamson, IV | |
| 5,582,161 A | 12/1996 | Kee | |
| 5,611,336 A | 3/1997 | Page et al. | |
| 5,634,937 A | 6/1997 | Mollenauer et al. | |
| 5,694,922 A | 12/1997 | Palmer | |
| 5,709,691 A | 1/1998 | Morejon | |
| 5,715,815 A | 2/1998 | Lorenzen et al. | |
| 5,725,478 A | 3/1998 | Saad | |
| 5,730,123 A | 3/1998 | Lorenzen et al. | |
| 5,738,091 A | 4/1998 | Kee | |
| 5,743,258 A | 4/1998 | Sato et al. | |
| 5,775,325 A | 7/1998 | Russo | |
| 5,779,687 A | 7/1998 | Bell et al. | |
| 5,832,920 A | 11/1998 | Field | |
| 5,897,567 A * | 4/1999 | Ressemann | A61B 17/32 604/22 |
| 6,045,531 A | 4/2000 | Davis | |
| 6,082,361 A | 7/2000 | Morejon | |
| 6,227,200 B1 | 5/2001 | Crump | |
| 6,270,489 B1 | 8/2001 | Wise et al. | |
| 6,318,368 B1 | 11/2001 | Morejon | |
| 6,494,208 B1 | 12/2002 | Morejon | |
| 6,602,219 B2 | 8/2003 | Madsen | |
| 6,612,304 B1 | 9/2003 | Cise | |
| 6,647,984 B1 | 11/2003 | O'Dea | |
| 6,679,262 B1 | 1/2004 | Morejon | |
| 6,679,834 B2 | 1/2004 | Stahl et al. | |
| 6,805,125 B1 | 10/2004 | Crump | |
| 6,918,893 B2 | 7/2005 | Houde et al. | |
| 6,923,184 B1 | 8/2005 | Russo | |
| 6,932,788 B2 | 8/2005 | Kamiyama et al. | |
| 6,935,339 B2 | 8/2005 | Neto | |
| 6,976,974 B2 | 12/2005 | Houde et al. | |
| 7,021,313 B1 | 4/2006 | Crump et al. | |
| 7,040,322 B2 | 5/2006 | Fortuna | |
| 7,051,737 B2 | 5/2006 | Kolobow | |
| 7,060,135 B2 | 6/2006 | Morejon | |
| 7,156,827 B2 | 1/2007 | McNary et al. | |
| 7,172,572 B2 | 2/2007 | Diamond et al. | |
| 7,179,272 B2 | 2/2007 | Kieturakis et al. | |
| 7,188,623 B2 | 3/2007 | Anderson et al. | |
| 7,191,782 B2 | 3/2007 | Madsen | |
| 7,204,252 B2 | 4/2007 | Johnson | |
| 7,273,473 B2 | 9/2007 | Owens et al. | |
| 7,278,429 B2 | 10/2007 | Johnson | |
| 7,383,736 B2 | 6/2008 | Esnouf | |
| 7,478,636 B2 | 1/2009 | Madsen et al. | |
| 7,556,041 B2 | 7/2009 | Madsen | |
| 7,625,207 B2 | 12/2009 | Hershey | |
| 7,669,600 B2 | 3/2010 | Morejon | |
| 7,717,116 B2 | 5/2010 | Mijers | |
| 7,726,315 B2 | 6/2010 | Field | |
| 7,775,206 B2 | 8/2010 | Anderson et al. | |
| 7,789,893 B2 | 9/2010 | Drasler et al. | |
| 7,819,890 B2 | 10/2010 | Russo et al. | |
| 7,854,728 B2 | 12/2010 | Boyle, Jr. | |
| 7,878,202 B2 | 2/2011 | Anderson et al. | |
| 7,967,811 B2 | 6/2011 | Kumar | |
| 8,002,732 B2 | 8/2011 | Visconti | |
| 8,133,326 B2 | 3/2012 | Bracken | |
| 8,157,919 B2 | 4/2012 | Vazales et al. | |
| 8,210,168 B2 | 7/2012 | Swisher | |
| 8,215,306 B2 | 7/2012 | Brewer et al. | |
| RE43,886 E | 1/2013 | Mijers | |
| 8,381,345 B2 | 2/2013 | Vazales et al. | |
| 8,382,908 B2 | 2/2013 | Vazales et al. | |
| 8,397,577 B2 | 3/2013 | Slocum, Sr. et al. | |
| 8,414,544 B2 | 4/2013 | Resca | |
| 8,434,488 B2 | 5/2013 | Li et al. | |
| 8,458,844 B2 | 6/2013 | Vazales et al. | |
| 8,468,637 B2 | 6/2013 | Vazales et al. | |
| 8,486,100 B2 | 7/2013 | Oishi et al. | |
| 8,534,287 B2 | 9/2013 | Vazales et al. | |
| 8,556,851 B2 | 10/2013 | Hirszowicz et al. | |
| 8,557,054 B2 | 10/2013 | Morejon | |
| 8,601,633 B2 | 12/2013 | Vazales et al. | |
| 8,631,798 B2 | 1/2014 | Varga et al. | |
| 8,783,255 B2 | 7/2014 | Maguire et al. | |
| 8,888,739 B2 | 11/2014 | Gregory et al. | |
| 8,999,074 B2 | 4/2015 | Zachar et al. | |

(56) References Cited

U.S. PATENT DOCUMENTS

| | | |
|---|---|---|
| 9,010,322 B2 | 4/2015 | Swisher |
| 9,095,286 B2 | 8/2015 | Vazales et al. |
| 9,119,926 B2 | 9/2015 | Cuevas et al. |
| 9,131,988 B2 | 9/2015 | Bagwell et al. |
| 9,220,859 B2 | 12/2015 | Li et al. |
| 9,248,249 B2 | 2/2016 | Li et al. |
| 9,332,891 B2 | 5/2016 | Vazales et al. |
| 9,352,112 B2 | 5/2016 | Sederstrom et al. |
| 9,386,907 B2 | 7/2016 | Vazales et al. |
| 9,398,837 B2 | 7/2016 | Vazales et al. |
| 9,480,537 B2 | 11/2016 | Stadelman et al. |
| 2003/0145860 A1 | 8/2003 | Johnson |
| 2003/0188749 A1 | 10/2003 | Nichols et al. |
| 2003/0209258 A1 | 11/2003 | Morejon |
| 2003/0216698 A1 | 11/2003 | McNary et al. |
| 2004/0082923 A1 | 4/2004 | Field |
| 2004/0221851 A1 | 11/2004 | Madsen |
| 2004/0221852 A1 | 11/2004 | Madsen |
| 2005/0172971 A1 | 8/2005 | Kolobow |
| 2005/0279359 A1 | 12/2005 | LeBlanc et al. |
| 2006/0005841 A1 | 1/2006 | Anderson et al. |
| 2006/0099434 A1 | 5/2006 | Hoetger |
| 2006/0130847 A1 | 6/2006 | Morejon |
| 2006/0150981 A1 | 7/2006 | Johnson |
| 2006/0207605 A1 | 9/2006 | Anderson et al. |
| 2006/0278235 A1 | 12/2006 | White et al. |
| 2007/0021651 A1 | 1/2007 | Gobel |
| 2007/0028924 A1 | 2/2007 | Madsen et al. |
| 2007/0038226 A1 | 2/2007 | Galdonik |
| 2007/0089748 A1 | 4/2007 | Madsen et al. |
| 2007/0163599 A1 | 7/2007 | Mijers |
| 2007/0282250 A1 | 12/2007 | Anderson et al. |
| 2008/0011304 A1 | 1/2008 | Stewart |
| 2008/0035154 A1 | 2/2008 | Johnson |
| 2008/0047562 A1 | 2/2008 | Colburn et al. |
| 2008/0066746 A1 | 3/2008 | Nelson et al. |
| 2008/0078403 A1 | 4/2008 | Clayton |
| 2008/0114338 A1 | 5/2008 | Kumar |
| 2008/0121236 A1 | 5/2008 | Field |
| 2008/0167606 A1 | 7/2008 | Dann et al. |
| 2008/0200759 A1 | 8/2008 | Niwa et al. |
| 2008/0210235 A1 | 9/2008 | Field et al. |
| 2009/0178681 A1 | 7/2009 | Bracken |
| 2009/0260632 A1 | 10/2009 | Abnousi et al. |
| 2009/0281483 A1 | 11/2009 | Baker et al. |
| 2009/0287151 A1 | 11/2009 | Resca |
| 2009/0306545 A1 | 12/2009 | Elsakka et al. |
| 2010/0010431 A1 | 1/2010 | Tulley |
| 2010/0036410 A1 | 2/2010 | Krolik et al. |
| 2010/0081896 A1 | 4/2010 | Swisher |
| 2010/0106102 A1 | 4/2010 | Ziebol et al. |
| 2010/0113916 A1 | 5/2010 | Kumar |
| 2010/0137899 A1 | 6/2010 | Razack |
| 2010/0147309 A1 | 6/2010 | Cuevas et al. |
| 2010/0147310 A1 | 6/2010 | Brewer et al. |
| 2010/0147312 A1 | 6/2010 | Brewer et al. |
| 2010/0170517 A1 | 7/2010 | Hackner |
| 2010/0186748 A1 | 7/2010 | Morejon |
| 2010/0199448 A1 | 8/2010 | Vazales et al. |
| 2010/0199999 A1 | 8/2010 | Vazales |
| 2010/0307507 A1 | 12/2010 | Li et al. |
| 2010/0307508 A1 | 12/2010 | Li et al. |
| 2010/0318094 A1 | 12/2010 | Oishi et al. |
| 2011/0023884 A1 | 2/2011 | Cuevas et al. |
| 2011/0023885 A1 | 2/2011 | Vazales et al. |
| 2011/0023886 A1 | 2/2011 | Vazales et al. |
| 2011/0023887 A1 | 2/2011 | Vazales et al. |
| 2011/0023888 A1 | 2/2011 | Vazales et al. |
| 2011/0180072 A1 | 7/2011 | Morejon |
| 2011/0186052 A1 | 8/2011 | Morejon |
| 2011/0197894 A1 | 8/2011 | Morejon |
| 2011/0253145 A1 | 10/2011 | Calderoni et al. |
| 2012/0024293 A1 | 2/2012 | Maguire et al. |
| 2012/0090619 A1 | 4/2012 | Levine |
| 2012/0180791 A1 | 7/2012 | Ciccone |
| 2012/0204884 A1 | 8/2012 | Howard |
| 2012/0247479 A1 | 10/2012 | Varga et al. |
| 2012/0289893 A1 | 11/2012 | Chung |
| 2012/0296283 A1 | 11/2012 | Swisher |
| 2013/0014756 A1 | 1/2013 | Young et al. |
| 2013/0023729 A1 | 1/2013 | Vazales et al. |
| 2013/0030249 A1 | 1/2013 | Vazales et al. |
| 2013/0035628 A1 | 2/2013 | Garrison et al. |
| 2013/0046332 A1 | 2/2013 | Jones et al. |
| 2013/0112207 A1 | 5/2013 | Roth |
| 2013/0146063 A1 | 6/2013 | Sederstrom et al. |
| 2013/0218071 A1 | 8/2013 | Resca |
| 2013/0228196 A1 | 9/2013 | Vazales et al. |
| 2013/0245665 A1 | 9/2013 | Scandurra et al. |
| 2014/0012074 A1 | 1/2014 | Vazales et al. |
| 2014/0020682 A1 | 1/2014 | Li et al. |
| 2014/0033455 A1 | 2/2014 | Vazales et al. |
| 2014/0090194 A1 | 4/2014 | Stadelman et al. |
| 2014/0090195 A1 | 4/2014 | Stadelman et al. |
| 2014/0090642 A1 | 4/2014 | Bagwell et al. |
| 2014/0142496 A1* | 5/2014 | Zachar ............... A61M 1/0064 604/28 |
| 2014/0150782 A1* | 6/2014 | Vazales ............. A61M 16/0434 128/202.16 |
| 2014/0196721 A1 | 7/2014 | Gilhuly |
| 2014/0207056 A1* | 7/2014 | Bono ................. A61M 1/0064 604/34 |
| 2014/0246015 A1* | 9/2014 | Einav ................ A61M 16/0486 128/202.16 |
| 2014/0283875 A1 | 9/2014 | Vazales et al. |
| 2014/0290649 A1 | 10/2014 | Maguire et al. |
| 2015/0133864 A1 | 5/2015 | Zachar et al. |
| 2015/0190597 A1 | 7/2015 | Zachar et al. |
| 2015/0209536 A1 | 7/2015 | Roth |
| 2015/0335842 A1 | 11/2015 | Cuevas et al. |
| 2015/0343182 A1 | 12/2015 | Vazales et al. |
| 2016/0082212 A1 | 3/2016 | Li et al. |
| 2016/0121066 A1 | 5/2016 | Zachar et al. |
| 2016/0193011 A1 | 7/2016 | Vazales et al. |
| 2016/0193439 A1 | 7/2016 | Zachar et al. |
| 2016/0199608 A1 | 7/2016 | Morejon |
| 2016/0250431 A1 | 9/2016 | Sederstrom et al. |
| 2016/0287834 A1 | 10/2016 | Bennett |
| 2017/0106160 A1 | 4/2017 | Zachar |
| 2017/0189589 A1 | 7/2017 | Zachar et al. |
| 2017/0326317 A1 | 11/2017 | Zachar |

FOREIGN PATENT DOCUMENTS

| | | |
|---|---|---|
| EP | 2928517 A1 | 10/2015 |
| GB | 2 482 618 A | 2/2012 |
| GB | 2 482 618 B | 7/2012 |
| JP | S63-270064 | 11/1988 |
| JP | 2009504240 | 2/2009 |
| WO | 89/07466 | 8/1989 |
| WO | 94/03226 | 2/1994 |
| WO | 99/38548 | 8/1999 |
| WO | 2003/101516 | 12/2003 |
| WO | 2006/099434 | 9/2006 |
| WO | 2007/024288 | 3/2007 |
| WO | 2007/141787 | 12/2007 |
| WO | 2007/146613 | 12/2007 |
| WO | 2010/091309 | 8/2010 |
| WO | 2011/020985 | 2/2011 |
| WO | 2011/094517 | 8/2011 |
| WO | 2011/126812 | 10/2011 |
| WO | 2012087837 A1 | 6/2012 |
| WO | 2012/131626 | 10/2012 |
| WO | 2013/030821 | 3/2013 |
| WO | 2014/089028 | 6/2014 |
| WO | 2015/143388 | 9/2015 |
| WO | 2015/187583 | 12/2015 |

(56) References Cited

FOREIGN PATENT DOCUMENTS

| WO | 2017118970 A1 | 7/2017 |
|---|---|---|
| WO | 2017199248 A1 | 11/2017 |

OTHER PUBLICATIONS

Examination Report dated Nov. 3, 2011 which issued during the prosecution of GB Patent Application No. 1116735.0.

Search Report dated Nov. 2, 2011 which issued during the prosecution of GB Patent Application No. 2482618.

Novelty Search Report dated Sep. 16, 2011 which issued during the prosecution of Swedish Patent Application No. 179871.

An Office Action dated Jul. 21, 2015, which issued during the prosecution of U.S. Appl. No. 14/596,905.

U.S. Appl. No. 62/319,640, filed Apr. 7, 2016.

An Office Action dated Jun. 11, 2014, which issued during the prosecution of U.S. Appl. No. 13/806,958.

U.S. Appl. No. 62/287,223, filed Jan. 26, 2016.

An Office Action dated Nov. 10, 2014, which issued during the prosecution of U.S. Appl. No. 13/806,958.

U.S. Appl. No. 61/527,658, filed Aug. 26, 2011.

An Office Action together issued during the prosecution with the English translation dated May 24, 2016, which issued during the prosecution of Japanese Patent Application No. 2014-526598.

U.S. Appl. No. 61/560,385, filed Nov. 16, 2011.
U.S. Appl. No. 61/603,340, filed Feb. 26, 2012.
U.S. Appl. No. 61/603,344, filed Feb. 26, 2012.
U.S. Appl. No. 61/609,763, filed Mar. 12, 2012.
U.S. Appl. No. 61/613,408, filed Mar. 20, 2012.
U.S. Appl. No. 61/635,360, filed Apr. 19, 2012.
U.S. Appl. No. 61/539,998, filed Sep. 28, 2011.
U.S. Appl. No. 61/496,019, filed Jun. 12, 2011.

Duguet A et al., "Control of tracheal cuff pressure: a pilot study using a pneumatic device," Intensive Care Med. Jan. 2007;33(1):128-32.

Maggiore SM et al., "Closed versus open suctioning techniques," Minerva Anestesiol. May 2002;68(5):360-4.

Notice of Allowance Action dated Dec. 2, 2014, which issued during the prosecution of U.S. Appl. No. 13/806,958.

U.S. Appl. No. 61/483,699, filed May 8, 2011.
U.S. Appl. No. 61/473,790, filed Apr. 10, 2011.
U.S. Appl. No. 61/468,990, filed Mar. 29, 2011.
U.S. Appl. No. 61/660,832, filed Jun. 18, 2012.
U.S. Appl. No. 61/655,801, filed Jun. 5, 2012.
U.S. Appl. No. 61/673,744, filed Jul. 20, 2012.

An Office Action together with the English translation dated Jan. 26, 2016, which issued during the prosecution of Japanese Patent Application No. 2014-501798.

European Search Report dated Jan. 14, 2016, which issued during the prosecution of Applicant's European App No. 12828334.

Search Report dated Jun. 6, 2016, which issued during the prosecution of GB Patent Application No. 1600233.9.

An Office Action dated Feb. 24, 2017, which issued during the prosecution of U.S. Appl. No. 15/377,575.

An Invication to pay additional fees dated Mar. 24, 2017, which issued during the prosecution of Applicant's PCT/IL2016/051367.

An International Search Report and a Written Opinion both dated May 26, 2017, which issued during the prosecution of Applicant's PCT/IL2016/051367.

An International Search Report and a Written Opinion both dated Nov. 15, 2012, which issued during the prosecution of Applicant's PCT/IL2012/000320.

U.S. Appl. No. 62/336,894, filed May 16, 2016.

\* cited by examiner

MECHANICAL USER CONTROL ELEMENTS FOR FLUID INPUT MODULE

CROSS-REFERENCE TO RELATED APPLICATIONS

The present application claims the benefit of U.S. Provisional Application 62/336,894, filed May 16, 2016, which is assigned to the assignee of the present application and is incorporated herein by reference.

FIELD OF THE APPLICATION

The present invention relates generally to medical suction catheter devices, and specifically to catheter devices for aspiration of tracheobronchial secretions and/or cleaning of tracheal ventilation tubes.

BACKGROUND OF THE APPLICATION

Suction catheters are commonly used to aspirate tracheobronchial fluids in patients ventilated with endotracheal tube (ETT) and tracheostomy tube devices. A problematic aspect of the use of suction catheters is the presence of bacterial biofilm within the ETT lumen through which the suction catheter passes. Consequently, as the suction catheter is inserted, there is high risk of it carrying bacterial biofilm from the ETT lumen deeper into the bronchial tree where the suction catheter reaches, and thereby increasing the risk of lung infection. Moreover, buildup of substantial biofilm thickness reduces the effective free lumen of the ETT for air passage. Therefore, there is a need for maintaining cleaner ETT lumens between suction operations, and preventing buildup of significant biofilm thickness.

UK Publication GB 2482618 A to Einav et al., which is assigned to the assignee of the present application and is incorporated herein by reference, describes a multi-lumen catheter for multiple fluids conduction, including balloon inflation with air via an inflation lumen, suction via a suction lumen, and cleaning fluids delivery via a cleaning fluid-delivery lumen.

U.S. Pat. No. 8,999,074 to Zachar et al., which is assigned to the assignee of the present application and is incorporated herein by reference, describes a cleaning catheter that includes fluid-delivery and suction lumens. A flow regulator defines suction and fluid ports. A mechanical user control element is configured to mechanically and non-electrically set activation states of the flow regulator, and transition between first and third configurations via a second configuration. When the control element is in the first configuration, the flow regulator blocks fluid communication (a) between the suction port and the suction lumen and (b) between the fluid port and the fluid-delivery lumen. When the control element is in the second configuration, the flow regulator effects fluid communication between the suction port and the suction lumen, and blocks fluid communication between the fluid port and the fluid-delivery lumen. When the control element is in the third configuration, the flow regulator effects fluid communication (a) between the suction port and the suction lumen and (b) between the fluid port and the fluid-delivery lumen.

SUMMARY OF THE APPLICATION

Some applications of the present invention provide a multi-lumen catheter for cleaning an inner surface of a tracheal ventilation tube. Some techniques of the present invention enable single-handed simultaneous activation of inflation of an inflatable element and suctioning in a closed suction system for use with the tracheal ventilation tube. A closed suction system allows catheters to be used repeatedly without being detached from the tube system including the ventilation air supply. Applications of the present invention generally provide simple user control of conduction of fluids under positive and negative pressure (suction).

The cleaning catheter is insertable into the tracheal ventilation tube, and is shaped so as to define one or more distal suction orifices. The cleaning catheter comprises an elongate, flexible, tubular catheter main body, and an inflatable element, which is mounted to the catheter main body, typically at a location within 3 cm of at least one of the one or more distal suction orifices. An input module is coupled to the cleaning catheter, and comprises an inflation module, which comprises an inflation chamber separate from the suction source. The input module also comprises a flow regulator, which is shaped so as to define a suction port coupleable in fluid communication with the suction source.

In some configurations, the input module further comprises:
  a mechanical suction-control button, which is configured to assume at least first and second spatial positions;
  a mechanical inflation-control button, which is configured to (a) assume at least first and second spatial positions, and (b) mechanically and non-electrically increase pressure in the interior of the inflation chamber during a transition of the mechanical inflation-control button from its first spatial position to its second spatial position; and
  a reversibly-engageable linking element, which is moveable with respect to the mechanical suction-control button and the mechanical inflation-control button, and is configured to assume at least (a) a first spatial position, in which the linking element does not engage the mechanical suction-control button when the mechanical suction-control button is in its second spatial position (and, optionally, prevents the transition of the mechanical inflation-control button from its first spatial position to its second spatial position), and (b) a second spatial position, In these configurations, the input module is arranged such that:
  at least when the mechanical suction-control button is in its first spatial position, the flow regulator blocks fluid communication between the suction source and the distal suction orifices, and at least when the mechanical suction-control button is in its second spatial position, the flow regulator connects the suction source and the distal suction orifices in fluid communication via the suction lumen, and
  when (a) the linking element is in its second spatial position and (b) the mechanical suction-control button and the mechanical inflation-control button are in their respective first spatial positions: depression of the linking element transitions both the mechanical suction-control button and the mechanical inflation-control button to their respective second spatial positions, typically such that the linking element engages both the mechanical suction-control button and the mechanical inflation-control button at least when the mechanical suction-control button is in its second spatial position (and typically also when the mechanical suction-control button is in its first spatial position).

For some applications, the input module is arranged such that transitioning of the linking element from its first spatial position to its second spatial position simultaneously (a) unlocks the mechanical inflation-control button from its first spatial position, and (b) links the mechanical suction-control button with the mechanical inflation-control button.

In other configurations, the input module further comprises a reversibly-engageable linking element, which is moveable with respect to the mechanical suction-control button and the mechanical inflation-control button, and is configured to assume at least first and second spatial positions. The input module is arranged such that:

- at least when the mechanical suction-control button is in its first spatial position, the flow regulator blocks fluid communication between the suction source and the distal suction orifices, and at least when the mechanical suction-control button is in its second spatial position, the flow regulator connects the suction source and the distal suction orifices in fluid communication via the suction lumen,
- when (a) the linking element is in its first spatial position and (b) the mechanical suction-control button and the mechanical inflation-control button are in their respective first spatial positions: depression of the linking element does not transition the mechanical inflation-control button to its second spatial position, and
- when (a) the linking element is in its second spatial position and (b) the mechanical suction-control button and the mechanical inflation-control button are in their respective first spatial positions: depression of the linking element transitions the mechanical inflation-control button to its second spatial position.

For suctioning the trachea, typically the following steps are performed:

- inserting the cleaning catheter into the ventilation tube in a proximal to distal direction while the inflatable element (e.g., balloon) is essentially deflated; typically, in order to perform "deep suction," the distal end of the cleaning catheter is advanced beyond the distal end of the ventilation tube; and
- applying suction to the trachea.

For cleaning a ventilation tube, the cleaning action typically comprises the following steps, which are typically performed in the following order:

- inserting the cleaning catheter into the ventilation tube in a proximal to distal direction while the inflatable element (e.g., balloon) is essentially deflated;
- applying suction and inflating the inflatable element at a location near the distal end of the ventilation tube (typically within 2 cm of the distal end);
- withdrawing the catheter along the ventilation tube in a distal to proximal direction while the inflatable element is inflated and suction is applied to the one or more suction orifices; and
- deflating the inflatable element when the inflatable element is near the proximal end of the ventilation tube or fully outside the proximal end of the ventilation tube.

There is therefore provided, in accordance with an application of the present invention, apparatus for use with a tracheal ventilation tube and a suction source, the apparatus including:

(A) a cleaning catheter, which is insertable into the ventilation tube and includes:
  (i) an elongate, flexible, tubular catheter main body, which is shaped so as to define (a) one or more distal suction orifices, (b) a suction lumen, and (c) an inflation lumen; and
  (ii) an inflatable element, which is mounted to the catheter main body; and (B) an input module, which is coupled to the cleaning catheter, and includes:
  (i) an inflation module, which includes an inflation chamber, wherein the inflation lumen couples an interior of the inflation chamber in fluid communication with an interior of the inflatable element;
  (ii) a flow regulator, which is shaped so as to define a suction port coupleable in fluid communication with the suction source;
  (iii) a mechanical suction-control button, which is configured to assume at least first and second spatial positions;
  (iv) a mechanical inflation-control button, which is configured to (a) assume at least first and second spatial positions, and (b) mechanically and non-electrically increase pressure in the interior of the inflation chamber during a transition of the mechanical inflation-control button from its first spatial position to its second spatial position; and
  (v) a reversibly-engageable linking element, which is moveable with respect to the mechanical suction-control button and the mechanical inflation-control button, and is configured to assume at least (a) a first spatial position, in which the linking element prevents the transition of the mechanical inflation-control button from its first spatial position to its second spatial position, and (b) a second spatial position, wherein the input module is arranged such that:
at least when the mechanical suction-control button is in its first spatial position, the flow regulator blocks fluid communication between the suction source and the distal suction orifices, and at least when the mechanical suction-control button is in its second spatial position, the flow regulator connects the suction source and the distal suction orifices in fluid communication via the suction lumen, and when (a) the linking element is in its second spatial position and (b) the mechanical suction-control button and the mechanical inflation-control button are in their respective first spatial positions: depression of the linking element transitions both the mechanical suction-control button and the mechanical inflation-control button to their respective second spatial positions.

There is further provided, in accordance with an application of the present invention, apparatus for use with a tracheal ventilation tube and a suction source, the apparatus including:

(A) a cleaning catheter, which is insertable into the ventilation tube and includes:
  (i) an elongate, flexible, tubular catheter main body, which is shaped so as to define (a) one or more distal suction orifices, (b) a suction lumen, and (c) an inflation lumen; and
  (ii) an inflatable element, which is mounted to the catheter main body; and (B) an input module, which is coupled to the cleaning catheter, and includes:
  (i) an inflation module, which includes an inflation chamber, wherein the inflation lumen couples an interior of the inflation chamber in fluid communication with an interior of the inflatable element;
  (ii) a flow regulator, which is shaped so as to define a suction port coupleable in fluid communication with the suction source;
  (iii) a mechanical suction-control button, which is configured to assume at least first and second spatial positions;

(iv) a mechanical inflation-control button, which is configured to (a) assume at least first and second spatial positions, and (b) mechanically and non-electrically increase pressure in the interior of the inflation chamber during a transition of the mechanical inflation-control button from its first spatial position to its second spatial position; and (v) a reversibly-engageable linking element, which is moveable with respect to the mechanical suction-control button and the mechanical inflation-control button, and is configured to assume at least (a) a first spatial position, in which the linking element does not engage the suction-control button when the suction-control button is in its second spatial position, and (b) a second spatial position, wherein the input module is arranged such that:

at least when the mechanical suction-control button is in its first spatial position, the flow regulator blocks fluid communication between the suction source and the distal suction orifices, and at least when the mechanical suction-control button is in its second spatial position, the flow regulator connects the suction source and the distal suction orifices in fluid communication via the suction lumen, and when (a) the linking element is in its second spatial position and (b) the mechanical suction-control button and the mechanical inflation-control button are in their respective first spatial positions: depression of the linking element transitions both the mechanical suction-control button and the mechanical inflation-control button to their respective second spatial positions, such that the linking element engages both the suction-control button and the mechanical inflation-control button at least when the suction-control button is in its second spatial position.

For some applications, the inflatable element is mounted to the catheter main body at a location within 3 cm of at least one of the one or more distal suction orifices.

For some applications, the input module is arranged such that the linking element, when in its first spatial position, (a) locks the mechanical inflation-control button in the first spatial position of the mechanical inflation-control button, and (b) does not lock the mechanical suction-control button.

For some applications, the first and the second spatial positions of the linking element are first and second axial positions, and the linking element is configured to assume at least the first and the second axial positions.

For some applications:

the first and the second spatial positions of the mechanical suction-control button are first and second radial positions, and the mechanical suction-control button is configured to assume at least the first and the second radial positions, and the first and the second spatial positions of the mechanical inflation-control button are first and second radial positions, and the mechanical inflation-control button is configured to assume at least the first and the second radial positions.

For some applications, the linking element is moveably attached to the mechanical inflation-control button.

For some applications, the input module is arranged such that the linking element, when in its first spatial position, does not prevent user access to the mechanical suction-control button.

For some applications, the input module is arranged such that the linking element, when in its first spatial position, does not engage the mechanical suction-control button.

For some applications, the input module is arranged such that the linking element, when in its first spatial position, engages the mechanical inflation-control button.

For some applications, the input module is arranged such that the linking element, when in its first spatial position, is not arranged to transition the mechanical suction-control button all the way to its second spatial position.

For some applications, the input module is arranged such that when (a) the linking element is in its second spatial position and (b) the mechanical suction-control button and the mechanical inflation-control button are in their respective first spatial positions: the depression of the linking element simultaneously transitions both the mechanical suction-control button and the mechanical inflation-control button to their respective second spatial positions.

For some applications, the linking element is arranged to axially slide between its first and second spatial positions.

For some applications, the linking element is arranged to rotate between its first and second spatial positions.

For some applications, the mechanical suction-control button is disposed proximally to the mechanical inflation-control button.

For some applications, the suction port is coupled in fluid communication with the suction source.

For some applications, the inflation chamber has a volume of between 1 and 10 cc when the first mechanical control element is in its first spatial position.

For some applications, the mechanical suction-control button and the mechanical inflation-control button are biased toward their respective first spatial positions.

For some applications, the input module includes one or more springs that are arranged to bias the mechanical suction-control button and the mechanical inflation-control button toward their respective first spatial positions.

For some applications, the input module includes exactly one spring that is arranged to bias both the mechanical suction-control button and the mechanical inflation-control button toward their respective first spatial positions.

For some applications, the one or more springs are disposed outside the inflation chamber.

For some applications, at least a portion of one of the one or more springs is disposed alongside the inflation chamber.

For some applications:

the inflation chamber includes (a) rigid lateral chamber walls, and (b) a moveable rigid compression wall that forms an airtight seal with the rigid lateral chamber walls, and the input module is configured such that the transition of the mechanical inflation-control button from its first spatial position to its second spatial position moves the moveable rigid compression wall with respect to the rigid lateral chamber walls, thereby mechanically and non-electrically increasing the pressure in the interior of the inflation chamber.

For some applications:

the inflation chamber includes an elastic compartment, and the input module is configured such that the transition of the mechanical inflation-control button from its first spatial position to its second spatial position compresses the elastic compartment, thereby mechanically and non-electrically increasing the pressure in an interior of the elastic compartment.

For some applications, the mechanical inflation-control button is configured to increase the pressure in the interior of the inflation chamber by mechanically and non-electrically compressing the inflation chamber during the at least a portion of the transition of the mechanical inflation-control button from its first spatial position to its second spatial position.

For some applications, the inflation chamber transitions from a lower level of compression to a higher level of compression during the at least a portion of the transition of the mechanical inflation-control button from its first spatial position to its second spatial position, and the input module is configured to elastically bias the inflation chamber toward the lower level of compression.

For some applications, the inflation module is elastically biased toward the lower level of compression.

For some applications:
the mechanical suction-control button is shaped so as to define a suction-control user interface surface,
the mechanical inflation-control button is not shaped so as to define a user interface surface,
the linking element is shaped so as to define a linking user interface surface,
the input module is arranged such that when (a) the linking element is in its first spatial position and (b) the mechanical suction-control button is in its first spatial position: (a) at least a portion of the suction-control user interface surface is visible from outside the input module, and (b) depression of the suction-control user interface surface transitions the mechanical suction-control button to its second spatial position, and
the input module is arranged such that when (a) the linking element is in its second spatial position and (b) the mechanical suction-control button and the mechanical inflation-control button are in their respective first spatial positions: depression of the linking user interface surface transitions both the mechanical suction-control button and the mechanical inflation-control button to their respective second spatial positions.

For some applications, when (a) the linking element is in its first spatial position and (b) the mechanical suction-control button is in its first spatial position: at least 1 cm2 of the suction-control user interface surface is visible from outside the input module.

For some applications, the input module is arranged such that the linking element, when in its second spatial position, blocks external access to the suction-control user interface surface.

For some applications, at least 1 cm2 of the linking user interface surface is visible from outside the input module.

For some applications:
the mechanical inflation-control button is configured to additionally (a) assume a deflation-inducing spatial position, wherein the first spatial position is between the deflation-inducing spatial position and the second spatial position, and (b) mechanically and non-electrically increase the pressure in the interior of the inflation chamber during transition of the mechanical inflation-control button from its deflation-inducing spatial position to its first spatial position, and
the input module further includes a mechanical deflation-control button, which is arranged such that when the mechanical inflation-control button is in its first spatial position, depression of the mechanical deflation-control button transitions the mechanical inflation-control button from its first spatial position to its deflation-inducing spatial position, thereby deflating the inflatable element.

For some applications, the inflatable element is partially inflated when the mechanical inflation-control button is in its first spatial position.

There is further provided, in accordance with an application of the present invention, apparatus for use with a tracheal ventilation tube and a suction source, the apparatus including:
(A) a cleaning catheter, which is insertable into the ventilation tube and includes:
(i) an elongate, flexible, tubular catheter main body, which is shaped so as to define (a) one or more distal suction orifices, (b) a suction lumen, and (c) an inflation lumen; and
(ii) an inflatable element, which is mounted to the catheter main body; and
(B) an input module, which is coupled to the cleaning catheter, and includes:
(i) an inflation module, which includes an inflation chamber, wherein the inflation lumen couples an interior of the inflation chamber in fluid communication with an interior of the inflatable element;
(ii) a flow regulator, which is shaped so as to define a suction port coupleable in fluid communication with the suction source;
(iii) a mechanical suction-control button, which is configured to assume at least first and second spatial positions;
(iv) a mechanical inflation-control button, which is configured to (a) assume at least first and second spatial positions, and (b) mechanically and non-electrically increase pressure in the interior of the inflation chamber during a transition of the mechanical inflation-control button from its first spatial position to its second spatial position; and
(v) a reversibly-engageable linking element, which is moveable with respect to the mechanical suction-control button and the mechanical inflation-control button, and is configured to assume at least first and second spatial positions,
wherein the input module is arranged such that:
at least when the mechanical suction-control button is in its first spatial position, the flow regulator blocks fluid communication between the suction source and the distal suction orifices, and at least when the mechanical suction-control button is in its second spatial position, the flow regulator connects the suction source and the distal suction orifices in fluid communication via the suction lumen,
when (a) the linking element is in its first spatial position and (b) the mechanical suction-control button and the mechanical inflation-control button are in their respective first spatial positions: depression of the linking element does not transition the mechanical inflation-control button to its second spatial position, and
when (a) the linking element is in its second spatial position and (b) the mechanical suction-control button and the mechanical inflation-control button are in their respective first spatial positions: depression of the linking element transitions the mechanical inflation-control button to its second spatial position.

For some applications, the inflatable element is mounted to the catheter main body at a location within 3 cm of at least one of the one or more distal suction orifices.

For some applications, the linking element is arranged to axially slide between its first and second spatial positions.

For some applications, the first and the second spatial positions of the linking element are first and second axial positions, and the linking element is configured to assume at least the first and the second axial positions.

For some applications:

the first and the second spatial positions of the mechanical suction-control button are first and second radial positions, and the mechanical suction-control button is configured to assume at least the first and the second radial positions, and the first and the second spatial positions of the mechanical inflation-control button are first and second radial positions, and the mechanical inflation-control button is configured to assume at least the first and the second radial positions.

For some applications, the linking element is moveably attached to the mechanical suction-control button.

For some applications, the input module is arranged such that the linking element, when in its first spatial position, does not engage the mechanical inflation-control button.

For some applications, the input module is arranged such that the linking element, when in its second spatial position, engages the mechanical inflation-control button.

For some applications, the mechanical suction-control button is disposed proximally to the mechanical inflation-control button.

For some applications, the suction port is coupled in fluid communication with the suction source.

For some applications, the inflation chamber has a volume of between 1 and 10 cc when the first mechanical control element is in its first spatial position.

For some applications, the mechanical suction-control button covers a portion of the reversibly-engageable linking element.

For some applications:

the mechanical suction-control button is shaped so as to define a suction-control user interface surface, at least a portion of which is visible from outside the input module, the mechanical inflation-control button is not shaped so as to define a user interface surface, the input module is arranged such that when (a) the linking element is in its first spatial position and (b) the mechanical suction-control button is in its first spatial position: depression of the suction-control user interface surface transitions the mechanical suction-control button to its second spatial position, and the input module is arranged such that when (a) the linking element is in its second spatial position and (b) the mechanical suction-control button and the mechanical inflation-control button are in their respective first spatial positions: depression of the suction-control user interface surface causes a first transition of the mechanical suction-control button to its second spatial position, which first transition, via the linking element, causes a second transition of the mechanical inflation-control button to its second spatial position.

For some applications, at least 1 cm2 of the suction-control user interface surface is visible from outside the input module.

For some applications, the input module is arranged such that the second transition occurs simultaneously with the first transition.

For some applications, the input module includes a cover, which is arranged to inhibit user access to the mechanical inflation-control button both when the linking element is in its first spatial position and when the linking element is in its second spatial position.

For some applications, the input module is arranged such that the cover is stationary with respect to the suction port during motion of either the mechanical suction-control button or the mechanical inflation-control button between their respective first and second spatial positions.

For some applications, the mechanical suction-control button and the mechanical inflation-control button are biased toward their respective first spatial positions.

For some applications, the input module includes one or more springs that are arranged to bias the mechanical suction-control button and the mechanical inflation-control button toward their respective first spatial positions.

For some applications, the input module includes exactly one spring that is arranged to bias both the mechanical suction-control button and the mechanical inflation-control button toward their respective first spatial positions.

For some applications, the one or more springs are disposed outside the inflation chamber.

For some applications, at least a portion of one of the one or more springs is disposed alongside the inflation chamber.

For some applications:

the inflation chamber includes (a) rigid lateral chamber walls, and (b) a moveable rigid compression wall that forms an airtight seal with the rigid lateral chamber walls, and the input module is configured such that the transition of the mechanical inflation-control button from its first spatial position to its second spatial position moves the moveable rigid compression wall with respect to the rigid lateral chamber walls, thereby mechanically and non-electrically increasing the pressure in the interior of the inflation chamber.

For some applications:

the inflation chamber includes an elastic compartment, and the input module is configured such that the transition of the mechanical inflation-control button from its first spatial position to its second spatial position compresses the elastic compartment, thereby mechanically and non-electrically increasing the pressure in an interior of the elastic compartment.

For some applications, the mechanical inflation-control button is configured to increase the pressure in the interior of the inflation chamber by mechanically and non-electrically compressing the inflation chamber during the at least a portion of the transition of the mechanical inflation-control button from its first spatial position to its second spatial position.

For some applications, the inflation chamber transitions from a lower level of compression to a higher level of compression during the at least a portion of the transition of the mechanical inflation-control button from its first spatial position to its second spatial position, and the input module is configured to elastically bias the inflation chamber toward the lower level of compression.

For some applications, the inflation module is elastically biased toward the lower level of compression.

For some applications:

the mechanical inflation-control button is configured to additionally (a) assume a deflation-inducing spatial position, wherein the first spatial position is between the deflation-inducing spatial position and the second spatial position, and (b) mechanically and non-electrically increase the pressure in the interior of the inflation chamber during transition of the mechanical inflation-control button from its deflation-inducing spatial position to its first spatial position, and the input module further includes a mechanical deflation-control button, which is arranged such that when the mechanical inflation-control button is in its first spatial position, depression of the mechanical deflation-control button transitions the mechanical inflation-control button from its first spatial position to its deflation-inducing spatial position, thereby deflating the inflatable element.

For some applications, the inflatable element is partially inflated when the mechanical inflation-control button is in its first spatial position.

There is still further provided, in accordance with an application of the present invention, apparatus for use with a tracheal ventilation tube and a suction source, the apparatus including:

(A) a cleaning catheter, which is insertable into the ventilation tube and includes:
  (i) an elongate, flexible, tubular catheter main body, which is shaped so as to define (a) one or more distal suction orifices, (b) a suction lumen, and (c) an inflation lumen; and
  (ii) an inflatable element, which is mounted to the catheter main body; and
(B) an input module, which is coupled to the cleaning catheter, and includes:
  (i) an inflation module, which includes an inflation chamber, wherein the inflation lumen couples an interior of the inflation chamber in fluid communication with an interior of the inflatable element;
  (ii) a flow regulator, which is shaped so as to define a suction port coupleable in fluid communication with the suction source;
  (iii) a mechanical suction-control button, which is configured to assume at least first and second spatial positions;
  (iv) a mechanical inflation-control button, which is configured to (a) assume at least first and second spatial positions, and (b) mechanically and non-electrically increase pressure in the interior of the inflation chamber during a transition of the mechanical inflation-control button from its first spatial position to its second spatial position; and
  (v) exactly one spring that is arranged to bias both the mechanical suction-control button and the mechanical inflation-control button toward their respective first spatial positions,
  wherein the input module is arranged such that (a) at least when the mechanical suction-control button is in its first spatial position, the flow regulator blocks fluid communication between the suction source and the distal suction orifices, and (b) at least when the mechanical suction-control button is in its second spatial position, the flow regulator connects the suction source and the distal suction orifices in fluid communication via the suction lumen.

For some applications, the inflatable element is mounted to the catheter main body at a location within 3 cm of at least one of the one or more distal suction orifices.

For some applications, the exactly one spring is disposed outside the inflation chamber.

For some applications, at least a portion of the exactly one spring is disposed alongside the inflation chamber.

For some applications, the suction port is coupled in fluid communication with the suction source.

For some applications, the inflation chamber has a volume of between 1 and 10 cc when the first mechanical control element is in its first spatial position.

For some applications, the mechanical inflation-control button is configured to increase the pressure in the interior of the inflation chamber by mechanically and non-electrically compressing the inflation chamber during the at least a portion of the transition of the mechanical inflation-control button from its first spatial position to its second spatial position.

For some applications, the inflation chamber transitions from a lower level of compression to a higher level of compression during the at least a portion of the transition of the mechanical inflation-control button from its first spatial position to its second spatial position, and the exactly one spring is arranged to elastically bias the inflation chamber toward the lower level of compression.

For some applications:
  the mechanical inflation-control button is configured to additionally (a) assume a deflation-inducing spatial position, wherein the first spatial position is between the deflation-inducing spatial position and the second spatial position, and (b) mechanically and non-electrically increase the pressure in the interior of the inflation chamber during transition of the mechanical inflation-control button from its deflation-inducing spatial position to its first spatial position, and
  the input module further includes a mechanical deflation-control button, which is arranged such that when the mechanical inflation-control button is in its first spatial position, depression of the mechanical deflation-control button transitions the mechanical inflation-control button from its first spatial position to its deflation-inducing spatial position, thereby deflating the inflatable element.

For some applications, the inflatable element is partially inflated when the mechanical inflation-control button is in its first spatial position.

There is additionally provided, in accordance with an application of the present invention, apparatus for use with a tracheal ventilation tube and a suction source, the apparatus including:

(A) a cleaning catheter, which is insertable into the ventilation tube and includes:
  (i) an elongate, flexible, tubular catheter main body, which is shaped so as to define (a) one or more distal suction orifices, (b) a suction lumen, and (c) an inflation lumen; and
  (ii) an inflatable element, which is mounted to the catheter main body; and
(B) an input module, which is coupled to the cleaning catheter, and includes:
  (i) an inflation module, which includes an inflation chamber, wherein the inflation lumen couples an interior of the inflation chamber in fluid communication with an interior of the inflatable element;
  (ii) a flow regulator, which is shaped so as to define a suction port coupleable in fluid communication with the suction source;
  (iii) a mechanical suction-control button, which is configured to assume at least first, second, and third spatial positions, the second spatial position between the first and the third spatial positions;
  (iv) a mechanical inflation-control button, which (a) is not shaped so as to define a user interface surface, (b) is configured to assume at least first and second spatial positions, and (c) is configured to mechanically and non-electrically increase pressure in the interior of the inflation chamber during a transition of the mechanical inflation-control button from its first spatial position to its second spatial position;
  (v) a reversibly-engageable linking element, which is fixed to the mechanical suction-control button, and is configured to assume at least first, second, and third spatial positions, the second spatial position between the first and the third spatial positions; and
  (vi) a cover, which is arranged to inhibit user access to the mechanical inflation-control button,
  wherein the input module is arranged such that:
  at least when the mechanical suction-control button is in its first spatial position, the flow regulator blocks fluid communication between the suction source and the distal suction orifices, and at least when the mechanical suction-control button is in its second and third spatial positions, the flow regulator connects the suction source and the distal suction orifices in fluid communication via the suction lumen, a first transition of the mechanical suction-control button from its first spatial position to its second spatial position causes a second transition of the linking element from its first spatial position to its second spatial position, and a third transition of the mechanical suction-control button from its second spatial position to its third spatial position causes a fourth transition of the linking element from its second spatial position to its third spatial position, which in turn causes a fifth transition of the mechanical inflation-control button to its second spatial position.

For some applications, the inflatable element is mounted to the catheter main body at a location within 3 cm of at least one of the one or more distal suction orifices.

For some applications, the input module is arranged such that the first transition does not move the mechanical inflation-control button.

For some applications, the input module is arranged such that the first transition does not radially move the mechanical inflation-control button.

For some applications, the input module is arranged such that the fifth transition occurs simultaneously with the fourth transition.

For some applications, the linking element is radially-moveable, the first, the second, and the third spatial positions are first, second, and third radial positions, respectively, and the linking element is configured to assume at least the first, the second, and the third radial positions.

For some applications:

the first, the second, and the third spatial positions of the mechanical suction-control button are first, second, and third radial positions, and the mechanical suction-control button is configured to assume at least the first, the second, and the third radial positions, and the first and the second spatial positions of the mechanical inflation-control button are first and second radial positions, and the mechanical inflation-control button is configured to assume at least the first and the second radial positions.

For some applications, the mechanical suction-control button is shaped so as to define a suction-control user interface surface, at least 1 cm2 of which is visible from outside the input module, and depression of the suction-control user interface surface causes the first and the third transitions.

For some applications, less than 1 cm2 of the linking element is visible from outside the input module.

For some applications, the linking element is shaped so as to define a linking user interface surface, at least a portion of which is visible from outside the input module, and depression of the linking user interface surface causes the first and the third transitions.

For some applications, at least 1 cm2 of the linking user interface surface is visible from outside the input module.

For some applications:

the input module is configured to apply a maximum level of suction to the distal suction orifices when the mechanical suction-control button is in its third spatial position, and the input module is configured, during a transition of the mechanical suction-control button from its first spatial position to its third spatial position via its second spatial position, to apply at least 30% of the maximum level of suction to the distal suction orifices before inflation of the inflatable element begins.

For some applications, the input module is arranged such that the cover is stationary with respect to the suction port during motion of either the mechanical suction-control button or the mechanical inflation-control button between their respective first and second spatial positions.

For some applications, the mechanical suction-control button is disposed proximally to the mechanical inflation-control button.

For some applications, the suction port is coupled in fluid communication with the suction source.

For some applications, the inflation chamber has a volume of between 1 and 10 cc when the first mechanical control element is in its first spatial position.

For some applications, the mechanical suction-control button and the mechanical inflation-control button are biased toward their respective first spatial positions.

For some applications, the input module includes one or more springs that are arranged to bias the mechanical suction-control button and the mechanical inflation-control button toward their respective first spatial positions.

For some applications, the input module includes exactly one spring that is arranged to bias both the mechanical suction-control button and the mechanical inflation-control button toward their respective first spatial positions.

For some applications, the one or more springs are disposed outside the inflation chamber.

For some applications, at least a portion of one of the one or more springs is disposed alongside the inflation chamber.

For some applications:

the inflation chamber includes (a) rigid lateral chamber walls, and (b) a moveable rigid compression wall that forms an airtight seal with the rigid lateral chamber walls, and the input module is configured such that the transition of the mechanical inflation-control button from its first spatial position to its second spatial position moves the moveable rigid compression wall with respect to the rigid lateral chamber walls, thereby mechanically and non-electrically increasing the pressure in the interior of the inflation chamber.

For some applications:

the inflation chamber includes an elastic compartment, and the input module is configured such that the transition of the mechanical inflation-control button from its first spatial position to its second spatial position compresses the elastic compartment, thereby mechanically and non-electrically increasing the pressure in an interior of the elastic compartment.

For some applications, the mechanical inflation-control button is configured to increase the pressure in the interior of the inflation chamber by mechanically and non-electrically compressing the inflation chamber during the at least a portion of the transition of the mechanical inflation-control button from its first spatial position to its second spatial position.

For some applications, the inflation chamber transitions from a lower level of compression to a higher level of compression during the at least a portion of the transition of the mechanical inflation-control button from its first spatial position to its second spatial position, and the input module is configured to elastically bias the inflation chamber toward the lower level of compression.

For some applications, the inflation module is elastically biased toward the lower level of compression.

For some applications:

the mechanical inflation-control button is configured to additionally (a) assume a deflation-inducing spatial position, wherein the first spatial position is between the deflation-inducing spatial position and the second spatial position, and (b) mechanically and non-electrically increase the pressure in the interior of the inflation chamber during transition of the mechanical inflation-control button from its deflation-inducing spatial position to its first spatial position, and the input module further includes a mechanical deflation-control button, which is arranged such that when the mechanical inflation-control button is in its first spatial position, depression of the mechanical deflation-control button transitions the mechanical inflation-control button from its first spatial position to its deflation-inducing spatial position, thereby deflating the inflatable element.

For some applications, the inflatable element is partially inflated when the mechanical inflation-control button is in its first spatial position.

There is yet additionally provided, in accordance with an application of the present invention, apparatus for use with a tracheal ventilation tube and a suction source, the apparatus including:

(A) a cleaning catheter, which is insertable into the ventilation tube and includes:
  (i) an elongate, flexible, tubular catheter main body, which is shaped so as to define (a) one or more distal suction orifices, (b) a suction lumen, and (c) an inflation lumen; and
  (ii) an inflatable element, which is mounted to the catheter main body; and
(B) an input module, which is coupled to the cleaning catheter, and includes:
  (i) an inflation module, which includes an inflation chamber, wherein the inflation lumen couples an interior of the inflation chamber in fluid communication with an interior of the inflatable element;
  (ii) a flow regulator, which is shaped so as to define a suction port coupleable in fluid communication with the suction source;
  (iii) a mechanical suction-control button, which is configured to assume at least first, second, and third spatial positions, the second spatial position between the first and the third spatial positions;
  (iv) a mechanical inflation-control button, which (a) is not shaped so as to define a user interface surface, (b) is configured to assume at least first and second spatial positions, and (c) is configured to mechanically and non-electrically increase pressure in the interior of the inflation chamber during a transition of the mechanical inflation-control button from its first spatial position to its second spatial position;
  (v) a reversibly-engageable linking element, which is fixed to the mechanical suction-control button, and is configured to assume at least:
    (a) a first spatial position, in which the linking element does not engage the mechanical inflation-control button,
    (b) a second spatial position, and
    (c) a third spatial position, in which the linking element engages the mechanical inflation-control button, wherein the second spatial position is between the first and the third spatial positions; and
  (vi) a moveable stopper, which is moveably fixed to the input module, and which is configured to assume at least:
    a first spatial position, in which the moveable stopper blocks a first transition of the linking element from its second spatial position to its third spatial position, and
    a second spatial position, in which the moveable stopper does not block the first transition of the linking element from its second spatial position to its third spatial position,
  wherein the input module is arranged such that:
  at least when the mechanical suction-control button is in its first spatial position, the flow regulator blocks fluid communication between the suction source and the distal suction orifices, and at least when the mechanical suction-control button is in its second and third spatial positions, the flow regulator connects the suction source and the distal suction orifices in fluid communication via the suction lumen, and
  when (a) the linking element is in its second spatial position, (b) the mechanical suction-control button is in its second spatial position, (c) the mechanical inflation-control button is in its first spatial position, and (d) the moveable stopper is in its second spatial position: depression of the mechanical control button causes a second transition of the mechanical suction-control button to its third spatial position, which second transition, via the linking element, causes a third transition of the mechanical inflation-control button to its second spatial position.

For some applications, the inflatable element is mounted to the catheter main body at a location within 3 cm of at least one of the one or more distal suction orifices.

For some applications, the input module is arranged such that the third transition occurs simultaneously with the second transition.

For some applications, the linking element is shaped so as to define a linking user interface surface, at least a portion of which is visible from outside the input module, and depression of the linking user interface surface transitions the mechanical suction-control button from its first spatial position, to its second spatial position, to its third spatial position.

For some applications, at least 1 cm2 of the linking user interface surface is visible from outside the input module.

For some applications, the mechanical suction-control button is shaped so as to define a suction-control user interface surface, at least a portion of which is visible from outside the input module, and depression of the suction-control user interface surface transitions the mechanical suction-control button from its first spatial position, to its second spatial position, to its third spatial position.

For some applications, at least 1 cm2 of the suction-control user interface surface is visible from outside the input module.

For some applications, the linking element is radially-moveable, the first, the second, and the third spatial positions are first, second, and third radial positions, respectively, and the linking element is configured to assume at least the first, the second, and the third radial positions.

For some applications:

the first, the second, and the third spatial positions of the mechanical suction-control button are first, second, and third radial positions, and wherein the mechanical suction-control button is configured to assume at least the first, the second, and the third radial positions, and wherein the first and the second spatial positions of the mechanical inflation-control button are first and second radial positions, and wherein the mechanical inflation-control button is configured to assume at least the first and the second radial positions.

For some applications, wherein the mechanical suction-control button is disposed proximally to the mechanical inflation-control button.

For some applications:

the input module is configured to apply a maximum level of suction to the distal suction orifices when the mechanical suction-control button is in its third spatial position, and the input module is configured, during a transition of the mechanical suction-control button from its first spatial position to its third spatial position via its second spatial position, to apply at least 30% of the maximum level of suction to the distal suction orifices before inflation of the inflatable element begins.

For some applications, the suction port is coupled in fluid communication with the suction source.

For some applications, the inflation chamber has a volume of between 1 and 10 cc when the first mechanical control element is in its first spatial position.

For some applications, the mechanical suction-control button and the mechanical inflation-control button are biased toward their respective first spatial positions.

For some applications, the input module includes one or more springs that are arranged to bias the mechanical suction-control button and the mechanical inflation-control button toward their respective first spatial positions.

For some applications, the input module includes exactly one spring that is arranged to bias both the mechanical suction-control button and the mechanical inflation-control button toward their respective first spatial positions.

For some applications, the one or more springs are disposed outside the inflation chamber.

For some applications, at least a portion of one of the one or more springs is disposed alongside the inflation chamber.

For some applications:

the inflation chamber includes (a) rigid lateral chamber walls, and (b) a moveable rigid compression wall that forms an airtight seal with the rigid lateral chamber walls, and the input module is configured such that the transition of the mechanical inflation-control button from its first spatial position to its second spatial position moves the moveable rigid compression wall with respect to the rigid lateral chamber walls, thereby mechanically and non-electrically increasing the pressure in the interior of the inflation chamber.

For some applications:

the inflation chamber includes an elastic compartment, and the input module is configured such that the transition of the mechanical inflation-control button from its first spatial position to its second spatial position compresses the elastic compartment, thereby mechanically and non-electrically increasing the pressure in an interior of the elastic compartment.

For some applications, the mechanical inflation-control button is configured to increase the pressure in the interior of the inflation chamber by mechanically and non-electrically compressing the inflation chamber during the at least a portion of the transition of the mechanical inflation-control button from its first spatial position to its second spatial position.

For some applications, the inflation chamber transitions from a lower level of compression to a higher level of compression during the at least a portion of the transition of the mechanical inflation-control button from its first spatial position to its second spatial position, and the input module is configured to elastically bias the inflation chamber toward the lower level of compression.

For some applications, the inflation module is elastically biased toward the lower level of compression.

For some applications:

the mechanical inflation-control button is configured to additionally (a) assume a deflation-inducing spatial position, wherein the first spatial position is between the deflation-inducing spatial position and the second spatial position, and (b) mechanically and non-electrically increase the pressure in the interior of the inflation chamber during transition of the mechanical inflation-control button from its deflation-inducing spatial position to its first spatial position, and the input module further includes a mechanical deflation-control button, which is arranged such that when the mechanical inflation-control button is in its first spatial position, depression of the mechanical deflation-control button transitions the mechanical inflation-control button from its first spatial position to its deflation-inducing spatial position, thereby deflating the inflatable element.

For some applications, the inflatable element is partially inflated when the mechanical inflation-control button is in its first spatial position.

There is also provided, in accordance with an application of the present invention, apparatus for use with a tracheal ventilation tube, the apparatus including:

(A) a cleaning catheter, which is insertable into the ventilation tube and includes:
  (i) an elongate, flexible, tubular catheter main body, which is shaped so as to define (a) one or more distal suction orifices, and (b) an inflation lumen; and
  (ii) an inflatable element, which is mounted to the catheter main body; and (B) an input module, which is coupled to the cleaning catheter, and includes:
  (i) an inflation module, which includes an inflation chamber, wherein the inflation lumen couples an interior of the inflation chamber in fluid communication with an interior of the inflatable element;
  (ii) a mechanical inflation-control button, which is configured to (a) assume at least a deflation-inducing spatial position, a first spatial position, and a second spatial positions, the first spatial position between the deflation-inducing spatial position and the second spatial position, and (b) mechanically and non-electrically increase pressure in the interior of the inflation chamber during transition of the mechanical inflation-control button from its deflation-inducing spatial position to its first spatial position, and from its first spatial position to its second spatial position; and
  (iii) a mechanical deflation-control button, which is arranged such that when the mechanical inflation-control button is in its first spatial position, depression of the mechanical deflation-control button transitions the mechanical inflation-control button from its first spatial position to its deflation-inducing spatial position, thereby deflating the inflatable element.

For some applications, the mechanical inflation-control button is in a resting state when in its first spatial position.

For some applications, the input module includes one or more springs that are arranged to bias the mechanical inflation-control button from its second spatial position toward its first spatial position.

For some applications, the one or more springs are not arranged to bias the mechanical inflation-control button from its first spatial position toward its deflation-inducing spatial position.

For some applications, the inflatable element is partially inflated when the mechanical inflation-control button is in its second spatial position.

For some applications, the deflation-inducing, the first, and the second spatial positions are deflation-inducing, first, and second radial positions, and the mechanical inflation-control button is configured to assume at least the deflation-inducing, the first, and the second radial positions.

For some applications:
the inflation chamber includes (a) rigid lateral chamber walls, and (b) a moveable rigid compression wall that forms an airtight seal with the rigid lateral chamber walls, and
the input module is configured such that the transition of the mechanical inflation-control button from its first spatial position to its second spatial position, and from its second spatial position to its third spatial position, moves the moveable rigid compression wall with respect to the rigid lateral chamber walls, thereby mechanically and non-electrically increasing the pressure in the interior of the inflation chamber.

For some applications:
the inflation chamber includes an elastic compartment, and
the input module is configured such that the transition of the mechanical inflation-control button from its first spatial position to its second spatial position, and from its second spatial position to its third spatial position, compresses the elastic compartment, thereby mechanically and non-electrically increasing the pressure in an interior of the elastic compartment.

There is further provided, in accordance with an application of the present invention, a method for use with a tracheal ventilation tube and a suction source, the method including:
providing a cleaning catheter, which is insertable into the ventilation tube and includes (i) an elongate, flexible, tubular catheter main body, which is shaped so as to define (a) one or more distal suction orifices, (b) a suction lumen, and (c) an inflation lumen; and (ii) an inflatable element, which is mounted to the catheter main body;
providing an input module, which is coupled to the cleaning catheter, and includes (i) an inflation module, which includes an inflation chamber, wherein the inflation lumen couples an interior of the inflation chamber in fluid communication with an interior of the inflatable element; (ii) a flow regulator, which is shaped so as to define a suction port coupleable in fluid communication with the suction source; (iii) a mechanical suction-control button, which is configured to assume at least first and second spatial positions; (iv) a mechanical inflation-control button, which is configured to (a) assume at least first and second spatial positions, and (b) mechanically and non-electrically increase pressure in the interior of the inflation chamber during a transition of the mechanical inflation-control button from its first spatial position to its second spatial position; and (v) a reversibly-engageable linking element, which is moveable with respect to the mechanical suction-control button and the mechanical inflation-control button, and is configured to assume at least (a) a first spatial position, in which the linking element prevents the transition of the mechanical inflation-control button from its first spatial position to its second spatial position, and (b) a second spatial position, wherein the input module is arranged such that: (i) at least when the mechanical suction-control button is in its first spatial position, the flow regulator blocks fluid communication between the suction source and the distal suction orifices, and at least when the mechanical suction-control button is in its second spatial position, the flow regulator connects the suction source and the distal suction orifices in fluid communication via the suction lumen, and (ii) when (a) the linking element is in its second spatial position and (b) the mechanical suction-control button and the mechanical inflation-control button are in their respective first spatial positions: depression of the linking element transitions both the mechanical suction-control button and the mechanical inflation-control button to their respective second spatial positions;
coupling the suction portion in fluid communication with the suction source; and
inserting the cleaning catheter, in a proximal to distal direction, into the ventilation tube inserted in a trachea of a patient, and advancing the cleaning catheter until a distal end of the catheter main body is axially disposed in the ventilation tube at a location more distal than an axial mid-point of the ventilation tube.

There is still further provided, in accordance with an application of the present invention, a method for use with a tracheal ventilation tube and a suction source, the method including:
providing a cleaning catheter, which is insertable into the ventilation tube and includes (i) an elongate, flexible, tubular catheter main body, which is shaped so as to define (a) one or more distal suction orifices, (b) a suction lumen, and (c) an inflation lumen; and (ii) an inflatable element, which is mounted to the catheter main body;
providing an input module, which is coupled to the cleaning catheter, and includes (i) an inflation module, which includes an inflation chamber, wherein the inflation lumen couples an interior of the inflation chamber in fluid communication with an interior of the inflatable element; (ii) a flow regulator, which is shaped so as to define a suction port coupleable in fluid communication with the suction source; (iii) a mechanical suction-control button, which is configured to assume at least first and second spatial positions; (iv) a mechanical inflation-control button, which is configured to (a) assume at least first and second spatial positions, and (b) mechanically and non-electrically increase pressure in the interior of the inflation chamber during a transition of the mechanical inflation-control button from its first spatial position to its second spatial position; and (v) a reversibly-engageable linking element, which is moveable with respect to the mechanical suction-control button and the mechanical inflation-control button, and is configured to assume at least (a) a first spatial position, in which the linking element does not engage the suction-control button when the suction-control button is in its second spatial position, and (b) a second spatial position, wherein the input module is arranged such that: (i) at least when the mechanical suction-control button is in its first spatial position, the flow regulator blocks fluid communication between the suction source and the distal suction orifices, and at least when the mechanical suction-control button is in its second spatial position, the flow regulator connects the suction source and the distal suction orifices in fluid communication via the suction lumen, and (ii) when (a) the linking element is in its second spatial position and (b) the mechanical suction-control button and the mechanical inflation-control button are in their respective first spatial positions: depression of the linking element transitions both the mechanical suction-control button and the mechanical inflation-control button to their respective second spatial positions, such that the linking element engages both the suction-control button and the mechanical inflation-control button at least when the suction-control button is in its second spatial position;

coupling the suction portion in fluid communication with the suction source; and inserting the cleaning catheter, in a proximal to distal direction, into the ventilation tube inserted in a trachea of a patient, and advancing the cleaning catheter until a distal end of the catheter main body is axially disposed in the ventilation tube at a location more distal than an axial mid-point of the ventilation tube.

For some applications, the input module is arranged such that the linking element, when in its first spatial position, prevents the transition of the mechanical inflation-control button from its first spatial position to its second spatial position.

For some applications, the input module is arranged such that transitioning of the linking element from its first spatial position to its second spatial position simultaneously (a) unlocks the mechanical inflation-control button from its first spatial position, and (b) links the mechanical suction-control button with the mechanical inflation-control button.

There is still further provided, in accordance with an application of the present invention, a method for use with a tracheal ventilation tube and a suction source, the method including:

providing a cleaning catheter, which is insertable into the ventilation tube and includes (i) an elongate, flexible, tubular catheter main body, which is shaped so as to define (a) one or more distal suction orifices, (b) a suction lumen, and (c) an inflation lumen; and (ii) an inflatable element, which is mounted to the catheter main body;

providing an input module, which is coupled to the cleaning catheter, and includes (i) an inflation module, which includes an inflation chamber, wherein the inflation lumen couples an interior of the inflation chamber in fluid communication with an interior of the inflatable element; (ii) a flow regulator, which is shaped so as to define a suction port coupleable in fluid communication with the suction source; (iii) a mechanical suction-control button, which is configured to assume at least first and second spatial positions; (iv) a mechanical inflation-control button, which is configured to (a) assume at least first and second spatial positions, and (b) mechanically and non-electrically increase pressure in the interior of the inflation chamber during a transition of the mechanical inflation-control button from its first spatial position to its second spatial position; and (v) a reversibly-engageable linking element, which is moveable with respect to the mechanical suction-control button and the mechanical inflation-control button, and is configured to assume at least first and second spatial positions, wherein the input module is arranged such that: (A) at least when the mechanical suction-control button is in its first spatial position, the flow regulator blocks fluid communication between the suction source and the distal suction orifices, and at least when the mechanical suction-control button is in its second spatial position, the flow regulator connects the suction source and the distal suction orifices in fluid communication via the suction lumen, (B) when (a) the linking element is in its first spatial position and (b) the mechanical suction-control button and the mechanical inflation-control button are in their respective first spatial positions: depression of the linking element does not transition the mechanical inflation-control button to its second spatial position, and (C) when (a) the linking element is in its second spatial position and (b) the mechanical suction-control button and the mechanical inflation-control button are in their respective first spatial positions: depression of the linking element transitions the mechanical inflation-control button to its second spatial position;

coupling the suction portion in fluid communication with the suction source; and inserting the cleaning catheter, in a proximal to distal direction, into the ventilation tube inserted in a trachea of a patient, and advancing the cleaning catheter until a distal end of the catheter main body is axially disposed in the ventilation tube at a location more distal than an axial mid-point of the ventilation tube.

There is additionally provided, in accordance with an application of the present invention, a method for use with a tracheal ventilation tube and a suction source, the method including:

providing a cleaning catheter, which is insertable into the ventilation tube and includes (i) an elongate, flexible, tubular catheter main body, which is shaped so as to define (a) one or more distal suction orifices, (b) a suction lumen, and (c) an inflation lumen; and (ii) an inflatable element, which is mounted to the catheter main body;

providing an input module, which is coupled to the cleaning catheter, and includes: (i) an inflation module, which includes an inflation chamber, wherein the inflation lumen couples an interior of the inflation chamber in fluid communication with an interior of the inflatable element; (ii) a flow regulator, which is shaped so as to define a suction port coupleable in fluid communication with the suction source; (iii) a mechanical suction-control button, which is configured to assume at least first and second spatial positions; (iv) a mechanical inflation-control button, which is configured to (a) assume at least first and second spatial positions, and (b) mechanically and non-electrically increase pressure in the interior of the inflation chamber during a transition of the mechanical inflation-control button from its first spatial position to its second spatial position; and (v) exactly one spring that is arranged to bias both the mechanical suction-control button and the mechanical inflation-control button toward their respective first spatial positions, wherein the input module is arranged such that (a) at least when the mechanical suction-control button is in its first spatial position, the flow regulator blocks fluid communication between the suction source and the distal suction orifices, and (b) at least when the mechanical suction-control button is in its second spatial position, the flow regulator connects the suction source and the distal suction orifices in fluid communication via the suction lumen;

coupling the suction portion in fluid communication with the suction source; and inserting the cleaning catheter, in a proximal to distal direction, into the ventilation tube inserted in a trachea of a patient, and advancing the cleaning catheter until a distal end of the catheter main body is axially disposed in the ventilation tube at a location more distal than an axial mid-point of the ventilation tube.

There is yet additionally provided, in accordance with an application of the present invention, a method for use with a tracheal ventilation tube and a suction source, the method including:

providing a cleaning catheter, which is insertable into the ventilation tube and includes (i) an elongate, flexible, tubular catheter main body, which is shaped so as to define (a) one or more distal suction orifices, (b) a suction lumen, and (c) an inflation lumen; and (ii) an inflatable element, which is mounted to the catheter main body;

providing an input module, which is coupled to the cleaning catheter, and includes (i) an inflation module, which includes an inflation chamber, wherein the inflation lumen couples an interior of the inflation chamber in fluid communication with an interior of the inflatable element; (ii) a flow regulator, which is shaped so as to define a suction port coupleable in fluid communication with the suction source; (iii) a mechanical suction-control button, which is configured to assume at least first, second, and third spatial positions, the second spatial position between the first and the third spatial positions; (iv) a mechanical inflation-control button, which (a) is not shaped so as to define a user interface surface, (b) is configured to assume at least first and second spatial positions, and (c) is configured to mechanically and non-electrically increase pressure in the interior of the inflation chamber during a transition of the mechanical inflation-control button from its first spatial position to its second spatial position; (v) a reversibly-engageable linking element, which is fixed to the mechanical suction-control button, and is configured to assume at least first, second, and third spatial positions, the second spatial position between the first and the third spatial positions; and (vi) a cover, which is arranged to inhibit user access to the mechanical inflation-control button, wherein the input module is arranged such that: (a) at least when the mechanical suction-control button is in its first spatial position, the flow regulator blocks fluid communication between the suction source and the distal suction orifices, and at least when the mechanical suction-control button is in its second and third spatial positions, the flow regulator connects the suction source and the distal suction orifices in fluid communication via the suction lumen, (b) a first transition of the mechanical suction-control button from its first spatial position to its second spatial position causes a second transition of the linking element from its first spatial position to its second spatial position, and (c) a third transition of the mechanical suction-control button from its second spatial position to its third spatial position causes a fourth transition of the linking element from its second spatial position to its third spatial position, which in turn causes a fifth transition of the mechanical inflation-control button to its second spatial position;

coupling the suction portion in fluid communication with the suction source; and inserting the cleaning catheter, in a proximal to distal direction, into the ventilation tube inserted in a trachea of a patient, and advancing the cleaning catheter until a distal end of the catheter main body is axially disposed in the ventilation tube at a location more distal than an axial mid-point of the ventilation tube.

There is also provided, in accordance with an application of the present invention, a method for use with a tracheal ventilation tube and a suction source, the method including:

providing a cleaning catheter, which is insertable into the ventilation tube and includes: (i) an elongate, flexible, tubular catheter main body, which is shaped so as to define (a) one or more distal suction orifices, (b) a suction lumen, and (c) an inflation lumen; and (ii) an inflatable element, which is mounted to the catheter main body;

providing an input module, which is coupled to the cleaning catheter, and includes (i) an inflation module, which includes an inflation chamber, wherein the inflation lumen couples an interior of the inflation chamber in fluid communication with an interior of the inflatable element; (ii) a flow regulator, which is shaped so as to define a suction port coupleable in fluid communication with the suction source; (iii) a mechanical suction-control button, which is configured to assume at least first, second, and third spatial positions, the second spatial position between the first and the third spatial positions; (iv) a mechanical inflation-control button, which (a) is not shaped so as to define a user interface surface, (b) is configured to assume at least first and second spatial positions, and (c) is configured to mechanically and non-electrically increase pressure in the interior of the inflation chamber during a transition of the mechanical inflation-control button from its first spatial position to its second spatial position; (v) a reversibly-engageable linking element, which is fixed to the mechanical suction-control button, and is configured to assume at least: (a) a first spatial position, in which the linking element does not engage the mechanical inflation-control button, (b) a second spatial position, and (c) a third spatial position, in which the linking element engages the mechanical inflation-control button, wherein the second spatial position is between the first and the third spatial positions; and (vi) a moveable stopper, which is moveably fixed to the input module, and which is configured to assume at least: (a) a first spatial position, in which the moveable stopper blocks a first transition of the linking element from its second spatial position to its third spatial position, and (b) a second spatial position, in which the moveable stopper does not block the first transition of the linking element from its second spatial position to its third spatial position, wherein the input module is arranged such that: (A) at least when the mechanical suction-control button is in its first spatial position, the flow regulator blocks fluid communication between the suction source and the distal suction orifices, and at least when the mechanical suction-control button is in its second and third spatial positions, the flow regulator connects the suction source and the distal suction orifices in fluid communication via the suction lumen, and (B) when (a) the linking element is in its second spatial position, (b) the mechanical suction-control button is in its second spatial position, (c) the mechanical inflation-control button is in its first spatial position, and (d) the moveable stopper is in its second spatial position: depression of the mechanical control button causes a second transition of the mechanical suction-control button to its third spatial position, which second transition, via the linking element, causes a third transition of the mechanical inflation-control button to its second spatial position;

coupling the suction portion in fluid communication with the suction source; and inserting the cleaning catheter, in a proximal to distal direction, into the ventilation tube inserted in a trachea of a patient, and advancing the cleaning catheter until a distal end of the catheter main body is axially disposed in the ventilation tube at a location more distal than an axial mid-point of the ventilation tube.

There is further provided, in accordance with an application of the present invention, a method for use with a tracheal ventilation tube, the method including:

providing a cleaning catheter, which is insertable into the ventilation tube and includes (i) an elongate, flexible, tubular catheter main body, which is shaped so as to define (a) one or more distal suction orifices, and (b) an inflation lumen; and (ii) an inflatable element, which is mounted to the catheter main body;

providing an input module, which is coupled to the cleaning catheter, and includes (i) an inflation module, which includes an inflation chamber, wherein the inflation lumen couples an interior of the inflation chamber in fluid communication with an interior of the inflatable element; (ii) a mechanical inflation-control button, which is configured to (a) assume at least a deflation-inducing spatial position, a first spatial position, and a second spatial positions, the first spatial position between the deflation-inducing spatial position and the second spatial position, and (b) mechanically and non-electrically increase pressure in the interior of the inflation chamber during transition of the mechanical inflation-control button from its deflation-inducing spatial position to its first spatial position, and from its first spatial position to its second spatial position; and (iii) a mechanical deflation-control button, which is arranged such that when the mechanical inflation-control button is in its first spatial position, depression of the mechanical deflation-control button transitions the mechanical inflation-control button from its first spatial position to its deflation-inducing spatial position, thereby deflating the inflatable element;

coupling the suction portion in fluid communication with the suction source; and inserting the cleaning catheter, in a proximal to distal direction, into the ventilation tube inserted in a trachea of a patient, and advancing the cleaning catheter until a distal end of the catheter main body is axially disposed in the ventilation tube at a location more distal than an axial mid-point of the ventilation tube.

The present invention will be more fully understood from the following detailed description of embodiments thereof, taken together with the drawings, in which:

DETAILED DESCRIPTION OF APPLICATIONS

Figure 1A:
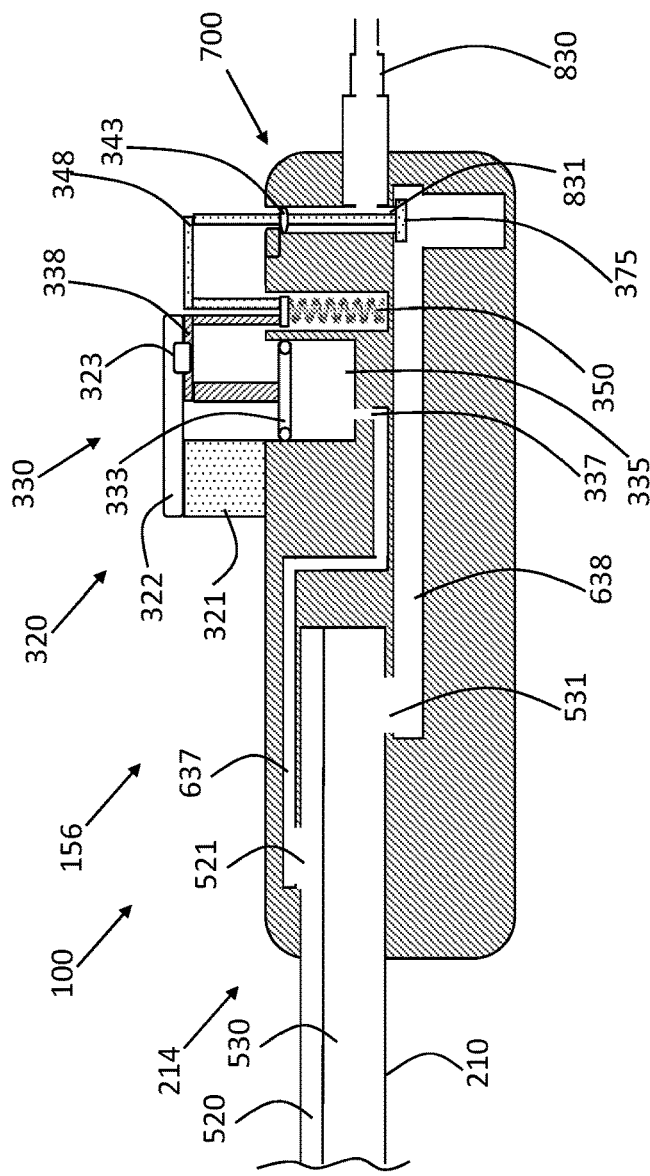
FIGS. 1A-D are schematic cross-sectional illustrations of one configuration of a closed suction cleaning system in respective states, in accordance with an application of the present invention.
Figure 1A:
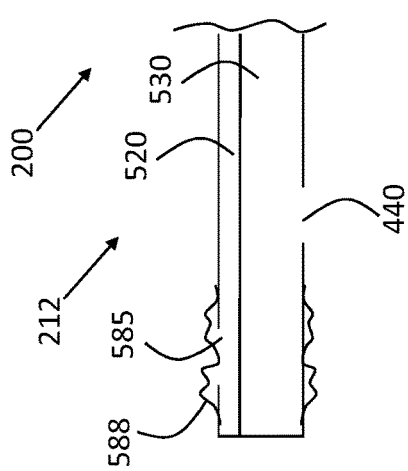

The figures are schematic cross-sectional illustrations of several configurations of a closed suction cleaning system 100, in accordance with respective applications of the present invention. Cleaning system 100 is typically configured for use with a tracheal ventilation tube, a ventilator, and a suction source. For some applications, cleaning system 100 comprises one or more of the tracheal ventilation tube, the ventilator, and/or the suction source, in any combination. Although these elements are not illustrated in the figures, they can be seen in FIGS. 1A-D of U.S. Pat. No. 8,999,074 to Zachar et al., which is incorporated herein by reference. Cleaning system 100 may be implemented as shown in FIGS. 1A-D of the '074 patent, mutatis mutandis, except that cleaning system 100 typically does not comprise the pressurized fluid source 602 shown in these figures.

As used in the present application, including in the claims, a "tracheal ventilation tube" comprises an endotracheal tube (ETT) or a tracheostomy tube. For some applications, the suction source provides a pressure less than one atm; alternatively or additionally, for some applications, the suction source provides a pressure lower than ambient pressure. As used in the present application, including in the claims, a "fluid" comprises liquid and/or gas, for example, a liquid-gas mixture that is predominantly liquid, such as a liquid with gas bubbles. The liquid may comprise water, such as saline solution or a disinfectant solution.

Cleaning system 100 typically comprises a distal ventilation tube-connector assembly (labeled with reference numeral 158 in FIGS. 1A-D of the '074 patent), a cleaning catheter 200, and an input module 156. Cleaning catheter 200 comprises an elongate, flexible, tubular catheter main body 210. Cleaning catheter 200 includes a distal portion 212 located distal to the ventilation tube-connector assembly, and a proximal portion 214 located proximal to the ventilation tube-connector assembly. Distal portion 212 is configured to be inserted into the ventilation tube. Proximal portion 214 includes a proximal-most input portion of catheter main body 210, which is configured to be inserted into or is disposed within input module 156. Typically, the proximal-most input portion is fixed with respect to input module 156. Respective lengths of distal and proximal portions 212 and 214 may depend on an extent to which a distal end of catheter main body 210 is deployed within the ventilation tube and/or an extent to which the distal end is longitudinally displaced from the ventilation tube-connector assembly, for example, an extent to which catheter main body 210 slides through the ventilation tube-connector assembly in a distal direction.

As used in the present application, including in the claims, "axial" and "axially" mean along an axis, and do not mean around or about an axis. For example: (a) "axial motion" means motion along an axis, and (b) "axially aligned" means aligned along an axis.

The ventilation tube-connector assembly comprises: (a) a ventilator port (labeled with reference numeral 664 in FIGS. 1A-D of the '074 patent), configured to be coupled in fluid communication with the ventilator via a ventilator connection tube (labeled with reference numeral 910 in FIGS. 1A-D of the '074 patent), (b) a ventilation tube port (labeled with reference numeral 660 in FIGS. 1A-B and 1D of the '074 patent), configured to be coupled in fluid communication with a proximal end of the ventilation tube, and (c) a main body inlet, which is configured to allow passage therethrough of catheter main body 210.

In some applications of the present invention, cleaning system 100 is operative to clean an interior of the ventilation tube when the ventilation tube-connector assembly is directly or indirectly connected to both the ventilation tube and the ventilator so as to mediate a substantially air-tight connection (e.g., via an interior chamber(s) and/or conduit(s) of the ventilation tube-connector assembly) between the ventilator and an interior of the ventilation tube.

Cleaning catheter 200 further comprises an inflatable element 588, such as a balloon, which is mounted to catheter main body 210 near a distal end of catheter main body 210, e.g., within 3 cm, such as within 1 cm, of the distal end, and/or in a distal half of distal portion 212 of cleaning catheter 200, such as a distal third, a distal fifth, or a distal tenth of distal portion 212. Alternatively or additionally, inflatable element 588 is mounted to catheter main body 210 within 3 cm, e.g., within 1 cm, of at least one of the one or more distal suction orifices 440, described hereinbelow. Inflatable element 588 is inflatable into contact with an inner surface of the ventilation tube. For some applications, inflatable element 588 has a greatest outer diameter of at least 6 mm, no more than 12 mm, and/or between 6 and 12 mm when inflated at 1 bar above atmospheric pressure and unconstrained (i.e., not constrained by the ventilation tube or anything else), which is typically slightly greater than an inner diameter of the ventilation tube, in order to provide sealing contact with the inner surface of the ventilation tube. For some applications, inflatable element 588 has a volume of at least 0.5 cc, no more than 2 cc, and/or between 0.5 and 2 cc when inflated at 1 bar above atmospheric pressure and unconstrained. For some applications, inflatable element 588 is elastic, while for other applications inflatable element 588 is not elastic. For some applications, inflatable element 588 comprises a thin pliable material, such that the inflatable element crumples when deflated.

For some applications, catheter main body 210 has an outer diameter of at least 6 mm, no more than 12 mm, and/or between 6 and 12 mm. For some applications, the greatest outer diameter of inflatable element 588 when fully inflated and unconstrained (i.e., not constrained by the ventilation tube or anything else) equals at least 60%, no more than 120%, and/or between 60% and 120% of the outer diameter of catheter main body 210.

Reference is again made to all of the figures. Catheter main body 210 typically includes at least the following lumens arranged along catheter main body 210. For some applications, one or more of the lumens are arranged along catheter main body 210 at least partially within the main body, e.g., integrally formed in the catheter main body 210, formed in the wall of catheter main body 210, or provided as a separate tube with catheter main body 210. Alternatively or additionally, one or more of the lumens are arranged along catheter main body 210 at least partially outside the main body, e.g., provided as a separate tube outside catheter main body 210. The lumens typically include:

- at least one inflation lumen 520, which provides fluid communication between at least one inflation inlet 521 and at least one inflation port 585 which is in fluid communication with an interior of inflatable element 588; typically, the input portion is shaped so as to define inflation inlet 521, and distal portion 212 is shaped so as to define inflation port 585; and
- at least one suction lumen 530, which provides fluid communication between at least one proximal suction inlet 531 and the one or more distal suction orifices 440; typically, the input portion of catheter main body 210 is shaped so as to define proximal suction inlet 531, and distal portion 212 of cleaning catheter 200 is shaped so as to define distal suction orifices 440. The at least one suction lumen 530 is arranged in intermittent fluid communication with the suction source, as described in detail hereinbelow.

Inflation lumen 520 typically has a cross-sectional area smaller than that of suction lumen 530, e.g., less than 50%, less than 30%, or less than 20% of the cross-sectional area of suction lumen 530.

When inflated, inflatable element 588 typically provides two types of functionality: (i) flow obstruction functionality to significantly hinder fluid flow between locations on opposite longitudinal sides of the inflatable element, and/or (ii) wiping functionality useful for cleaning the inner surface of the ventilation tube. Typically, cleaning system 100 operates in a closed system environment.

During one state of operation, cleaning system 100 cleans the inner surface of the ventilation tube when the ventilation tube-connector assembly mediates a substantially air-tight seal between (i) the ventilator and/or an interior of the ventilator port and (ii) an interior of the ventilation tube and/or an interior of the ventilation tube port.

Concurrently with maintaining of this ventilation machine-ventilator tube seal, inflatable element 588 may be positioned within the ventilation tube (e.g., in a distal portion of the ventilation tube), for example by moving a distal end of catheter main body 210 in a distal direction towards a distal end of the ventilation tube. For example, inflatable element 588 may be distally advanced when inflatable element 588 is in a non-contact state (i.e., not in contact with the inner surface of the ventilation tube). After inflatable element 588 is thus positioned, inflation of the inflatable element induces contact between an outer surface of inflatable element 588 and the inner surface of the ventilation tube and/or obstructs (i.e., significant hinders) longitudinal flow between proximal and distal portions of the interior of the ventilation tube.

Upon inflation of inflatable element 588 when the inflatable element is positioned within the ventilation tube, the inflated inflatable element forms a sliding boundary which obstructs (i.e., significantly hinders) fluid flow to between: (a) a more proximal portion of an interstitial region outside of catheter main body 210 and within the ventilation tube and (b) locations within the ventilation tube that are distal to the slidable boundary formed and delineated by inflatable element 588. This slidable boundary between the proximal and distal portions may be useful for facilitating the cleaning of the inner surface of the ventilation tube (by wiping), for example for substantially confining locations of negative pressure and/or fluid (e.g., pressurized fluid) introduced into an interstitial region outside of catheter main body 210 and within the ventilation tube so that the suction is introduced predominantly in the proximal portion of the ventilation tube.

Distal portion 212 of cleaning catheter 200 is shaped so as to define one or more distal suction orifices 440, typically through a lateral wall of distal portion 212. Typically, the one or more distal suction orifices 440 are located along distal portion 212 at one or more respective locations proximal to inflatable element 588. Typically, at least one of distal suction orifices 440 (such as all of the one or more distal suction orifices 440) is located within 1 cm of inflatable element 588, such as within 0.8 cm, e.g., within 0.5 cm of the inflatable element. For some applications, distal suction orifices 440 have a total cross-sectional area in aggregate of at least 2 mm2, no more than 25 mm2, and/or between 2 and 25 mm2, such as at least 4 mm2, no more than 16 mm2, and/or between 4 and 16 mm2.

Distal suction orifices 440 are supplied with negative pressure by the suction source and facilitate cleaning of the inner surface of the ventilation tube. For some applications, material within the interior of the ventilation tube may be suctioned into distal suction orifices 440 and proximally transported out of the ventilation tube, e.g., to a location that is proximal to the ventilation tube-connector assembly. As described below in detail, fluid communication between the suction source and distal suction orifices 440 may be provided by one or more connecting lumens within or along catheter main body 210. As used in the present application, including in the claims, "fluid communication" includes both positive and negative pressure fluid communication, and thus includes, for example, communication of a positive pressure or of a suction force.

For some applications, cleaning system 100 comprises a substantially impermeable and/or pliable sleeve (labeled with reference numeral 610 in FIGS. 1A-D of the '074 patent) for protecting an outer surface of catheter main body 210. In some embodiments, the sleeve envelops, surrounds, and/or protects at least some (e.g., at least a majority or at least a substantial majority, e.g., at least 75% or substantially all of (e.g., at least 90%)) of an outer surface of a ventilation-tube-connector-assembly-proximal portion of catheter main body 210, typically in locations proximal to the tube-connector assembly and distal to suction port 830 (described hereinbelow), and typically to inhibit contamination. For some applications, the sleeve provides this enveloping and/or protection functionality when a length of the ventilation-tube-connector-assembly-proximal portion of catheter main body 210 is at least 5 cm, e.g., at least 10 cm, at least 15 cm, or at least 20 cm.

For some applications, a length of proximal portion 214 may be modified by sliding, in a proximal or distal direction, catheter main body 210 through the ventilation tube-connector assembly.

For some applications, a distal end of the sleeve is (i) directly or indirectly attached to and/or (ii) has a location that is fixed and/or longitudinally fixed relative to the ventilation tube-connector assembly. For some applications, a longitudinal position of a location of the distal end of the sleeve corresponds to a location on the ventilation tube-connector assembly (e.g., at or near the main body inlet) and/or is longitudinally displaced from a proximal end (e.g., corresponding to the main body inlet) of the ventilation tube-connector assembly by at most 5 cm, e.g., at most 3 cm, at most 2 cm, or at most 1 cm, and/or at most 50%, e.g., at most 30%, at most 20%, at most 10% of a length of ventilation-tube-connector-assembly-proximal portion 214 of catheter main body 210.

For some applications, a location of the distal end of the sleeve is not fixed relative to catheter main body 210. For example, catheter main body 210 may be longitudinally slidable within the sleeve at or near a location of the distal end. Alternatively or additionally, for some applications, a location of a proximal end of the sleeve is fixed and/or longitudinally fixed relative to a proximal end of catheter main body 210. For some applications, the sleeve forms a substantially air-tight seal between the external environment and an outer surface of the ventilation-tube-connector-assembly-proximal portion of catheter main body 210 and/or between the external environment and region of space outside of an outer surface of the ventilation-tube-connector-assembly-proximal portion of catheter main body 210 and within the sleeve.

Reference is now made to FIGS. 1A-D, which are schematic cross-sectional illustrations of one configuration of closed suction cleaning system 100 in respective states, in accordance with an application of the present invention. As mentioned above, in some configurations input portion 216 of proximal portion of catheter main body 210 is configured to be inserted into or is disposed within, and axially slidable with respect to, input module 156.

Input module 156 is coupled to cleaning catheter 200, and comprises:
  an inflation module 330, which comprises an inflation chamber 335 (typically separate from the suction source);
  a flow regulator 700, which is (a) shaped so as to define suction port 830, which is coupleable in fluid communication with the suction source, and coupled in fluid communication with the suction source during use of cleaning system 100;
  a mechanical user control assembly 320, which is configured to mechanically and non-electrically set fluid-control states of flow regulator 700; and
  typically, a housing encasing input portion 216 of catheter main body 210.

For some applications, input module 156 comprises exactly one mechanical user control assembly 320 having the properties described herein, and/or system 100 comprises exactly one mechanical user control assembly 320 having the properties described herein. Input module 156 and/or system 100 may comprise further user control elements that perform control functions in addition to those performed by mechanical user control assembly 320.

Figure 1B:
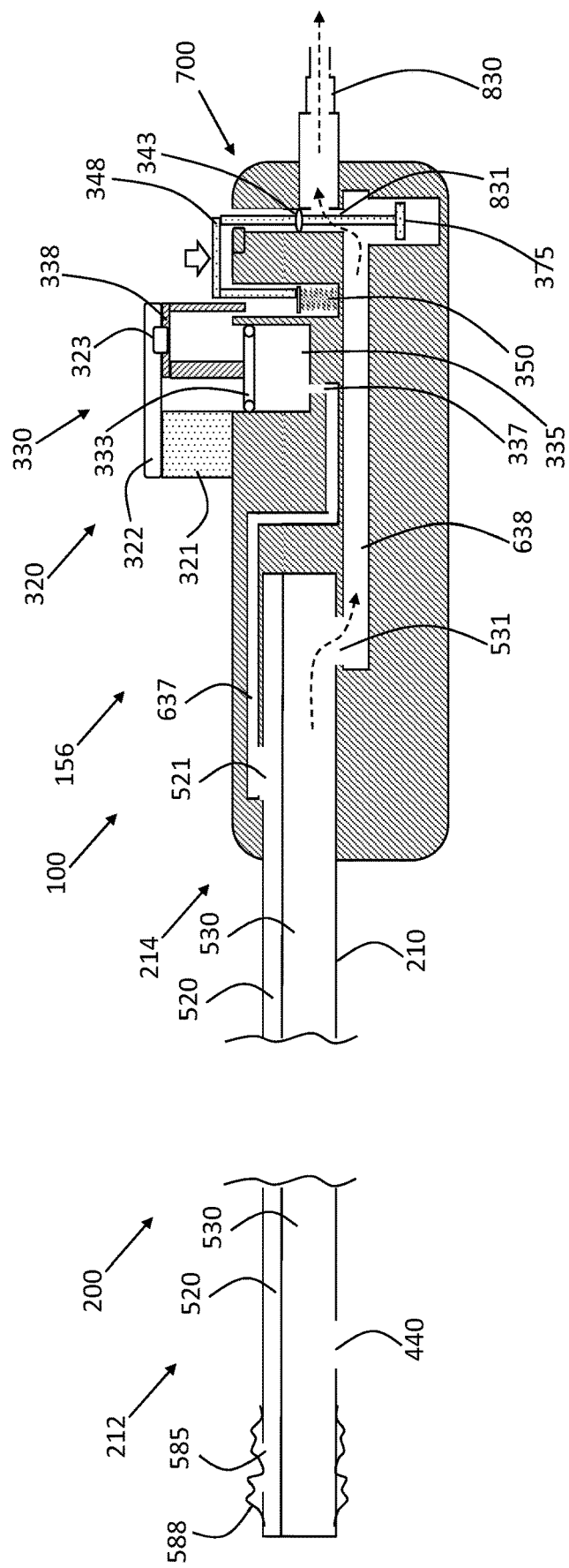
Figure 1C:
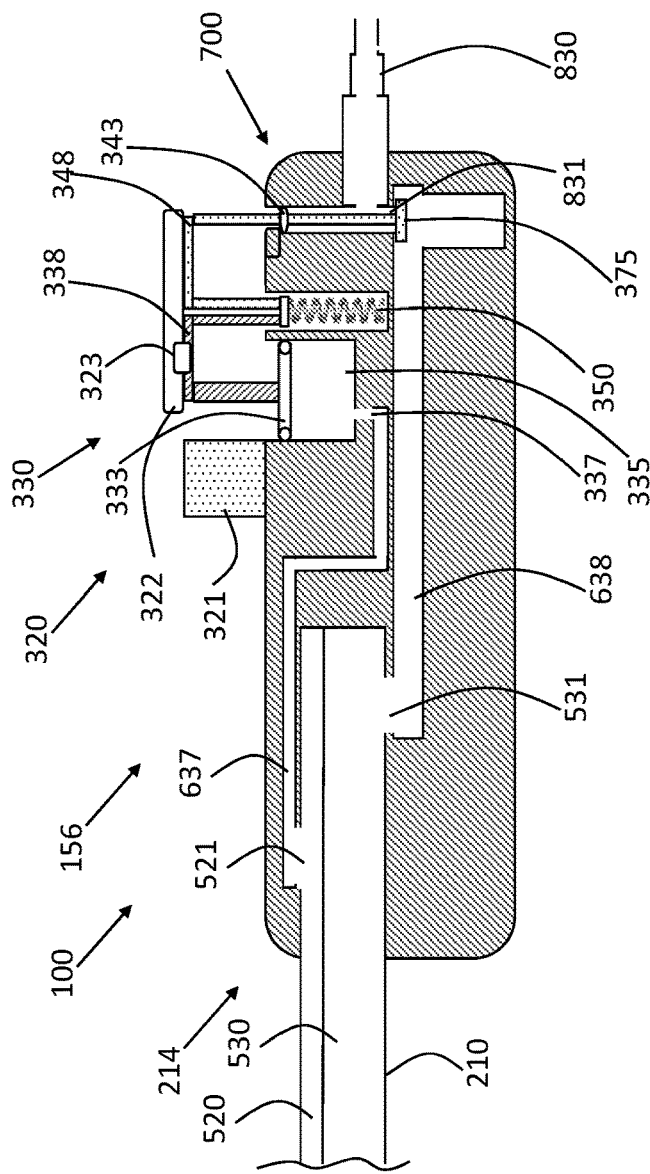
Figure 1C:
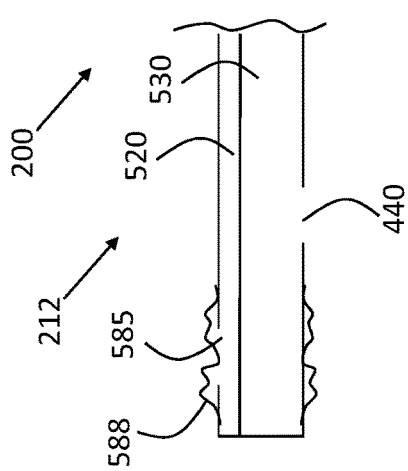
Figure 1D:
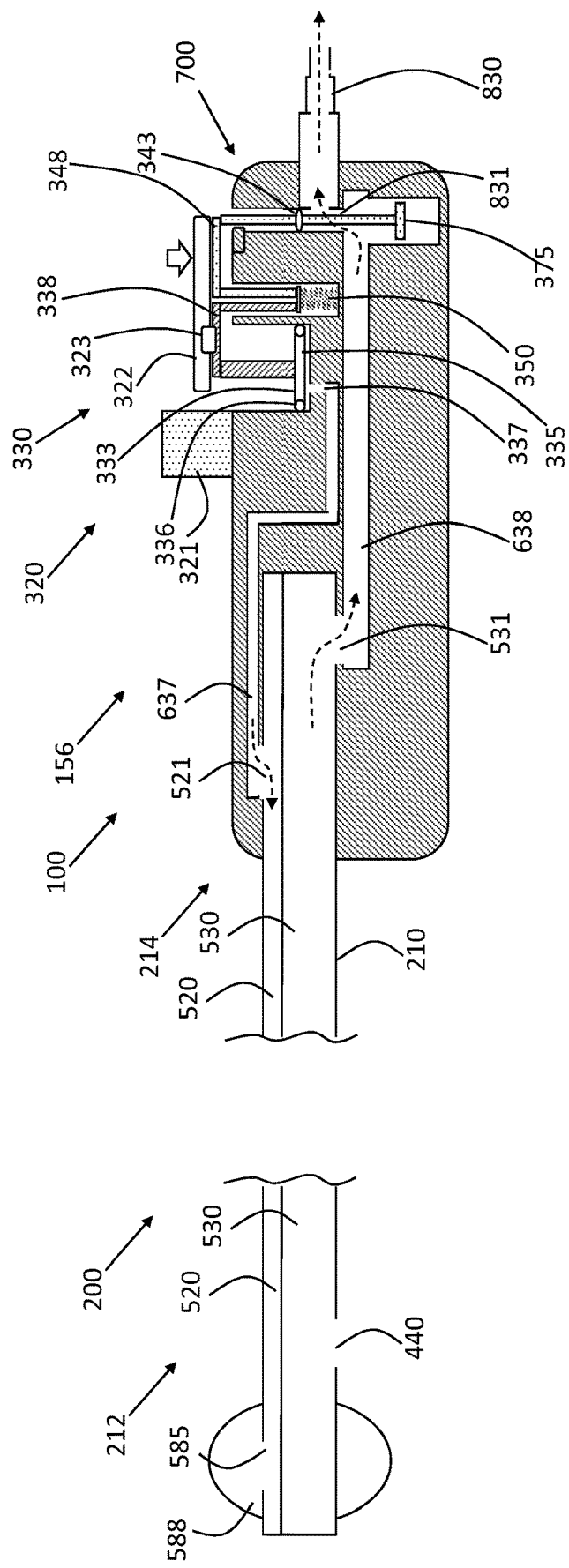

Input module 156 (mechanical user control assembly 320 thereof) comprises:
  a mechanical suction-control button 348, which is configured to assume at least a first spatial position (as shown in FIGS. 1A and 1C) and a second spatial position (as shown in FIGS. 1B and 1D);
  a mechanical inflation-control button 338, which is configured to (a) assume at least a first spatial position (as shown in FIGS. 1A, 1B, and 1C) and a second spatial position (as shown in FIG. 1D), and (b) mechanically and non-electrically increase pressure in the interior of inflation chamber 335 during a transition of mechanical inflation-control button 338 from its first spatial position to its second spatial position (i.e., inflation chamber 335 functions as a compression pump); and
  a reversibly-engageable linking element 322, which is moveable with respect to mechanical suction-control button 348 and mechanical inflation-control button 338 (as well as with respect to other elements of input module 156, such as suction port 830 and the housing), and is configured to assume at least (a) a first spatial position (as shown in FIGS. 1A and 1B), in which linking element 322 does not engage mechanical suction-control button 348 when mechanical suction-control button 348 is in its second spatial position (and, optionally, prevents the transition of mechanical inflation-control button 338 from its first spatial position to its second spatial position), and (b) a second spatial position (as shown in FIGS. 1C and 1D).

Reversibly-engageable linking element 322 is arranged to be bidirectionally moveable between its first and second spatial positions and vice versa.

Typically, linking element 322 is shaped so as to define a linking user interface surface, at least a portion (e.g., at least 1 cm2) of which is visible from outside input module 156, and is accessible by a finger of a user from outside input module 156.

Input module 156 is arranged such that:
  at least when mechanical suction-control button 348 is in its first spatial position, as shown in FIGS. 1A and 1C, flow regulator 700 blocks fluid communication between the suction source and distal suction orifices 440, and at least when mechanical suction-control button 348 is in its second spatial position, as shown in FIGS. 1B and 1D, flow regulator 700 connects the suction source and distal suction orifices 440 in fluid communication via suction lumen 530, and when, as shown in FIG. 1C, (a) linking element 322 is in its second spatial position and (b) mechanical suction-control button 348 and mechanical inflation-control button 338 are in their respective first spatial positions: depression of linking element 322 transitions both mechanical suction-control button 348 and mechanical inflation-control button 338 to their respective second spatial positions, as shown in FIG. 1D, typically such that linking element 322 engages both mechanical suction-control button 348 and the mechanical inflation-control button 338 at least when mechanical suction-control button 348 is in its second spatial position (and typically also when mechanical suction-control button 348 is in its first spatial position).

For some applications, input module 156 is shaped so as to define (a) a suction channel 831, which is in fluid communication with suction port 830, and (b) a plug 375. Mechanical suction-control button 348 is arranged to move plug 375 to block or open suction channel 831. Input module 156 may also comprise a plug 343, which prevents leakage to outside of the input module.

For some applications, input module 156 is arranged such that when linking element 322 is in its first spatial position, such as shown in FIGS. 1A and 1B, linking element 322:
  locks mechanical inflation-control button 338 in the first spatial position of mechanical inflation-control button 338, and (b) does not lock mechanical suction-control button 348 (for example, input module 156 may comprise a stopper 321 that prevents motion of linking element 322 in the direction of motion of mechanical inflation-control button 338),
  does not prevent user access to mechanical suction-control button 348,
  does not engage mechanical suction-control button 348,
  engages mechanical inflation-control button 338, and/or
  is not arranged to transition mechanical suction-control button 348 all the way to its second spatial position.

Alternatively or additionally, for some applications, input module 156 is arranged such that when (a) linking element 322 is in its second spatial position and (b) mechanical suction-control button 348 and mechanical inflation-control button 338 are in their respective first spatial positions: the depression of linking element 322 simultaneously transitions both mechanical suction-control button 348 and mechanical inflation-control button 338 to their respective second spatial positions.

Alternatively or additionally, for some applications, input module 156 is arranged such that transitioning of linking element 322 from its first spatial position to its second spatial position simultaneously (a) unlocks the mechanical inflation-control button 338 from its first spatial position, and (b) links the mechanical suction-control button 348 with mechanical inflation-control button 338.

For some applications, such as shown in FIGS. 1A-D, the first and the second spatial positions of linking element 322 are first and second axial positions, and linking element 322 is configured to assume at least the first and the second axial positions. Alternatively or additionally, for some applications, such as shown in FIGS. 1A-D, (a) the first and the second spatial positions of mechanical suction-control button 348 are first and second radial positions, and mechanical suction-control button 348 is configured to assume at least the first and the second radial positions, and/or (b) the first and the second spatial positions of mechanical inflation-control button 338 are first and second radial positions, and mechanical inflation-control button 338 is configured to assume at least the first and the second radial positions. For some applications, linking element 322 is arranged to axially slide between its first and second spatial positions. Alternatively or additionally, for some applications, linking element 322 is arranged to rotate between its first and second spatial positions.

For some applications, mechanical suction-control button 348 is disposed proximally (to the right in the figures) to mechanical inflation-control button 338. Such an arrangement may provide better ergonomic access to the user.

For some applications, such as shown in FIGS. 1A-D, linking element 322 is moveably attached to mechanical inflation-control button 338; in other words, linking element 322 is attached to mechanical inflation-control button 338 in a manner that allows movement of mechanical inflation-control button 338. For example, linking element 322 may be attached to mechanical inflation-control button 338 by tracks 323.

Typically, mechanical suction-control button 348, mechanical inflation-control button 338, and reversibly-engageable linking element 322 are able to assume respective infinite numbers of spatial positions between their respective first and second spatial positions, as these buttons and element transition between their respective first and second spatial positions and vice versa. For some applications, mechanical suction-control button 348, mechanical inflation-control button 338, and reversibly-engageable linking element 322 are arranged to move between respective first and second spatial end-points, and the respective first and the second spatial positions correspond with the respective first and the second spatial end-points, respectively. Alternatively, the respective first and the second spatial positions do not correspond with the first and the second spatial end-points, respectively (such as described hereinbelow with reference to FIGS. 7A-D), but instead the respective first spatial positions and/or the second spatial positions are between the respective first and the second spatial end-points.

Input module 156 is typically arranged such that flow regulator 700 blocks fluid communication between blocks fluid communication between the suction source and distal suction orifices 440 not only when mechanical suction-control button 348 is in its first spatial position, as shown in FIGS. 1A and 1C, but also during a portion of the intermediate spatial positions, which are typically contiguous with the first spatial position. Similarly, input module 156 is typically arranged such that flow regulator 700 connects the suction source and distal suction orifices 440 in fluid communication not only when mechanical suction-control button 348 is in its second spatial position, as shown in FIGS. 1B and 1D, but also during a portion of the intermediate spatial positions, which are typically contiguous with the second spatial position.

As mentioned above, mechanical inflation-control button 338 is configured to mechanically and non-electrically increase pressure in an interior of inflation chamber 335 during at least a portion of the transition of mechanical inflation-control button 338 from its first spatial position to its second spatial position. For some applications, mechanical inflation-control button 338 is configured to mechanically and non-electrically increase the pressure in the interior of inflation chamber 335 during an entirety of the transition of mechanical inflation-control button 338 from the its first spatial position to its second spatial position.

For some applications, mechanical suction-control button 348 and mechanical inflation-control button 338 are biased toward their respective first spatial positions. For some applications, input module 156 comprises one or more springs 350 that are arranged to bias mechanical suction-control button 348 and mechanical inflation-control button 338 toward their respective first spatial positions. For some applications, input module 156 comprises exactly one spring 350 that is arranged to bias both mechanical suction-control button 348 and mechanical inflation-control button 338 toward their respective first spatial positions. Providing a single spring to bias both mechanical suction-control button 348 and mechanical inflation-control button 338 causes the two buttons to provide uniform resistance to depression regardless of whether the healthcare worker depresses one or both of the buttons at a given time, and is thus ergonomically beneficial. For some applications, the one or more springs 350 are disposed outside inflation chamber 335. For example, at least a portion of one of the one or more springs 350 may be disposed alongside inflation chamber 335, such as parallel to an axis of motion of mechanical inflation-control button 338.

For some applications, inflation chamber 335 comprises (a) rigid lateral chamber walls, and (b) a moveable rigid compression wall 333 that forms an airtight seal with the rigid lateral chamber walls. Input module 156 is configured such that the transition of mechanical inflation-control button 338 from its first spatial position to its second spatial position moves moveable rigid compression wall 333 with respect to the rigid lateral chamber walls, thereby mechanically and non-electrically increasing the pressure in the interior of inflation chamber 335. For other applications, the configuration of cleaning system 100 shown in FIGS. 1A-D implements the configuration of inflation chamber 335 shown in FIGS. 3A-B, in which inflation chamber 335 comprises an elastic compartment 332, and input module 156 is configured such that the transition of mechanical inflation-control button 338 from its first spatial position to its second spatial position compresses elastic compartment 332, thereby mechanically and non-electrically increasing the pressure in an interior of elastic compartment 332.

For some applications, mechanical inflation-control button 338 is configured to increase the pressure in the interior of inflation chamber 335 by mechanically and non-electrically compressing inflation chamber 335 during the at least a portion of the transition of mechanical inflation-control button 338 from its first spatial position to its second spatial position. For some of these applications, inflation chamber 335 transitions from a lower level of compression to a higher level of compression during the at least a portion of the transition of mechanical inflation-control button 338 from its first spatial position to its second spatial position, and input module 156 is configured to elastically bias inflation chamber 335 toward the lower level of compression. For example, the inflation module may be elastically biased toward the lower level of compression, such as by the one or more springs 350 mentioned above.

For some applications, (a) mechanical suction-control button 348 is shaped so as to define a suction-control user interface surface, (b) mechanical inflation-control button 338 is not shaped so as to define a user interface surface, and (c) linking element 322 is shaped so as to define a linking user interface surface. Typically, at least 1 cm2 of the linking user interface surface is visible from outside input module 156, and is accessible by a finger of a user from outside input module 156. Input module 156 is arranged such that when (a) linking element 322 is in its first spatial position and (b) mechanical suction-control button 348 is in its first spatial position: (a) at least a portion (e.g., at least 1 cm2) of the suction-control user interface surface is visible from outside input module 156, and is accessible by a finger of a user from outside input module 156, and (b) depression of the suction-control user interface surface transitions mechanical suction-control button 348 to its second spatial position. Input module 156 is arranged such that when (a) linking element 322 is in its second spatial position and (b) mechanical suction-control button 348 and mechanical inflation-control button 338 are in their respective first spatial positions: depression of the linking user interface surface transitions both mechanical suction-control button 348 and mechanical inflation-control button 338 to their respective second spatial positions. Typically, input module 156 is arranged such that linking element 322, when in its second spatial position, blocks external access to the suction-control user interface surface.

For some applications, mechanical inflation-control button 338 is configured to additionally assume a deflation-inducing spatial position, and input module 156 further comprises a mechanical deflation-control button, such as described hereinbelow with reference to FIGS. 7A-D, mutatis mutandis.

Typically, suction port 830 is shaped as a conventional suction port in accordance with hospital standards for coupling to standard hospital suctions sources. For example, suction port 830 may have a male conical interface. Typically, suction port 830 has a lumen size that corresponds with the lumen size of conventional tracheal suction lumens, which generally having a gauge of between 5 Fr to 18 Fr.

For some applications, input module 156 further comprises a user signal generator, which is configured to generate a user signal (e.g., a sound) during at least a portion of a period of fluid flow into inflation chamber 335 and/or during or upon deflation of inflatable element 588. The user signal generator may be electrical and/or mechanical.

For some applications, inflation chamber 335 has a volume of at least 1 cc, no more than 10 cc, and/or between 1 and 10 cc (e.g., at least 1.5 cc, no more than 3 cc, and/or between 1.5 and 3 cc), when mechanical inflation-control button 338 is in its first spatial position (i.e., not compressed). The volume typically equals more than 1 times and less than 3 times the volume of inflatable element 588. Typically, when mechanical inflation-control button 338 is in its second spatial position (i.e., compressed), inflation chamber 335 has a volume of at least 1 cc less than when mechanical inflation-control button 338 is in its first spatial position (i.e., not compressed).

For suctioning the trachea, typically the following steps are performed:
  inserting cleaning catheter 200 into the ventilation tube in a proximal to distal direction while inflatable element 588 is essentially deflated and linking element 322 is in its first spatial position, such in the state shown in FIG. 1A; typically, in order to perform "deep suction," the distal end of the cleaning catheter is advanced beyond the distal end of the ventilation tube; and
  applying suction to the trachea by transitioning input module 156 to the state shown in FIG. 1B.

For cleaning a ventilation tube, the cleaning action typically comprises the following steps, which are typically performed in the following order (the healthcare worker typically does not perform the cleaning of the ventilation tube immediately after suctioning the trachea, as described above):
  inserting cleaning catheter 200 into the ventilation tube in a proximal to distal direction while inflatable element 588 is essentially deflated and linking element 322 is in its first spatial position, such in the state shown in FIG. 1A;

transitioning linking element 322 from its first spatial position as shown in FIG. 1A directly (i.e., not via the state shown in FIG. 1B) to its second spatial position, as shown in FIG. 1C;

applying suction and inflating inflatable element 588 at a location near the distal end of the ventilation tube by transitioning input module 156 to the state shown in FIG. 1D;

withdrawing the catheter along the ventilation tube in a distal to proximal direction while the inflatable element is inflated and suction is applied to the one or more suction orifices; and deflating the inflatable element when the inflatable element is near the proximal end of the ventilation tube or fully outside the proximal end of the ventilation tube, by transitioning input module 156 to the state shown in FIG. 1A.

For some applications, cleaning system 100 may also be used for suctioning the trachea outside of and distal to the ventilation tube, typically when flow regulator 700 is in one of the following states:

as shown in FIG. 1D, mechanical suction-control button 348 and mechanical inflation-control button 338 are in their respective second spatial positions, such that (a) the suction source and distal suction orifices 440 are in fluid communication, and (b) inflatable element 588 is inflated, or as shown in FIG. 1B, (a) mechanical suction-control button 348 is in its second spatial position, such that the suction source and distal suction orifices 440 are in fluid communication with one another, and (b) mechanical inflation-control button 338 is in its first spatial position, such that the interior of inflation chamber 335 and the interior of inflatable element 588 are not in fluid communication with one another, and inflatable element 588 is thus not inflated.

For some applications, the distal end of catheter main body 210 is closed (such as shown). In these applications, tracheal suction is typically performed by advancing catheter main body 210 far enough beyond the distal end of the ventilation tube such that at least one of the one or more distal suction orifices 440 is in fluid communication with the interior of the trachea distally beyond the end of the ventilation tube. For other applications, catheter main body 210 is shaped so as to define, in addition to the one or more distal suction orifices 440, a distal-most suction orifice at a distal end of distal portion 212 of cleaning catheter 200, distal to inflatable element 588, for example such as described in above-mentioned U.S. Pat. No. 8,999,074, with reference to FIGS. 21A-B and 22A-C thereof.

Reference is now made to FIGS. 2A-D, which are schematic cross-sectional illustrations of another configuration of closed suction cleaning system 100 in respective states, in accordance with an application of the present invention. Except as described hereinbelow, this configuration of cleaning system 100 may implement any of the features of the configuration of the system described hereinabove with reference to FIGS. 1A-D, mutatis mutandis.

In this configuration, cleaning system 100 comprises, rather than reversibly-engageable linking element 322, a reversibly-engageable linking element 324. Unlike in the configuration of cleaning system described hereinabove with reference to FIGS. 1A-D, in the present configuration mechanical suction-control button 348 typically covers a portion of linking element 324, i.e., is disposed radially outward and over the portion of linking element 324. Linking element 324 is typically visible and accessible to the user's finger at edges of the linking element that protrude laterally from under mechanical suction-control button 348 (i.e., in direction(s) out of and/or into the page in FIGS. 2A-D). Reversibly-engageable linking element 324 is arranged to be bidirectionally moveable between its first and second spatial positions and vice versa.

Figure 2A:
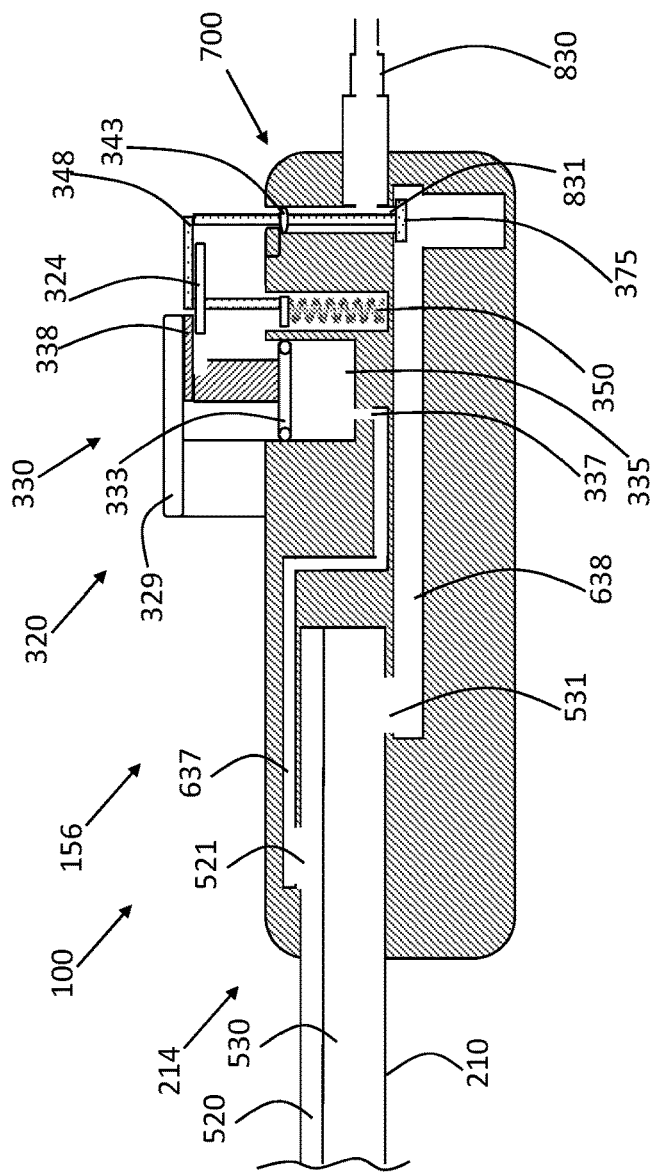
FIGS. 2A-D are schematic cross-sectional illustrations of another configuration of the closed suction cleaning system of FIGS. 1A-D in respective states, in accordance with an application of the present invention.
Figure 2A:
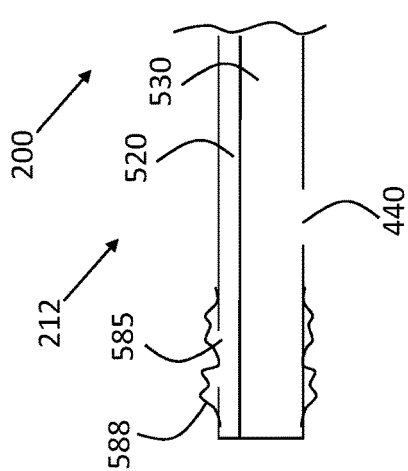
Figure 2B:
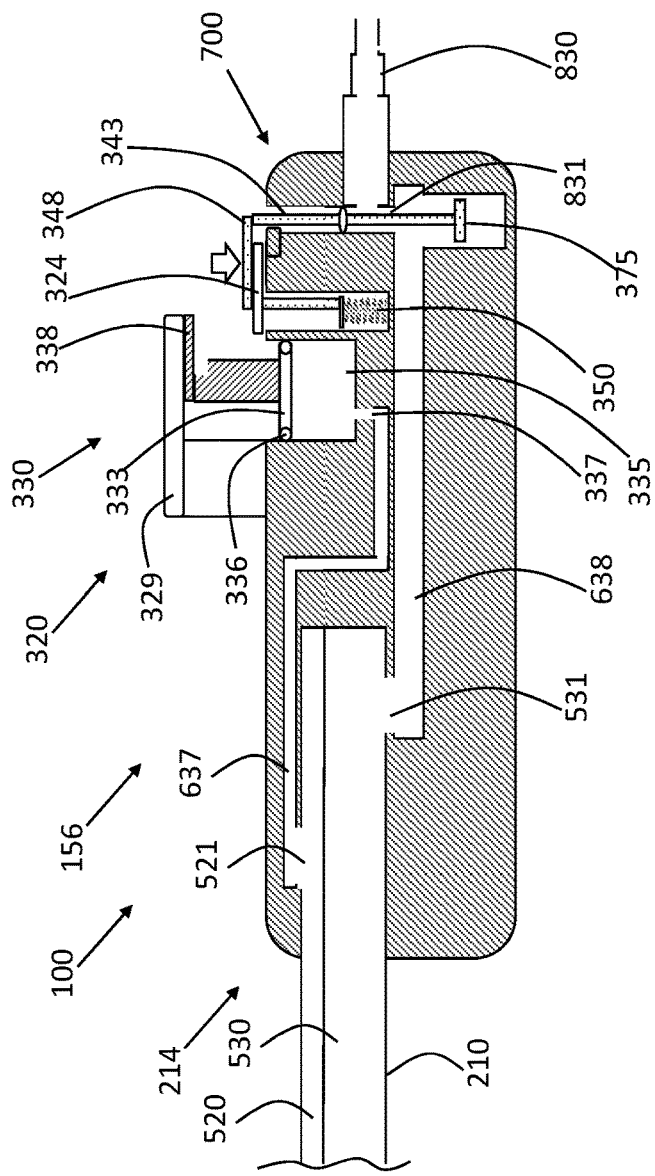
Figure 2B:
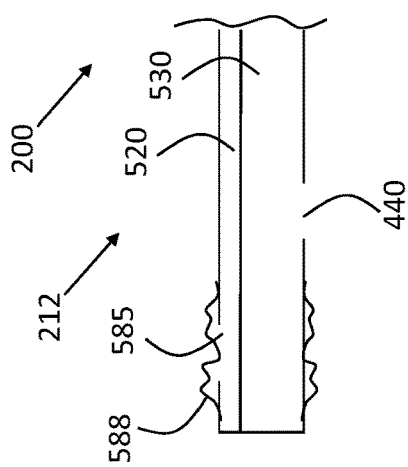
Figure 2C:
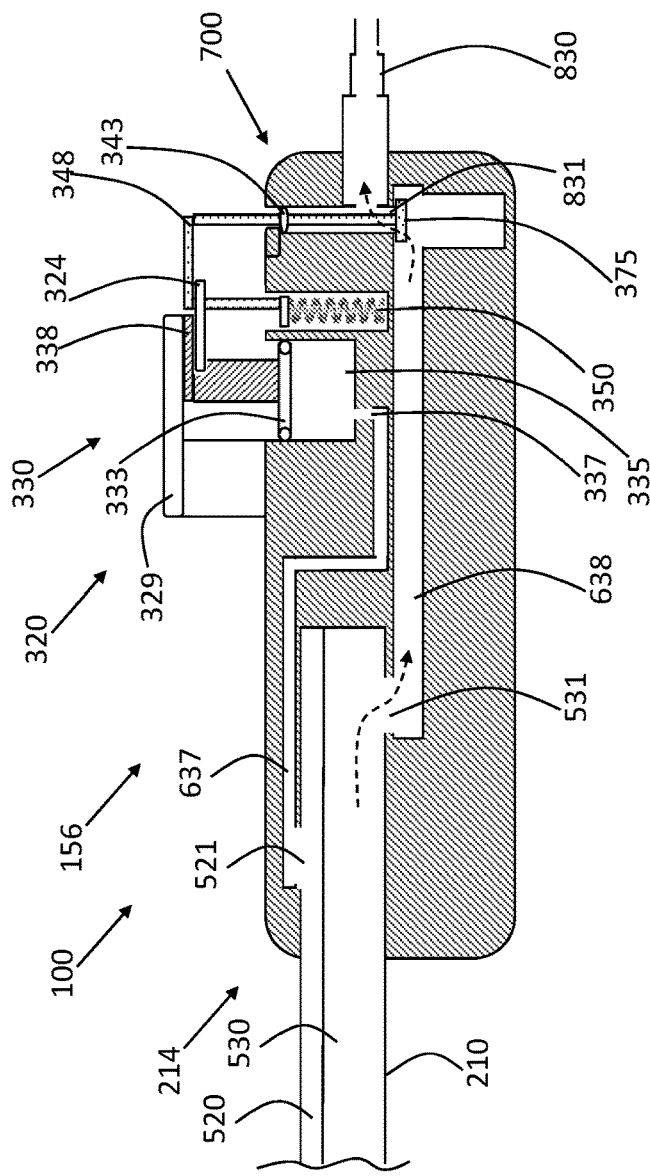
Figure 2C:
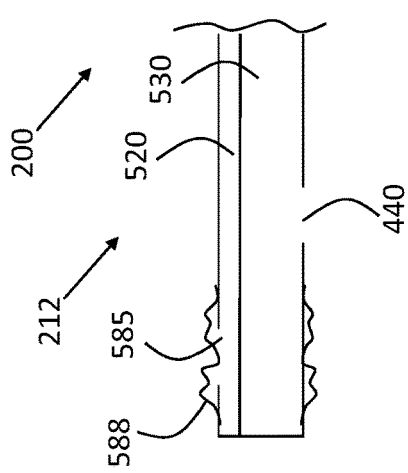
Figure 2D:
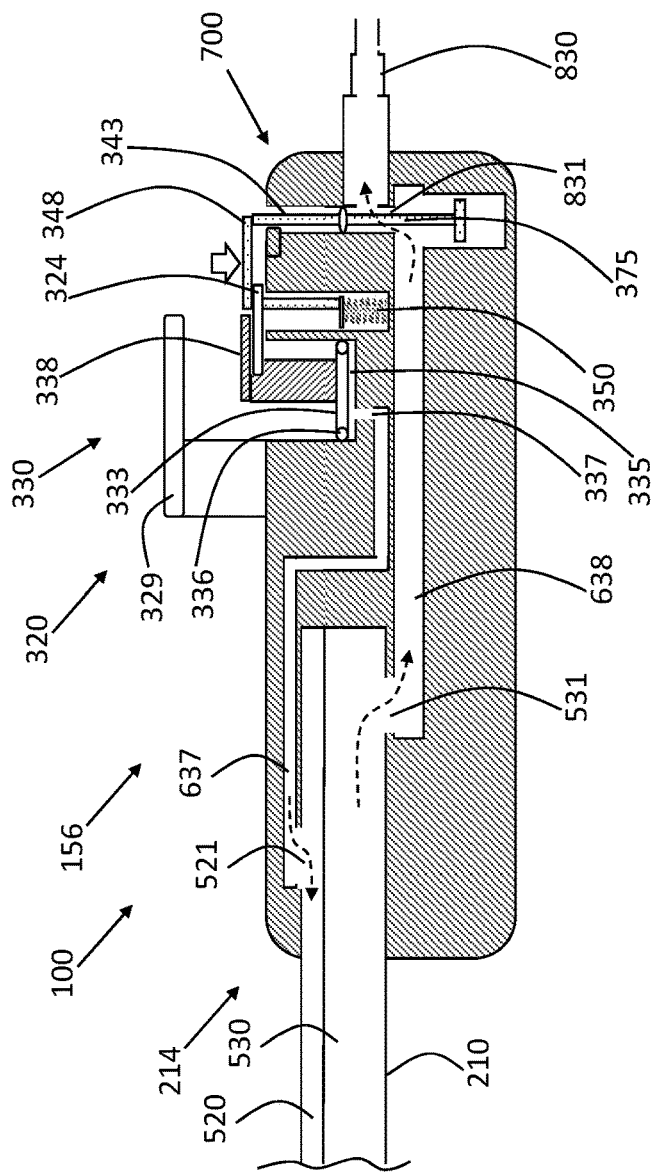
Figure 2D:
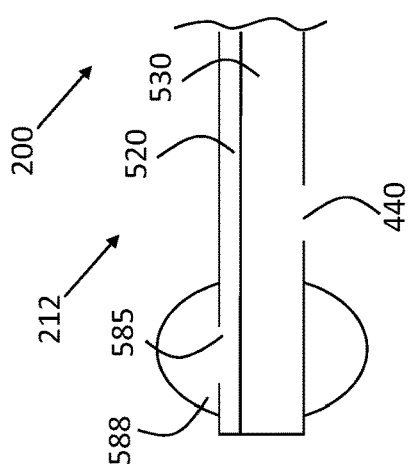

Linking element 324 is moveable with respect to mechanical suction-control button 348 and mechanical inflation-control button 338 (as well as with respect to other elements of input module 156, such as suction port 830 and the housing), and is configured to assume at least first and second spatial positions. Input module 156 is arranged such that:

at least when mechanical suction-control button 348 is in its first spatial position, as shown in FIGS. 2A and 2C, flow regulator 700 blocks fluid communication between the suction source and distal suction orifices 440, and at least when mechanical suction-control button 348 is in its second spatial position, as shown in FIGS. 2B and 2D, flow regulator 700 connects the suction source and distal suction orifices 440 in fluid communication via suction lumen 530, when, as shown in FIG. 2A, (a) linking element 324 is in its first spatial position and (b) mechanical suction-control button 348 and mechanical inflation-control button 338 are in their respective first spatial positions: depression of linking element 324 does not transition mechanical inflation-control button 338 to its second spatial position, and when, as shown in FIG. 2C, (a) linking element 324 is in its second spatial position and (b) mechanical suction-control button 348 and mechanical inflation-control button 338 are in their respective first spatial positions: depression of linking element 324 transitions mechanical inflation-control button 338 to its second spatial position, as shown in FIG. 2D.

For some applications, linking element 324 is arranged to axially slide between its first and second spatial positions. For some applications, the first and the second spatial positions of linking element 324 are first and second axial positions, and wherein linking element 324 is configured to assume at least the first and the second axial positions.

For some applications, as shown in FIGS. 2A-D, (a) the first and the second spatial positions of mechanical suction-control button 348 are first and second radial positions, and mechanical suction-control button 348 is configured to assume at least the first and the second radial positions, and (b) the first and the second spatial positions of mechanical inflation-control button 338 are first and second radial positions, and mechanical inflation-control button 338 is configured to assume at least the first and the second radial positions.

For some applications, as shown in FIGS. 2A-D, linking element 324 is moveably attached to mechanical suction-control button 348.

For some applications, as shown in FIGS. 2A-D, input module 156 is arranged such that linking element 324, when in its first spatial position, does not engage mechanical inflation-control button 338. Alternatively or additionally, for some applications, as shown in FIGS. 2A-D, input module 156 is arranged such that linking element 324, when in its second spatial position, engages mechanical inflation-control button 338.

For some applications, as shown in FIGS. 2A-D, mechanical suction-control button 348 is disposed proximally to mechanical inflation-control button 338.

For some applications, as shown in FIGS. 2A-D, mechanical suction-control button 348 is shaped so as to define a suction-control user interface surface, at least a portion (e.g., at least 1 cm2) of which is visible from outside input module 156, and is accessible by a finger of a user from outside input module 156. Mechanical inflation-control button 338 is not shaped so as to define a user interface surface. Input module 156 is arranged such that, as shown in FIG. 2A, when (a) linking element 324 is in its first spatial position and (b) mechanical suction-control button 348 is in its first spatial position: depression of the suction-control user interface surface transitions mechanical suction-control button 348 to its second spatial position, as shown in FIG. 2B. Input module 156 is arranged such that, as shown in FIG. 2C, when (a) linking element 324 is in its second spatial position and (b) mechanical suction-control button 348 and mechanical inflation-control button 338 are in their respective first spatial positions: depression of the suction-control user interface surface causes a first transition of mechanical suction-control button 348 to its second spatial position, which first transition, via linking element 324, causes a second transition of mechanical inflation-control button 338 to its second spatial position, as shown in FIG. 2D.

For some of these applications, input module 156 is arranged such that the second transition occurs simultaneously with the first transition. For some of these applications, input module 156 comprises a cover 329, which is arranged to inhibit user access to mechanical inflation-control button 338 both when linking element 324 is in its first spatial position and when linking element 324 is in its second spatial position. Typically, input module 156 is arranged such that cover 329 is stationary with respect to suction port 830 during motion of either mechanical suction-control button 348 or mechanical inflation-control button 338 between their respective first and second spatial positions.

For some applications, mechanical suction-control button 348 and mechanical inflation-control button 338 are biased toward their respective first spatial positions. For some applications, input module 156 comprises one or more springs 350 that are arranged to bias mechanical suction-control button 348 and mechanical inflation-control button 338 toward their respective first spatial positions. The one or more springs 350 may have any of the configurations described hereinabove with reference to FIGS. 1A-D.

For some applications, inflation chamber 335 comprises the rigid lateral chamber walls, as described hereinabove with reference to FIGS. 1A-D, while for other applications, inflation chamber 335 comprises elastic compartment 332, as described hereinabove with reference to FIGS. 1A-D and hereinbelow with reference to FIGS. 3A-B.

For some applications, mechanical inflation-control button 338 is configured to additionally assume a deflation-inducing spatial position, and input module 156 further comprises a mechanical deflation-control button, such as described hereinbelow with reference to FIGS. 7A-D, mutatis mutandis.

For cleaning a ventilation tube, the cleaning action typically comprises the steps described hereinabove with reference to FIGS. 1A-D, mutatis mutandis.

Figure 3A:
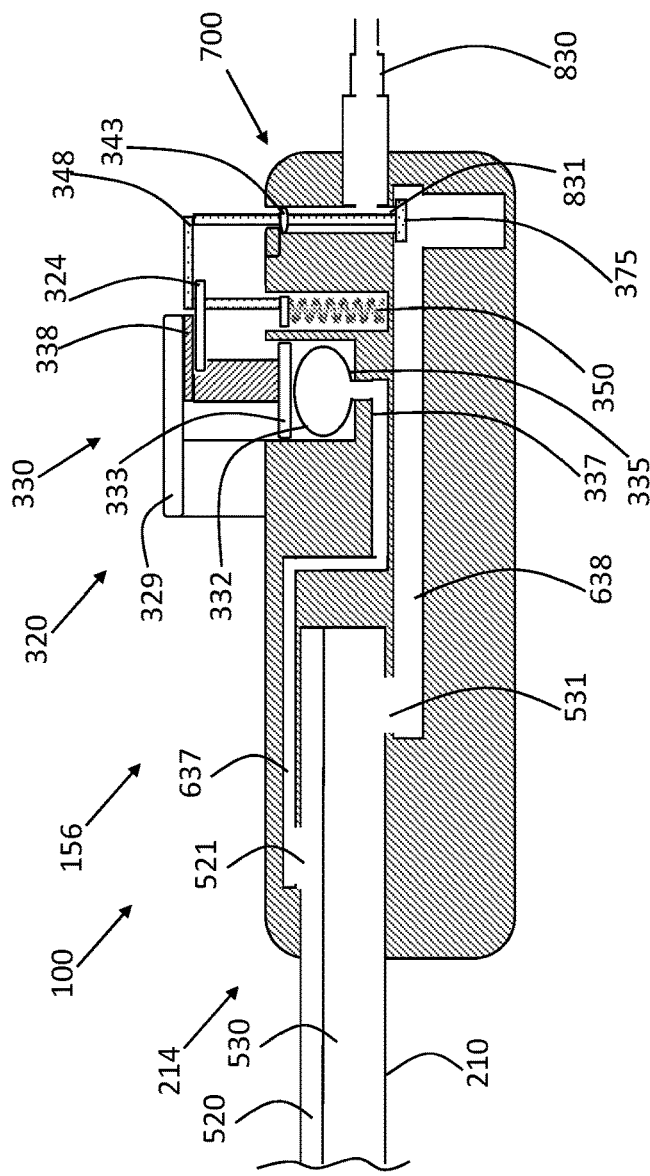
FIGS. 3A-B are schematic cross-sectional illustrations of yet another configuration of the closed suction cleaning system of FIGS. 1A-D in respective states, in accordance with an application of the present invention.
Figure 3A:
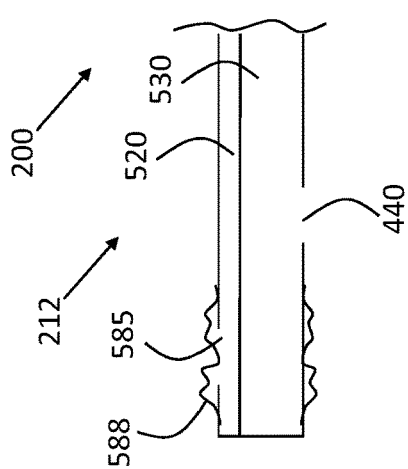
Figure 3B:
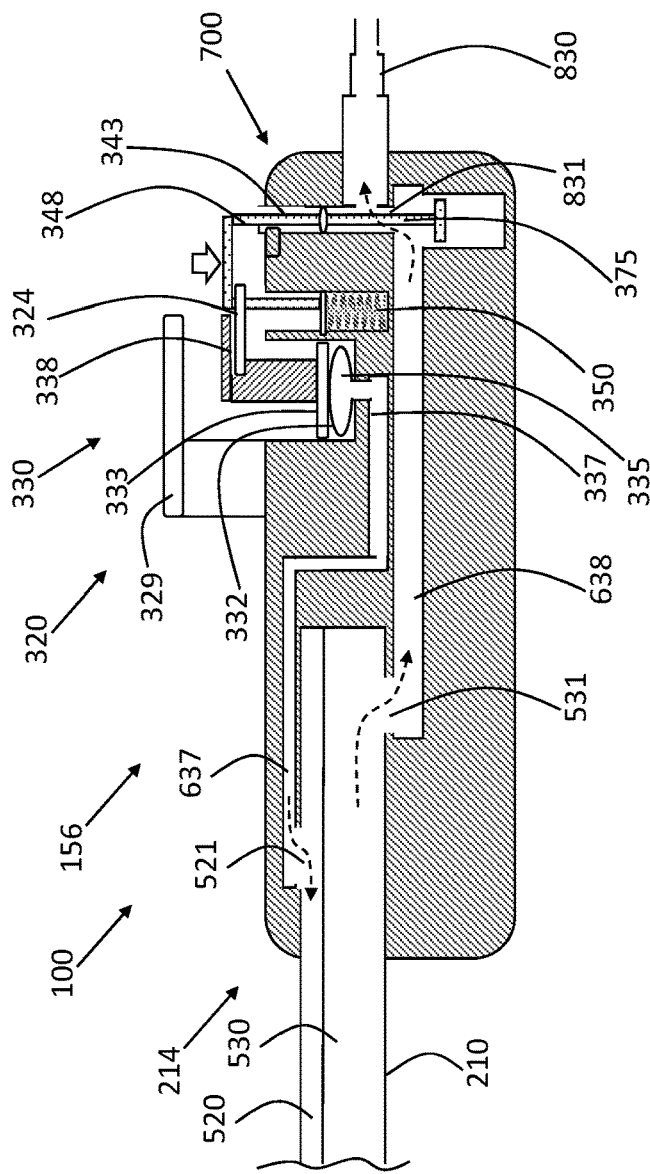
Figure 3B:
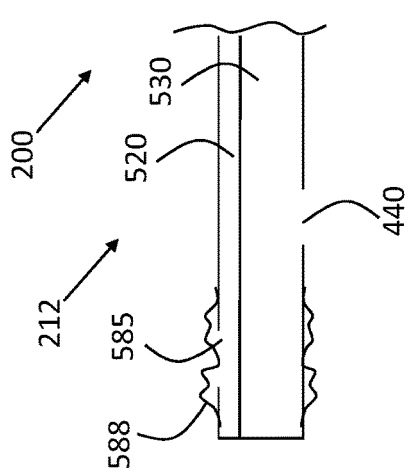

Reference is now made to FIGS. 3A-B, which are schematic illustration of yet another configuration of cleaning system 100 in respective states, in accordance with an application of the present invention. The illustrated configuration is identical to the configuration illustrated in FIGS. 2C-D, except that inflation chamber 335 comprises elastic compartment 332, and input module 156 is configured such that the transition of mechanical inflation-control button 338 from its first spatial position to its second spatial position compresses elastic compartment 332, thereby mechanically and non-electrically increasing the pressure in an interior of elastic compartment 332. This configuration of inflation chamber 335 may be implemented in any of the configurations described herein, mutatis mutandis.

Figure 4A:
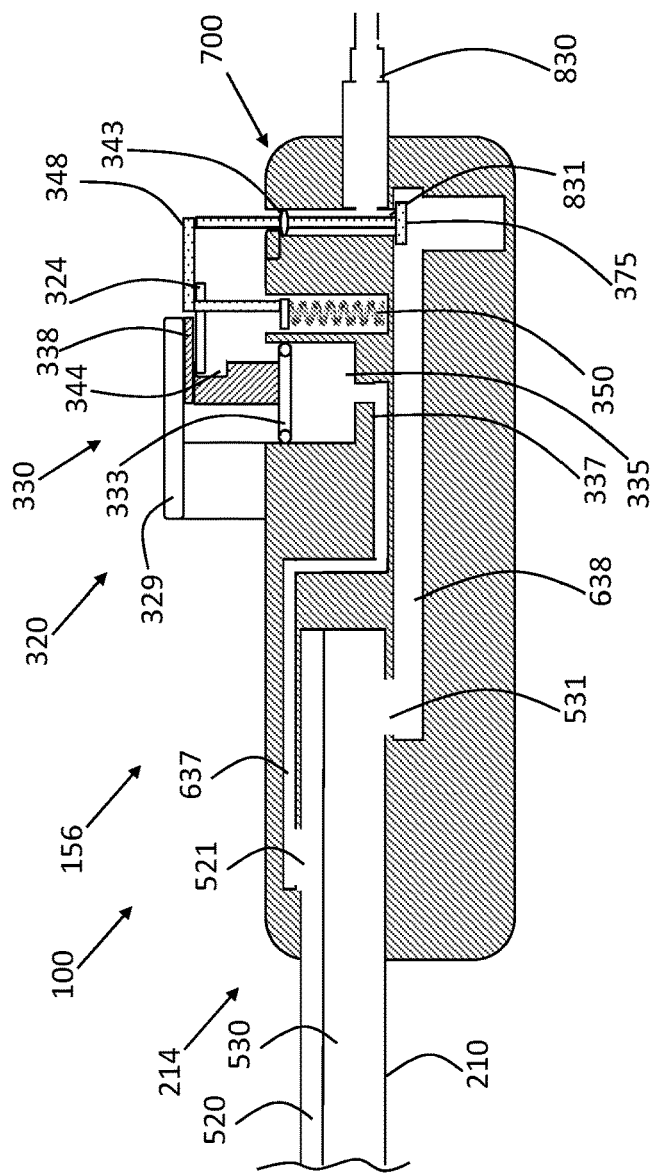
FIGS. 4A-C are schematic cross-sectional illustrations of still another configuration of the closed suction cleaning system of FIGS. 1A-D in respective states, in accordance with an application of the present invention.
Figure 4A:
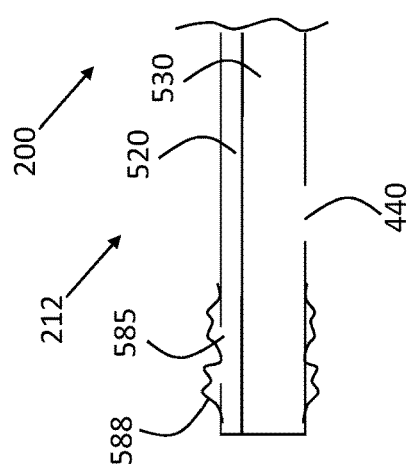
Figure 4B:
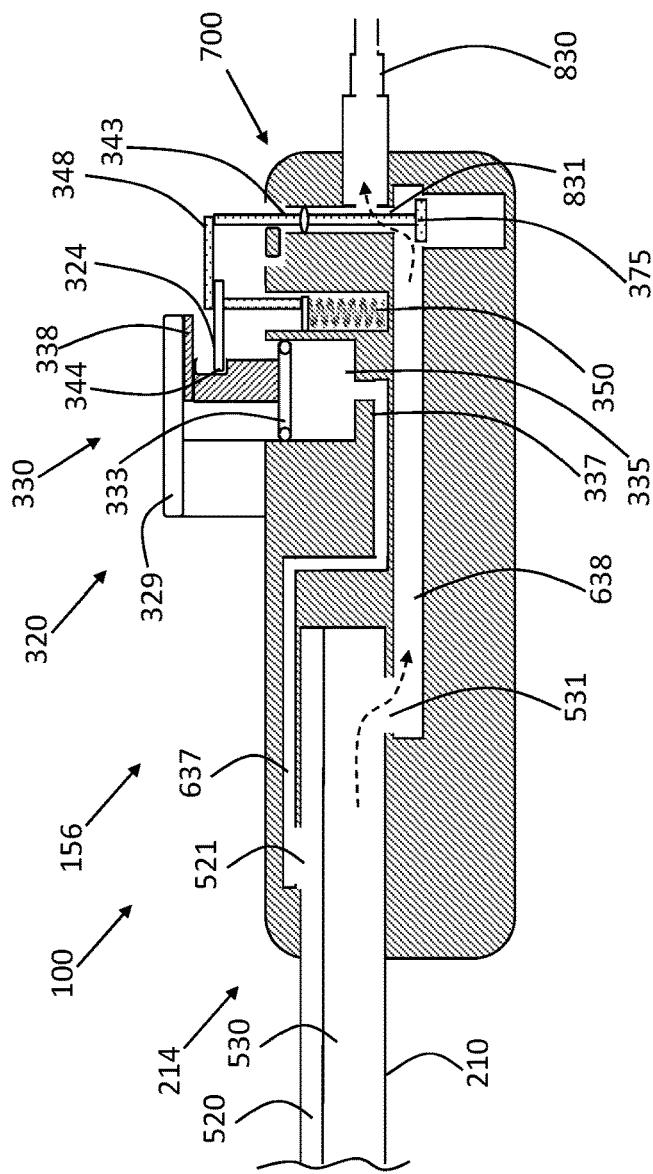
Figure 4B:
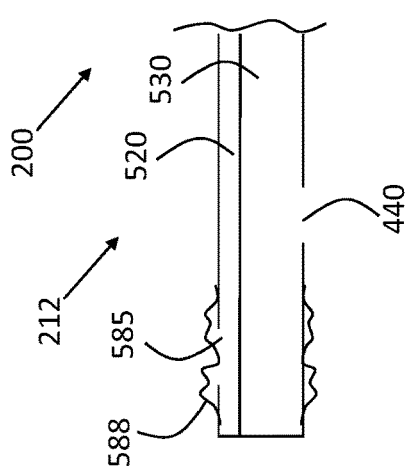
Figure 4C:
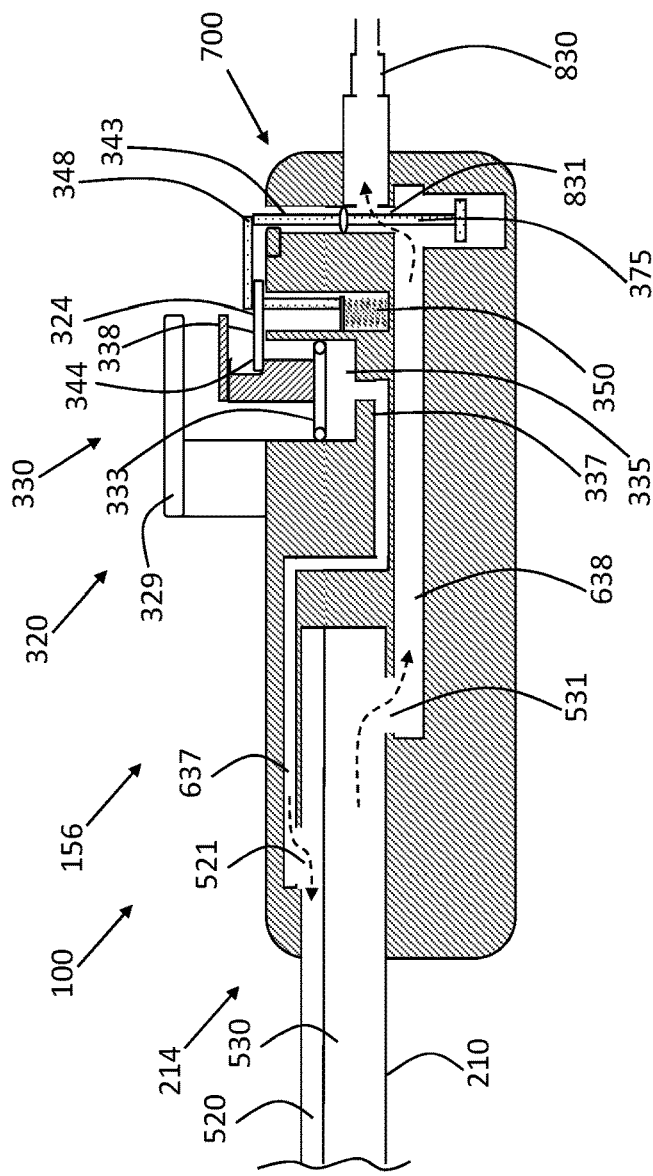
Figure 4C:
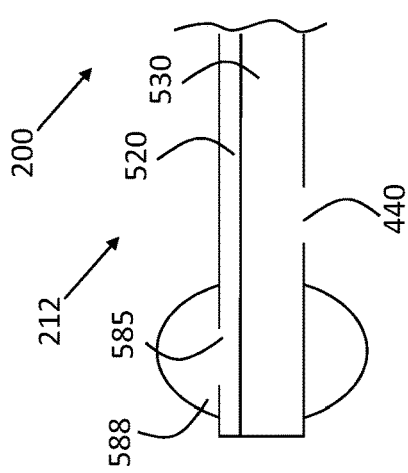

Reference is now made to FIGS. 4A-C, which are schematic cross-sectional illustrations of still another configuration of closed suction cleaning system 100 in respective states, in accordance with an application of the present invention. Except as described hereinbelow, this configuration of cleaning system 100 may implement any of the features of the configuration of the system described hereinabove with reference to FIGS. 1A-D, 2A-D, and/or 3A-B, mutatis mutandis.

In this configuration, mechanical suction-control button 348, which is configured to assume at least a first spatial position (shown in FIG. 4A), a second spatial position (shown in FIG. 4B), and a third spatial position (shown in FIG. 4C), the second spatial position between the first and the third spatial positions. Mechanical inflation-control button 338 (*a*) is not shaped so as to define a user interface surface, (b) is configured to assume at least a first spatial position (shown in FIGS. 4A-B) and a second spatial position (shown in FIG. 4C), and (c) is configured to mechanically and non-electrically increase pressure in the interior of inflation chamber 335 during a transition of mechanical inflation-control button 338 from its first spatial position to its second spatial position.

In this configuration, input module 156 (mechanical user control assembly 320 thereof) comprises reversibly-engageable linking element 324, which, in this configuration, is fixed to mechanical suction-control button 348, and is configured to assume at least a first spatial position (shown in FIG. 4A), a second spatial position (shown in FIG. 4B), and a third spatial position (shown in FIG. 4C), the second spatial position between the first and the third spatial positions.

In this configuration, input module 156 (mechanical user control assembly 320 thereof) comprises cover 329, which is arranged to inhibit user access to mechanical inflation-control button 338.

In this configuration, input module 156 is arranged such that:

at least when mechanical suction-control button 348 is in its first spatial position, as shown in FIG. 4A, flow regulator 700 blocks fluid communication between the suction source and distal suction orifices 440, and at least when mechanical suction-control button 348 is in its second and third spatial positions, as shown in FIGS. 4B-C, flow regulator 700 connects the suction source and distal suction orifices 440 in fluid communication via suction lumen 530, a first transition of mechanical suction-control button 348 from its first spatial position (as shown in FIG. 4A) to its second spatial position (as shown in FIG. 4B) causes a second transition of linking element 324 from its first spatial position (as shown in FIG. 4A) to its second spatial position (as shown in FIG. 4B), and a third transition of mechanical suction-control button 348 from its second spatial position (as shown in FIG. 4B) to its third spatial position (as shown in FIG. 4C) causes a fourth transition of linking element 324 from its second spatial position (as shown in FIG. 4B) to its third spatial position (as shown in FIG. 4C), which in turn causes a fifth transition of mechanical inflation-control button 338 to its second spatial position (as shown in FIG. 4C). For example, linking element 324 may engage an indentation 344 defined by inflation-control button 338.

This arrangement allows the user to depress a single user interface button (mechanical suction-control button 348), and to sequentially first cause activation of suction and subsequently cause inflation of inflatable element 588. Typically, during this transition, before inflation of inflatable element 588 begins, at least 30% of the maximum suction is achieved. In other words, input module 156 is configured to apply a maximum level of suction to distal suction orifices 440 when mechanical suction-control button 348 is in its third spatial position, and input module 156 is configured, during a transition of mechanical suction-control button 348 from its first spatial position to its third spatial position via its second spatial position, to apply at least 30% of the maximum level of suction to distal suction orifices 440 before inflation of inflatable element 588 begins.

For some applications, input module 156 is arranged such that the first transition does not move mechanical inflation-control button 338. Alternatively or additionally, for some applications, input module 156 is arranged such that the first transition does not radially move mechanical inflation-control button 338. For some applications, input module 156 is arranged such that the fifth transition occurs simultaneously with the fourth transition.

For some applications, as shown in FIGS. 4A-C, (a) linking element 324 is radially-moveable, (b) the first, the second, and the third spatial positions are first, second, and third radial positions, respectively, and (c) linking element 324 is configured to assume at least the first, the second, and the third radial positions. Alternatively or additionally, for some applications, (a) the first, the second, and the third spatial positions of mechanical suction-control button 348 are first, second, and third radial positions, and mechanical suction-control button 348 is configured to assume at least the first, the second, and the third radial positions, and (b) the first and the second spatial positions of mechanical inflation-control button 338 are first and second radial positions, and mechanical inflation-control button 338 is configured to assume at least the first and the second radial positions.

For some applications, mechanical suction-control button 348 is shaped so as to define a suction-control user interface surface, at least 1 cm2 of which is visible from outside input module 156, and is accessible by a finger of a user from outside input module 156, and wherein depression of the suction-control user interface surface causes the first and the third transitions. For some applications, less than 1 cm2 of linking element 324 is visible from outside input module 156, and is accessible by a finger of a user from outside input module 156.

For some applications, linking element 324 is shaped so as to define a linking user interface surface, at least a portion (e.g., at least 1 cm2) of which is visible from outside input module 156, and is accessible by a finger of a user from outside input module 156, and wherein depression of the linking user interface surface causes the first and the third transitions.

Typically, input module 156 is arranged such that cover 329 is stationary with respect to suction port 830 (as well as with respect to other elements of input module 156, such as the housing) during motion of either mechanical suction-control button 348 or mechanical inflation-control button 338 between their respective first and second spatial positions.

For some applications, as shown in FIGS. 4A-C, mechanical suction-control button 348 is disposed proximally to mechanical inflation-control button 338.

For some applications, mechanical suction-control button 348 and mechanical inflation-control button 338 are biased toward their respective first spatial positions. For some applications, input module 156 comprises one or more springs 350 that are arranged to bias mechanical suction-control button 348 and mechanical inflation-control button 338 toward their respective first spatial positions. The one or more springs 350 may have any of the configurations described hereinabove with reference to FIGS. 1A-D.

For some applications, inflation chamber 335 comprises the rigid lateral chamber walls, as described hereinabove with reference to FIGS. 1A-D, while for other applications, inflation chamber 335 comprises elastic compartment 332, as described hereinabove with reference to FIGS. 1A-D and 3A-B.

For some applications, mechanical inflation-control button 338 is configured to additionally assume a deflation-inducing spatial position, and input module 156 further comprises a mechanical deflation-control button, such as described hereinbelow with reference to FIGS. 7A-D, mutatis mutandis.

For suctioning the trachea, typically the following steps are performed:
  inserting cleaning catheter 200 into the ventilation tube in a proximal to distal direction while inflatable element 588 is essentially deflated, such in the state shown in FIG. 4A; typically, in order to perform "deep suction," the distal end of the cleaning catheter is advanced beyond the distal end of the ventilation tube; and
  applying suction to the trachea by transitioning input module 156 to the state shown in FIG. 4B.

For cleaning a ventilation tube, the cleaning action typically comprises the following steps, which are typically performed in the following order:
  inserting cleaning catheter 200 into the ventilation tube in a proximal to distal direction while inflatable element 588 is essentially deflated, such in the state shown in FIG. 4A;
  applying suction and inflating inflatable element 588 at a location near the distal end of the ventilation tube by transitioning input module 156 to the state shown in FIG. 4C;
  withdrawing the catheter along the ventilation tube in a distal to proximal direction while the inflatable element is inflated and suction is applied to the one or more suction orifices; and
  deflating the inflatable element when the inflatable element is near the proximal end of the ventilation tube or fully outside the proximal end of the ventilation tube, by transitioning input module 156 to the state shown in FIG. 4A.

Figure 5A:
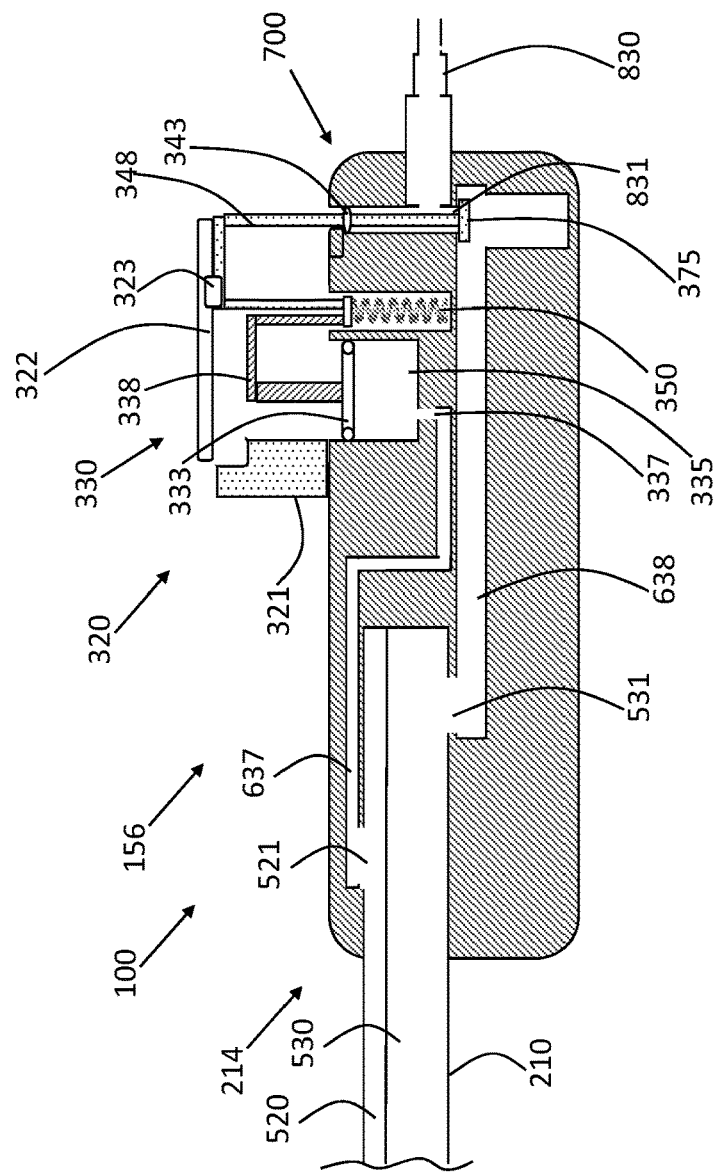
FIGS. 5A-C are schematic cross-sectional illustrations of another configuration of the closed suction cleaning system of FIGS. 1A-D in respective states, in accordance with an application of the present invention.
Figure 5A:
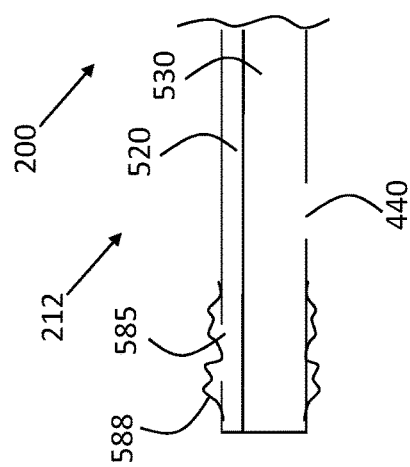
Figure 5B:
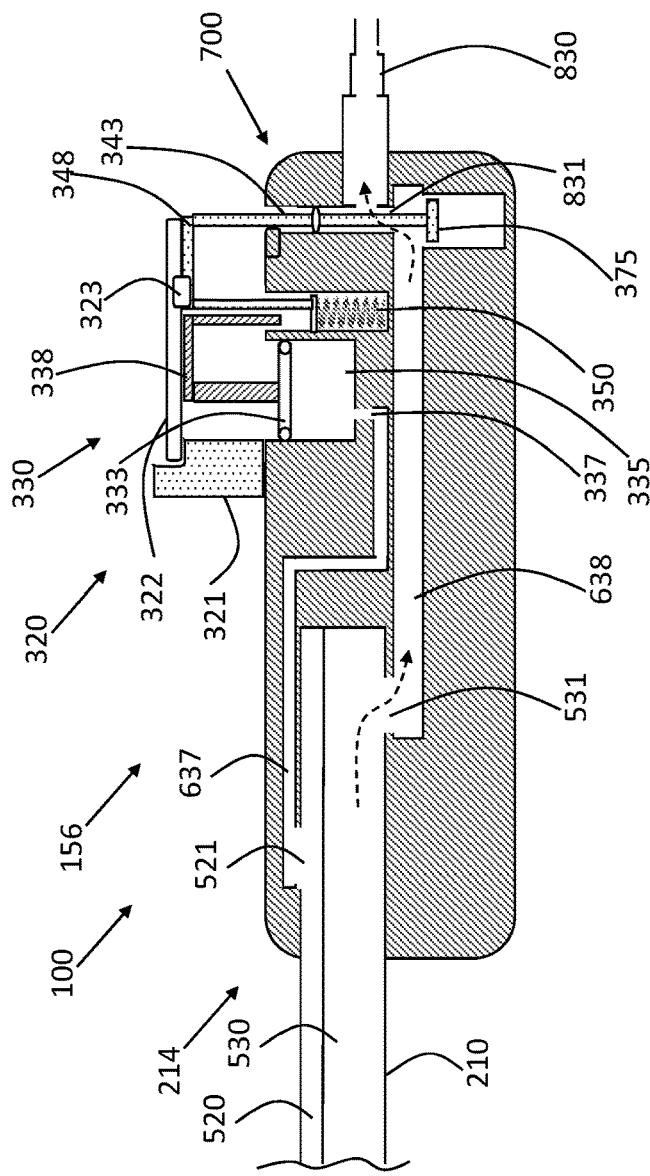
Figure 5B:
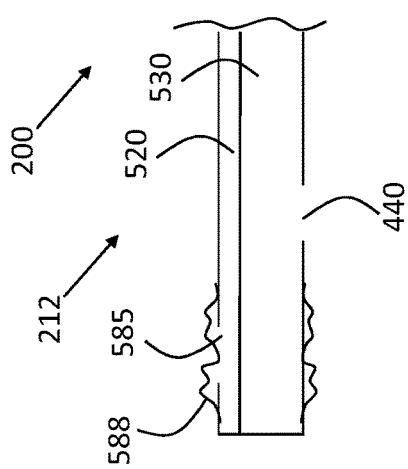
Figure 5C:
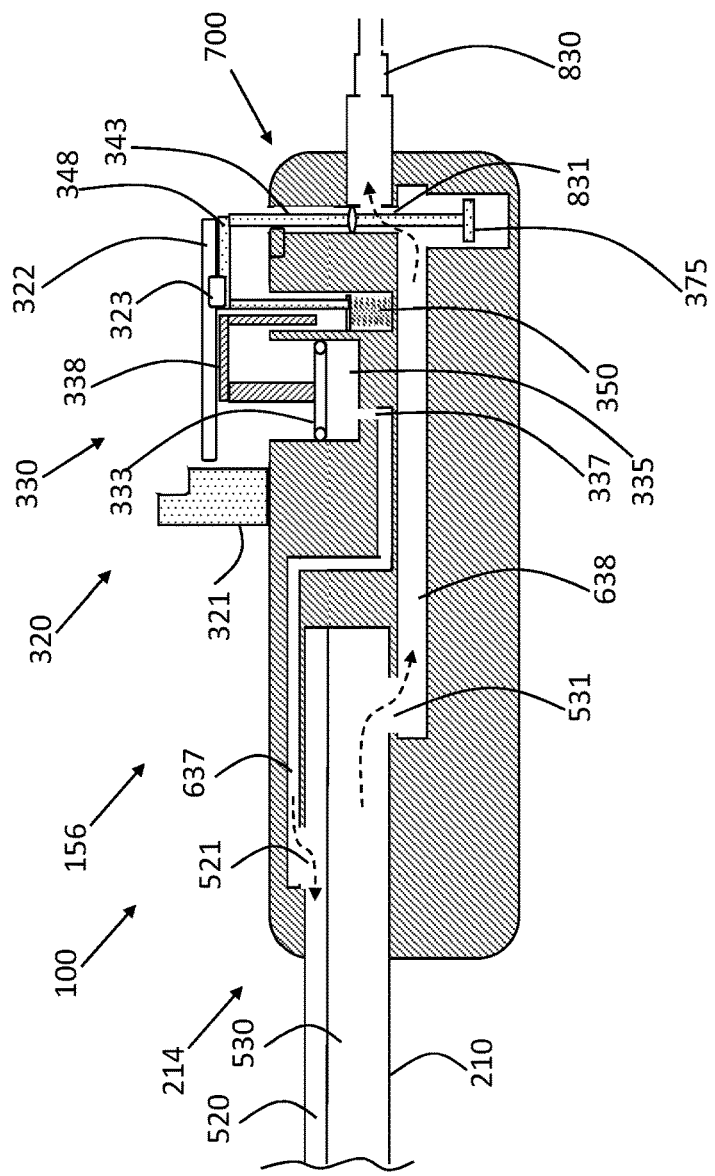
Figure 5C:
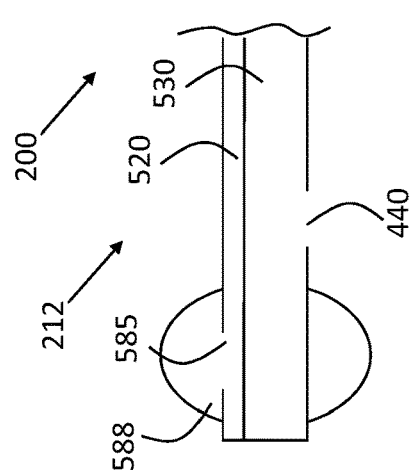

Reference is now made to FIGS. 5A-C, which are schematic cross-sectional illustrations of still another configuration of closed suction cleaning system 100 in respective states, in accordance with an application of the present invention. Except as described hereinbelow, this configuration of cleaning system 100 may implement any of the features of the configuration of the system described hereinabove with reference to FIGS. 1A-D, 2A-D, 3A-B, and/or 4C-D, mutatis mutandis.

In this configuration, mechanical suction-control button 348 is configured to assume at least a first spatial position (shown in FIG. 5A), a second spatial position (shown in FIG. 5B), and a third spatial position (shown in FIG. 5C), the second spatial position between the first and the third spatial positions. In this configuration, mechanical inflation-control button 338 (a) is not shaped so as to define a user interface surface, (b) is configured to assume at least a first spatial position (shown in FIGS. 5A-B) and a second spatial position (shown in FIG. 5C), and (c) is configured to mechanically and non-electrically increase pressure in the interior of inflation chamber 335 during a transition of mechanical inflation-control button 338 from its first spatial position to its second spatial position.

In this configuration, input module 156 (mechanical user control assembly 320 thereof) comprises reversibly-engageable linking element 322, which, in this configuration, is fixed to mechanical suction-control button 348, and is configured to assume at least: (a) a first spatial position (shown in FIG. 5A), in which linking element 322 does not engage mechanical inflation-control button 338, (b) a second spatial position (shown in FIG. 5B), and (c) a third spatial position (shown in FIG. 5C), in which linking element 322 engages mechanical inflation-control button 338, wherein the second spatial position is between the first and the third spatial positions.

In this configuration, input module 156 (mechanical user control assembly 320 thereof) comprises a moveable stopper 321, which is moveably fixed to input module 156, and which is configured to assume at least:

a first spatial position, as shown FIG. 5B, in which moveable stopper 321 blocks a first transition of linking element 322 from its second spatial position to its third spatial position (moveable stopper is also shown in its first spatial position in FIG. 5A), and a second spatial position, as shown in FIG. 5C, in which moveable stopper 321 does not block the first transition of linking element 322 from its second spatial position to its third spatial position.

For some applications, moveable stopper 321 is shaped so as to define a blocking surface, which, when moveable stopper 321 is in its first spatial position, blocks the first transition of linking element 322 from its second spatial position to its third spatial position.

Input module 156 is arranged such that:
at least when mechanical suction-control button 348 is in its first spatial position, as shown in FIG. 5A, flow regulator 700 blocks fluid communication between the suction source and distal suction orifices 440, and at least when mechanical suction-control button 348 is in its second and third spatial positions (as shown in FIGS. 5B and 5C, respectively), flow regulator 700 connects the suction source and distal suction orifices 440 in fluid communication via suction lumen 530, and when (a) linking element 322 is in its second spatial position, (b) mechanical suction-control button 348 is in its second spatial position, (c) mechanical inflation-control button 338 is in its first spatial position, and (d) moveable stopper 321 is in its second spatial position: depression of the mechanical control button causes a second transition of mechanical suction-control button 348 to its third spatial position, which second transition, via linking element 322, causes a third transition of mechanical inflation-control button 338 to its second spatial position, as shown in FIG. 5C.

For some applications, input module 156 is arranged such that the third transition occurs simultaneously with the second transition.

For some applications, linking element 322 is shaped so as to define a linking user interface surface, at least a portion (e.g., at least 1 cm2) of which is visible from outside input module 156, and is accessible by a finger of a user from outside input module 156, and depression of the linking user interface surface transitions mechanical suction-control button 348 from its first spatial position, to its second spatial position, to its third spatial position.

For some applications, mechanical suction-control button 348 is shaped so as to define a suction-control user interface surface, at least a portion (e.g., at least 1 cm2) of which is visible from outside input module 156, and is accessible by a finger of a user from outside input module 156, and wherein depression of the suction-control user interface surface transitions mechanical suction-control button 348 from its first spatial position, to its second spatial position, to its third spatial position (configuration not shown).

For some applications, as shown in FIGS. 5A-C, (a) linking element 322 is radially-moveable, (b) the first, the second, and the third spatial positions are first, second, and third radial positions, respectively, and (c) linking element 322 is configured to assume at least the first, the second, and the third radial positions. Alternatively or additionally, for some applications, as shown in FIGS. 5A-C, (a) the first, the second, and the third spatial positions of mechanical suction-control button 348 are first, second, and third radial positions, and mechanical suction-control button 348 is configured to assume at least the first, the second, and the third radial positions, and (b) the first and the second spatial positions of mechanical inflation-control button 338 are first and second radial positions, and wherein mechanical inflation-control button 338 is configured to assume at least the first and the second radial positions.

For some applications, mechanical suction-control button 348 is disposed proximally to mechanical inflation-control button 338.

For some applications, mechanical suction-control button 348 and mechanical inflation-control button 338 are biased toward their respective first spatial positions. For some applications, input module 156 comprises one or more springs 350 that are arranged to bias mechanical suction-control button 348 and mechanical inflation-control button 338 toward their respective first spatial positions. The one or more springs 350 may have any of the configurations described hereinabove with reference to FIGS. 1A-D.

For some applications, inflation chamber 335 comprises the rigid lateral chamber walls, as described hereinabove with reference to FIGS. 1A-D, while for other applications, inflation chamber 335 comprises elastic compartment 332, as described hereinabove with reference to FIGS. 1A-D and 3A-B.

For some applications, mechanical inflation-control button 338 is configured to additionally assume a deflation-inducing spatial position, and input module 156 further comprises a mechanical deflation-control button, such as described hereinbelow with reference to FIGS. 7A-D, mutatis mutandis.

For suctioning the trachea, typically the following steps are performed:
inserting cleaning catheter 200 into the ventilation tube in a proximal to distal direction while inflatable element 588 is essentially deflated and moveable stopper 321 is in its first spatial position, such in the state shown in FIG. 5A; typically, in order to perform "deep suction,"

the distal end of the cleaning catheter is advanced beyond the distal end of the ventilation tube; and applying suction to the trachea by transitioning input module 156 to the state shown in FIG. 5B.

For cleaning a ventilation tube, the cleaning action typically comprises the following steps, which are typically performed in the following order:

inserting cleaning catheter 200 into the ventilation tube in a proximal to distal direction while inflatable element 588 is essentially deflated and moveable stopper 321 is in its first spatial position, such in the state shown in FIG. 5A;

transitioning moveable stopper 321 to its second spatial position;

applying suction and inflating inflatable element 588 at a location near the distal end of the ventilation tube by transitioning input module 156 to the state shown in FIG. 5C;

withdrawing the catheter along the ventilation tube in a distal to proximal direction while the inflatable element is inflated and suction is applied to the one or more suction orifices; and deflating the inflatable element when the inflatable element is near the proximal end of the ventilation tube or fully outside the proximal end of the ventilation tube, by transitioning input module 156 to the state shown in FIG. 5A.

Figure 6A:
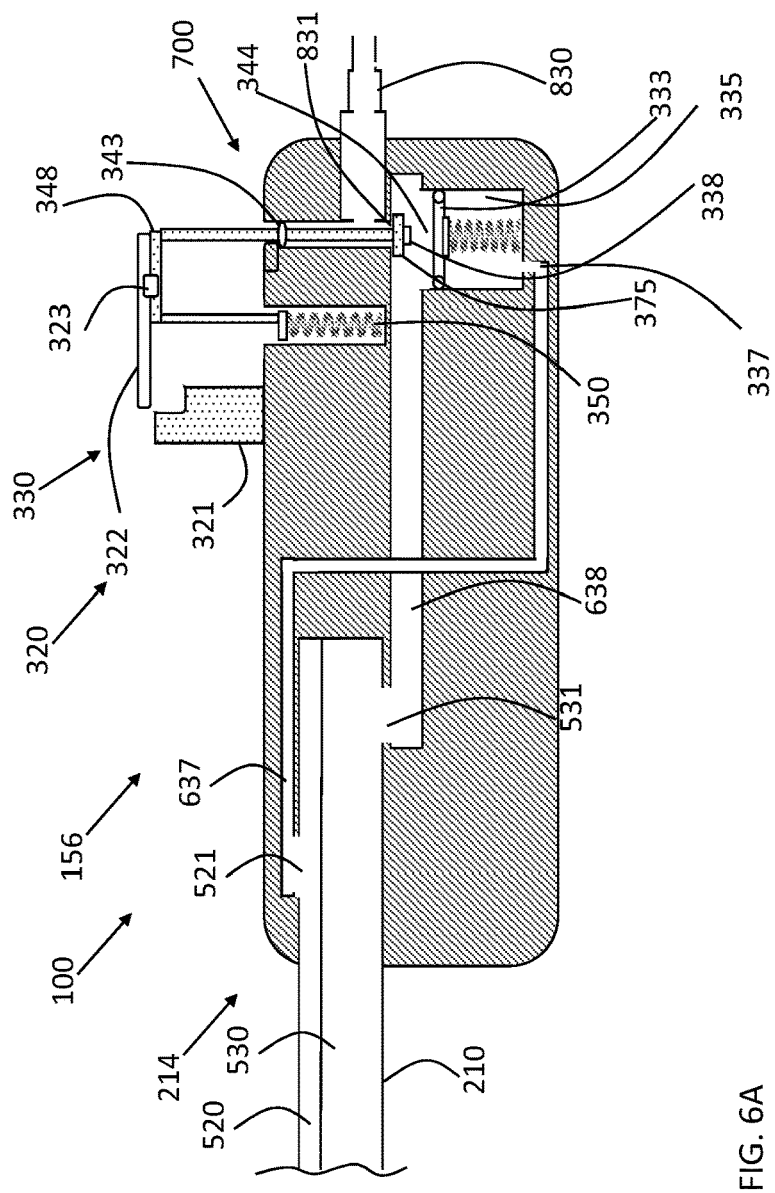
FIGS. 6A-C are schematic cross-sectional illustrations of yet another configuration of the closed suction cleaning system of FIGS. 1A-D in respective states, in accordance with an application of the present invention.
Figure 6A:
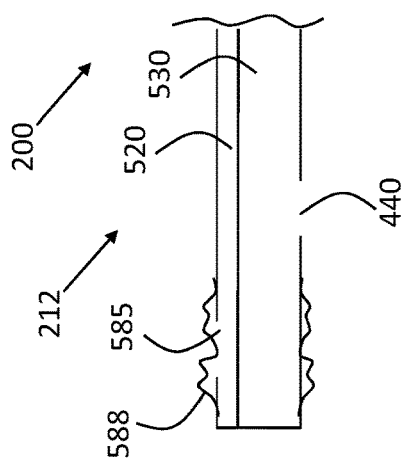
Figure 6B:
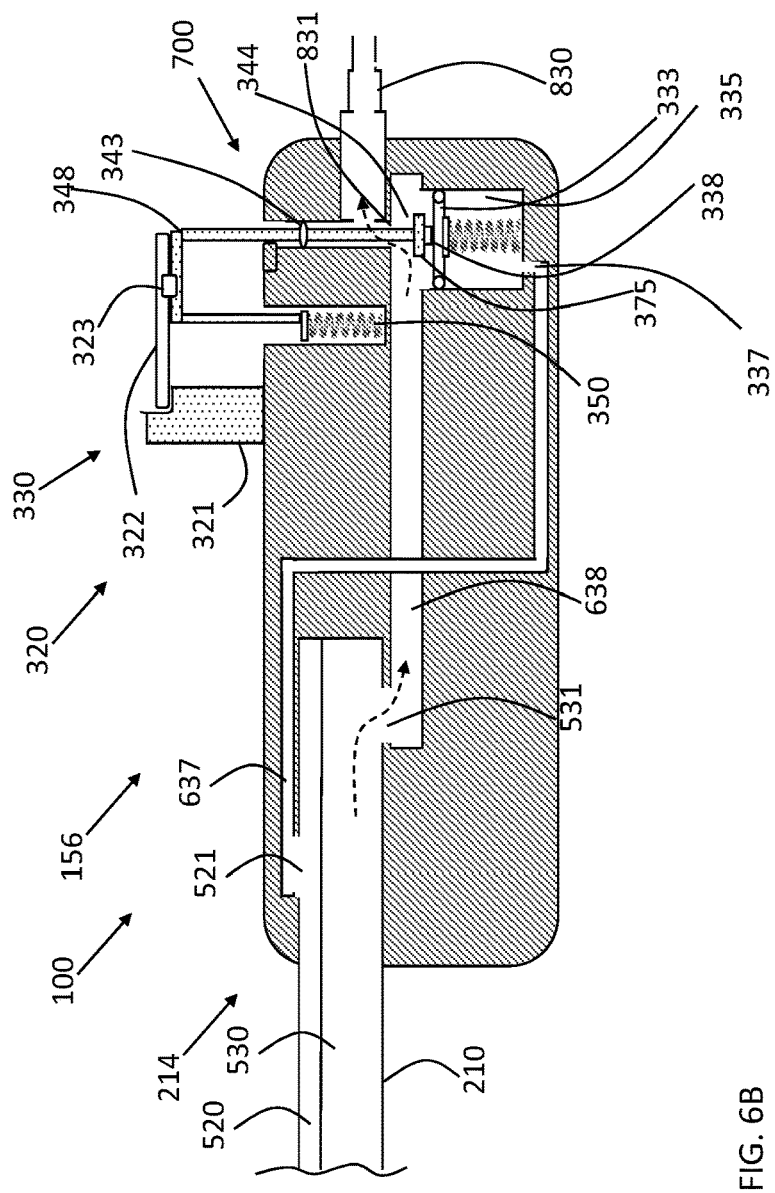
Figure 6B:
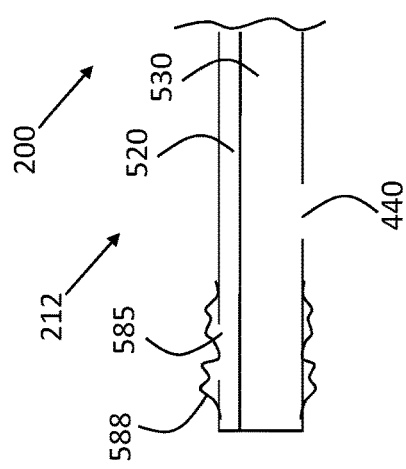
Figure 6C:
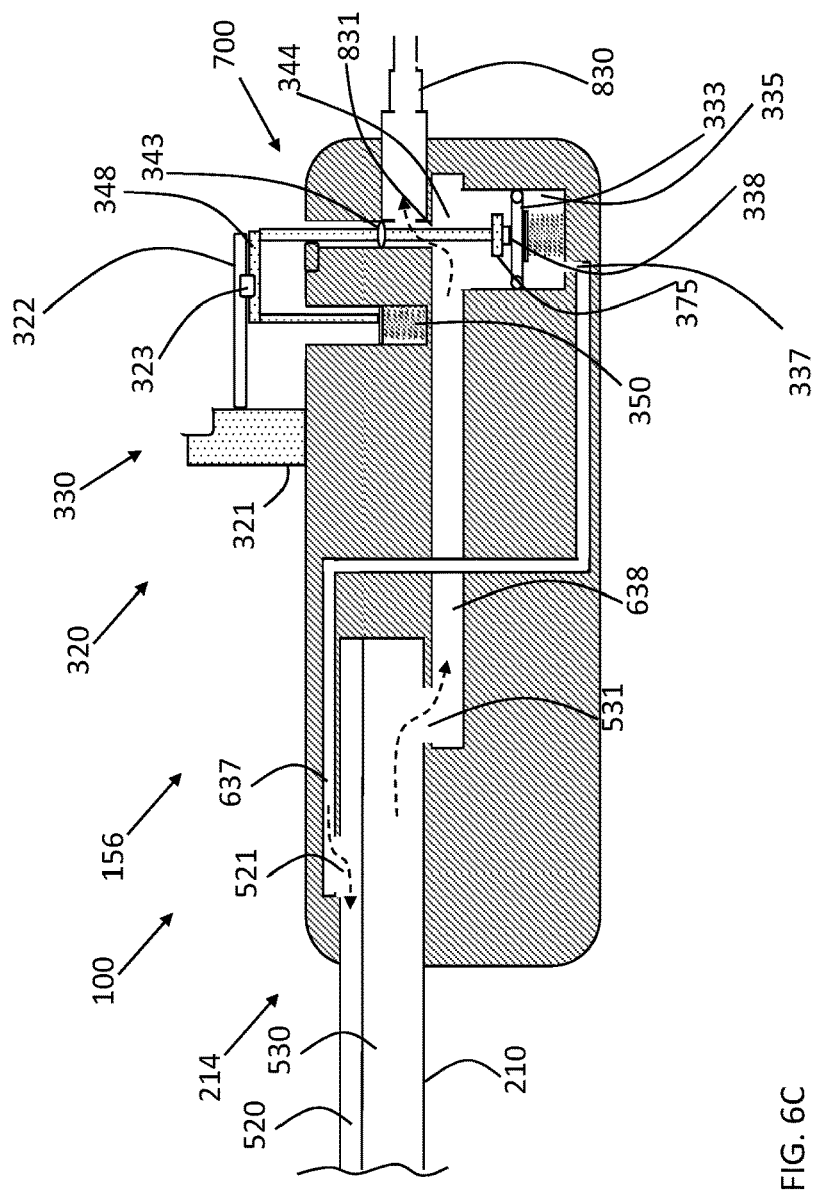
Figure 6C:
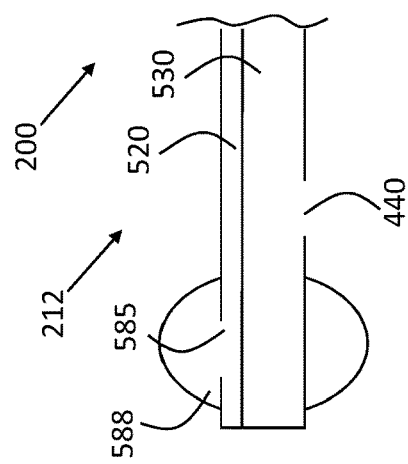

Reference is now made to FIGS. 6A-C, which are schematic illustrations of yet another configuration of cleaning system 100 in respective states, in accordance with an application of the present invention. This configuration may be used in combination with any of the other configurations describe herein, mutatis mutandis. In this configuration, input module 156 comprises at least two springs 350, one of which is arranged to bias mechanical suction-control button 348 toward its first spatial position, and second of which is disposed within inflation chamber 335.

Reference is now made to FIGS. 7A-D, which are schematic cross-sectional illustrations of still another configuration of closed suction cleaning system 100 in respective states, in accordance with an application of the present invention. Except as described hereinbelow, this configuration of cleaning system 100 may implement any of the features of the configuration of the system described hereinabove with reference to FIGS. 1A-D, 2A-D, 3A-B, 4C-D, 5A-C, and/or 6A-C mutatis mutandis.

In this configuration, mechanical inflation-control button 338 is configured to additionally assume a deflation-inducing spatial position, as shown in FIG. 8B. The first spatial position is between the deflation-inducing spatial position and the second spatial position. Mechanical inflation-control button 338 is configured to mechanically and non-electrically increase pressure in the interior of inflation chamber 335 during transition of mechanical inflation-control button 338 from its deflation-inducing spatial position to its first spatial position, and from its first spatial position to its second spatial position. Although mechanical inflation-control button 338 is shown as not being fixed to spring 350, mechanical inflation-control button 338 may alternatively be fixed to spring 350.

Figure 7A:
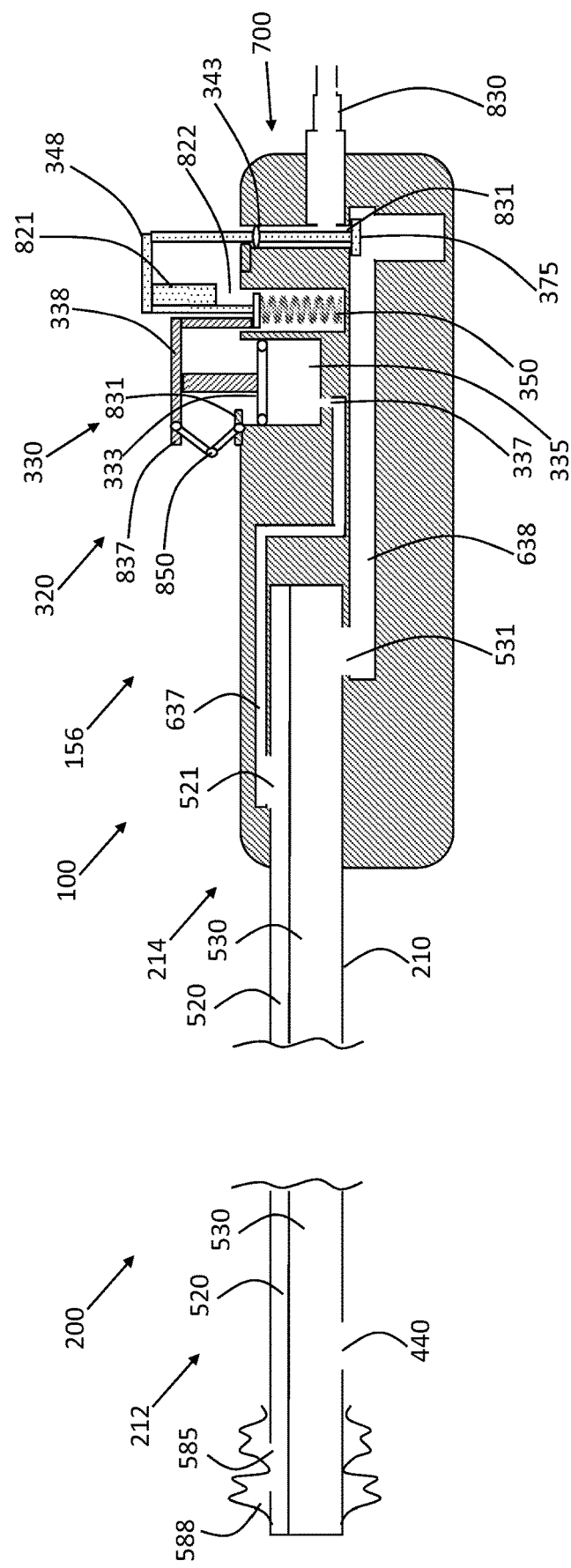
FIGS. 7A-D are schematic cross-sectional illustrations of still another configuration of the closed suction cleaning system of FIGS. 1A-D in respective states, in accordance with an application of the present invention.

In this configuration, input module 156 further comprises a mechanical deflation-control button 850, which is arranged such that when mechanical inflation-control button 338 is in its first spatial position, as shown in FIG. 7A, depression of mechanical deflation-control button 850 transitions mechanical inflation-control button 338 from its first spatial position to its deflation-inducing spatial position, thereby deflating the inflatable element, as shown in FIG. 8B. Typically, the healthcare worker can use the same single hand to depress mechanical deflation-control button 850 and advance the catheter down the ventilation tube; optionally, mechanical deflation-control button 850 is shaped and arranged like a gun trigger. As used in the present application, including in the claims, "deflate" means reduce a level of inflation of, and does not require completely uninflating inflatable element 588. Typically, inflatable element 588 is partially inflated when mechanical inflation-control button 338 is in its first spatial position (this is typically also the case in all of the configurations described herein, even though the drawings do not reflect this). This is typically the case because inflatable element 588 comprises a non-compliant material (if inflatable element 588 were instead to comprise a medical-grade elastic material such as elastic silicone, that fully deflates in its resting state, manufacturing would be more difficult, e.g., because it is difficult to adhere silicone to the PVC that the catheter typically comprises).

For some applications, mechanical inflation-control button 338 is in a resting state when in its first spatial position. Typically, mechanical deflation-control button 850 is released before mechanical inflation-control button 338 is transitioned from its first spatial position to its second spatial position.

For some applications, input module 156 comprises one or more springs 350 that are arranged to bias mechanical inflation-control button 338 from its second spatial position toward its first spatial position. For some applications, the one or more springs 350 are not arranged to bias mechanical inflation-control button 338 from its first spatial position toward its deflation-inducing spatial position.

For some applications, the deflation-inducing, the first, and the second spatial positions are deflation-inducing, first, and second radial positions, and mechanical inflation-control button 338 is configured to assume at least the deflation-inducing, the first, and the second radial positions.

For some applications, inflation chamber 335 comprises the rigid lateral chamber walls, as described hereinabove with reference to FIGS. 1A-D, while for other applications, inflation chamber 335 comprises elastic compartment 332, as described hereinabove with reference to FIGS. 1A-D and 3A-B.

Figure 7B:
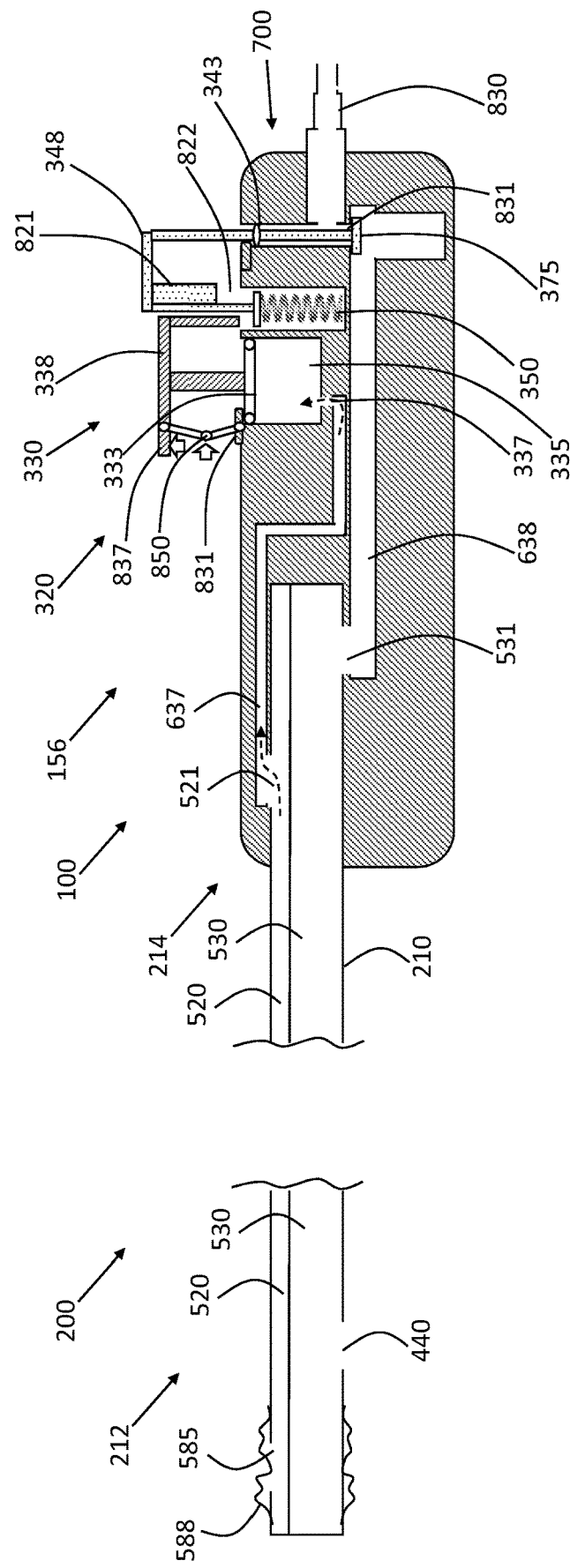
Figure 7C:
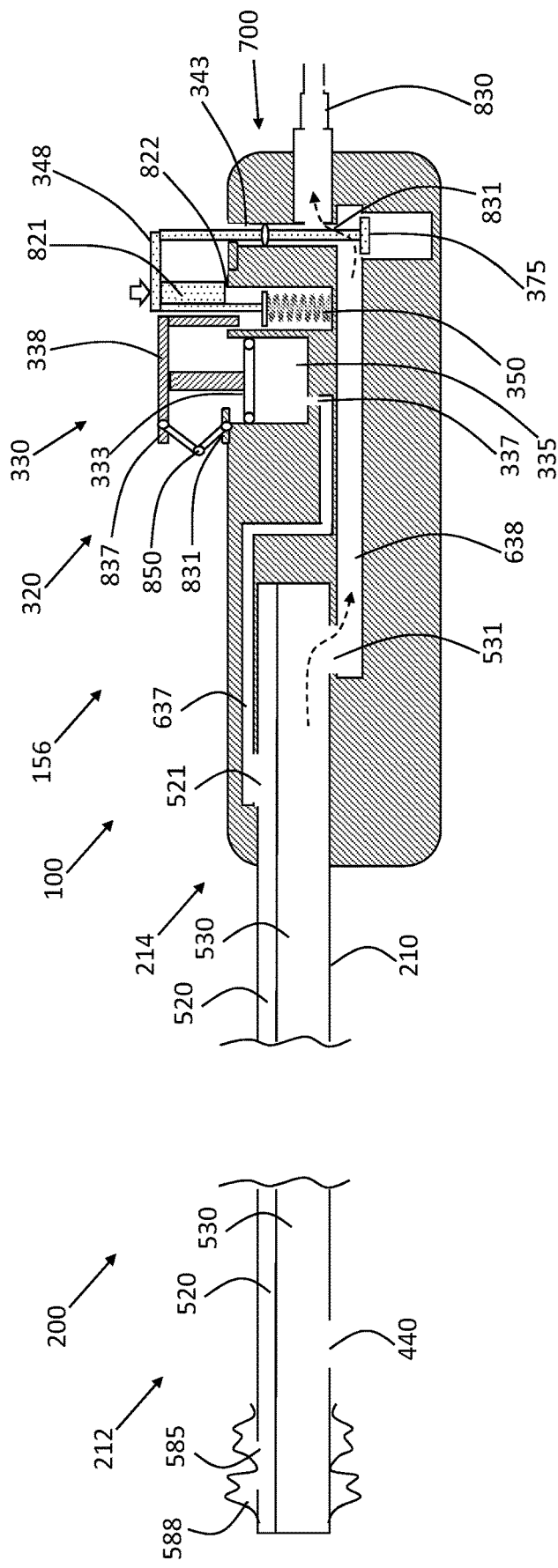

For suctioning the trachea, typically the following steps are performed:

depressing mechanical deflation-control button 850 to deflate inflatable element 588, as shown in FIG. 7B; it is desirable for inflatable element 588 to be as deflated as possible while it is advanced down the ventilation tube, in order to avoid the inflatable element pushing bacterial biofilm and mucous, which is on the wall of the ventilation tube, down the ventilation tube and into the trachea;

inserting cleaning catheter 200 into the ventilation tube in a proximal to distal direction while inflatable element 588 is essentially deflated, such in the state shown in FIG. 7B; typically, in order to perform "deep suction," the distal end of the cleaning catheter is advanced beyond the distal end of the ventilation tube; and applying suction to the trachea by transitioning input module 156 to the state shown in FIG. 7C.

Figure 7D:
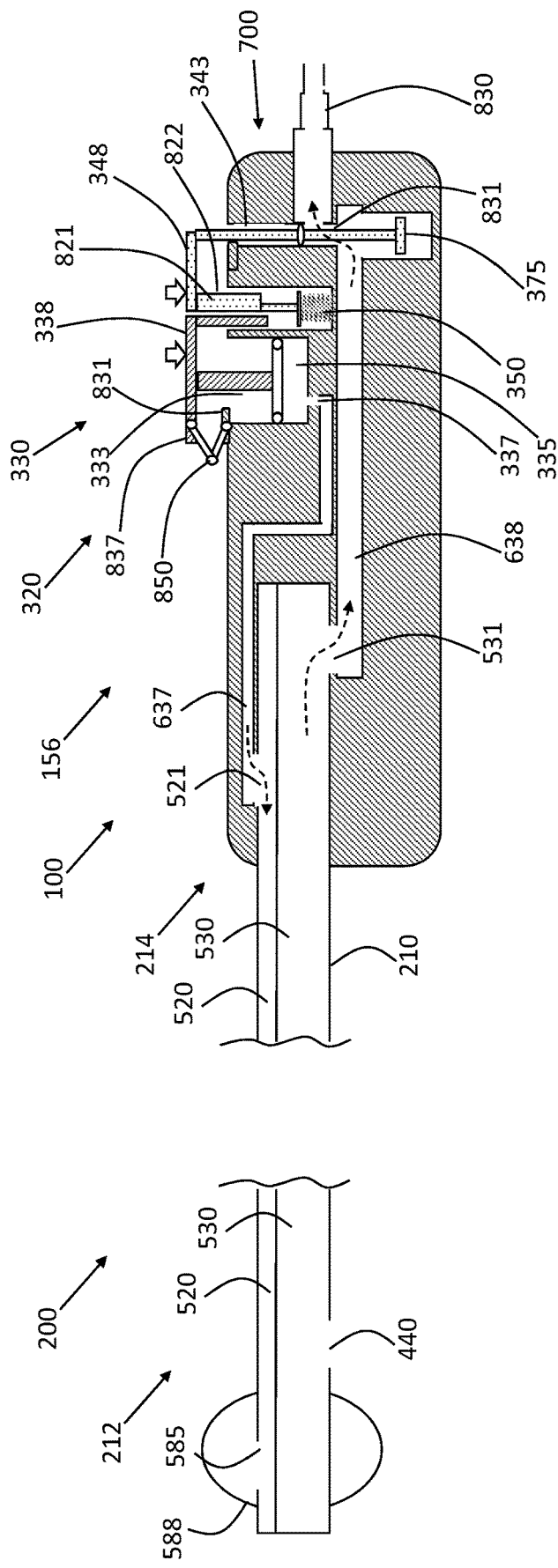

For cleaning a ventilation tube, the cleaning action typically comprises the following steps, which are typically performed in the following order:

depressing mechanical deflation-control button 850 to deflate inflatable element 588, as shown in FIG. 7B; it is desirable for inflatable element 588 to be as deflated as possible while it is advanced down the ventilation tube, in order to avoid the inflatable element pushing bacterial biofilm and mucous, which is on the wall of the ventilation tube, down the ventilation tube and into the trachea;

inserting cleaning catheter 200 into the ventilation tube in a proximal to distal direction while inflatable element 588 is essentially deflated, such in the state shown in FIG. 7B;

applying suction and inflating inflatable element 588 at a location near the distal end of the ventilation tube by transitioning input module 156 from the state shown in FIG. 7B directly (i.e., not via the state shown in FIG. 7C) to the state shown in FIG. 7D;

withdrawing the catheter along the ventilation tube in a distal to proximal direction while the inflatable element is inflated and suction is applied to the one or more suction orifices; and deflating the inflatable element when the inflatable element is near the proximal end of the ventilation tube or fully outside the proximal end of the ventilation tube, by transitioning input module 156 to the state shown in FIG. 7B.

In the description and claims of the present application, each of the verbs, "comprise," "include" and "have," and conjugates thereof, are used to indicate that the object or objects of the verb are not necessarily a complete listing of members, components, elements or parts of the subject or subjects of the verb. The articles "a" and "an" are used herein to refer to one or to more than one (i.e., to at least one) of the grammatical object of the article. By way of example, "an element" means one element or more than one element. The term "including" is used herein to mean, and is used interchangeably with, the phrase "including but not limited to." The term "or" is used herein to mean, and is used interchangeably with, the term "and/or," unless context clearly indicates otherwise. The term "such as" is used herein to mean, and is used interchangeably with, the phrase "such as but not limited to."

All publications, patent applications, patents, and other references mentioned herein are incorporated by reference in their entirety. In case of conflict, the present patent specification, including definitions, will prevail. In addition, the materials, methods, and examples are illustrative only and not intended to be limiting.

For brevity, some explicit combinations of various features are not explicitly illustrated in the figures and/or described. It is now disclosed that any combination of the method or device features disclosed herein can be combined in any manner—including any combination of features— any combination of features can be included in any embodiment and/or omitted from any embodiments.

The scope of the present invention includes embodiments described in the following applications, which are assigned to the assignee of the present application and are incorporated herein by reference. In an embodiment, techniques and apparatus described in one or more of the following applications are combined with techniques and apparatus described herein. It is noted that the phrase "fluid-control state" used herein may, for some applications, correspond in some respects to the phrases "mode," "activation mode," and/or "operating mode" referred to in the following applications (although many of the configurations of these states described herein differ in at least some respects from the configurations of the modes described in the following applications). It is also noted that the phrase "mechanical user control element" used herein may, for some applications, correspond in some respects to the word "switch," referred to in the following applications (although many of the configurations of these states described herein differ in at least some respects from the configurations of the modes described in the following applications):

PCT Publication WO/2012/131626 to Einav et al.

GB 2482618 A to Einav et al.;

UK Application GB 1119794.4, filed Nov. 16, 2011;

U.S. Provisional Application 61/468,990, filed Mar. 29, 2011;

U.S. Provisional Application 61/473,790, filed Apr. 10, 2011;

U.S. Provisional Application 61/483,699, filed May 8, 2011;

U.S. Provisional Application 61/496,019, filed Jun. 12, 2011;

U.S. Provisional Application 61/527,658, filed Aug. 26, 2011;

U.S. Provisional Application 61/539,998, filed Sep. 28, 2011;

U.S. Provisional Application 61/560,385, filed Nov. 16, 2011;

U.S. Provisional Application 61/603,340, filed Feb. 26, 2012;

U.S. Provisional Application 61/603,344, filed Feb. 26, 2012;

U.S. Provisional Application 61/609,763, filed Mar. 12, 2012;

U.S. Provisional Application 61/613,408, filed Mar. 20, 2012;

U.S. Provisional Application 61/635,360, filed Apr. 19, 2012;

U.S. Provisional Application 61/655,801, filed Jun. 5, 2012;

U.S. Provisional Application 61/660,832, filed Jun. 18, 2012;

U.S. Provisional Application 61/673,744, filed Jul. 20, 2012;

PCT Publication WO 2013/030821 to Zachar et al.;

U.S. Pat. No. 8,999,074 to Zachar et al;

UK Application 1600233.9, filed Jan. 6, 2016;

U.S. Provisional Application 62/287,223, filed Jan. 26, 2016;

U.S. Provisional Application 62/319,640, filed Apr. 7, 2016;

U.S. Provisional Application 62/336,894, filed May 16, 2016;

U.S. Provisional Application 62/336,753, filed May 16, 2016;

U.S. Provisional Application 62/376,102, filed Aug. 17, 2016;

U.S. application Ser. No. 15/363,782, filed Nov. 29, 2016; and

International Application PCT/IL2016/051367, filed Dec. 22, 2016.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for use with a tracheal ventilation tube and a suction source, the apparatus comprising:
   (A) a cleaning catheter, which is insertable into the ventilation tube and comprises:
      (i) an elongate, flexible, tubular catheter main body, which is shaped so as to define (a) one or more distal suction orifices, (b) a suction lumen, and (c) an inflation lumen; and
      (ii) an inflatable element, which is mounted to the catheter main body; and
   (B) an input module, which is coupled to the cleaning catheter, and comprises:
      (i) an inflation module, which comprises an inflation chamber, wherein the inflation lumen couples an interior of the inflation chamber in fluid communication with an interior of the inflatable element;
      (ii) a flow regulator, which is shaped so as to define a suction port coupleable in fluid communication with the suction source;
      (iii) a mechanical suction-control button, which is configured to assume at least first and second spatial positions;
      (iv) a mechanical inflation-control button, which is configured to (a) assume at least first and second spatial positions, and (b) mechanically and non-electrically increase pressure in the interior of the inflation chamber during a transition of the mechanical inflation-control button from its first spatial position to its second spatial position; and
      (v) a reversibly-engageable linking element, which is moveable with respect to the mechanical suction-control button and the mechanical inflation-control button, and is configured to assume at least (a) a first spatial position, in which the linking element does not engage the mechanical suction-control button when the mechanical suction-control button is in its second spatial position, and (b) a second spatial position,
   wherein the input module is arranged such that:
      at least when the mechanical suction-control button is in its first spatial position, the flow regulator blocks fluid communication between the suction source and the distal suction orifices, and at least when the mechanical suction-control button is in its second spatial position, the flow regulator connects the suction source and the distal suction orifices in fluid communication via the suction lumen, and
      when (a) the linking element is in its second spatial position and (b) the mechanical suction-control button and the mechanical inflation-control button are in their respective first spatial positions: depression of the linking element transitions both the mechanical suction-control button and the mechanical inflation-control button to their respective second spatial positions, such that the linking element engages both the mechanical suction-control button and the mechanical inflation-control button at least when the mechanical suction-control button is in its second spatial position.

2. The apparatus according to claim 1, wherein the first and the second spatial positions of the linking element are first and second axial positions, and wherein the linking element is configured to assume at least the first and the second axial positions.

3. The apparatus according to claim 1,
   wherein the first and the second spatial positions of the mechanical suction-control button are first and second radial positions, and wherein the mechanical suction-control button is configured to assume at least the first and the second radial positions, and
   wherein the first and the second spatial positions of the mechanical inflation-control button are first and second radial positions, and wherein the mechanical inflation-control button is configured to assume at least the first and the second radial positions.

4. The apparatus according to claim 1, wherein the linking element is moveably attached to the mechanical inflation-control button.

5. The apparatus according to claim 1, wherein the input module is arranged such that the linking element, when in its first spatial position, does not prevent user access to the mechanical suction-control button.

6. The apparatus according to claim 1, wherein the input module is arranged such that the linking element, when in its first spatial position, does not engage the mechanical suction-control button.

7. The apparatus according to claim 1, wherein the input module is arranged such that the linking element, when in its first spatial position, engages the mechanical inflation-control button.

8. The apparatus according to claim 1, wherein the input module is arranged such that the linking element, when in its first spatial position, is not arranged to transition the mechanical suction-control button all the way to its second spatial position.

9. The apparatus according to claim 1, wherein the input module is arranged such that when (a) the linking element is in its second spatial position and (b) the mechanical suction-control button and the mechanical inflation-control button are in their respective first spatial positions: the depression of the linking element simultaneously transitions both the mechanical suction-control button and the mechanical inflation-control button to their respective second spatial positions.

10. The apparatus according to claim 1, wherein the linking element is arranged to axially slide between its first and second spatial positions.

11. The apparatus according to claim 1, wherein the mechanical suction-control button is disposed proximally to the mechanical inflation-control button.

12. The apparatus according to claim 1, wherein the input module is arranged such that the linking element, when in its first spatial position, prevents the transition of the mechanical inflation-control button from its first spatial position to its second spatial position.

13. The apparatus according to claim 12, wherein the input module is arranged such that the linking element, when in its first spatial position, (a) locks the mechanical inflation-control button in the first spatial position of the mechanical inflation-control button, and (b) does not lock the mechanical suction-control button.

14. The apparatus according to claim 13, wherein the input module is arranged such that transitioning of the linking element from its first spatial position to its second spatial position simultaneously (a) unlocks the mechanical inflation-control button from its first spatial position, and (b) links the mechanical suction-control button with the mechanical inflation-control button.

15. The apparatus according to claim 1, wherein the mechanical suction-control button and the mechanical inflation-control button are biased toward their respective first spatial positions.

16. The apparatus according to claim 1,
wherein the inflation chamber comprises (a) rigid lateral chamber walls, and (b) a moveable rigid compression wall that forms an airtight seal with the rigid lateral chamber walls, and
wherein the input module is configured such that the transition of the mechanical inflation-control button from its first spatial position to its second spatial position moves the moveable rigid compression wall with respect to the rigid lateral chamber walls, thereby mechanically and non-electrically increasing the pressure in the interior of the inflation chamber.

17. The apparatus according to claim 1,
wherein the inflation chamber comprises an elastic compartment, and
wherein the input module is configured such that the transition of the mechanical inflation-control button from its first spatial position to its second spatial position compresses the elastic compartment, thereby mechanically and non-electrically increasing the pressure in an interior of the elastic compartment.

18. The apparatus according to claim 1, wherein the mechanical inflation-control button is configured to increase the pressure in the interior of the inflation chamber by mechanically and non-electrically compressing the inflation chamber during the at least a portion of the transition of the mechanical inflation-control button from its first spatial position to its second spatial position.

19. The apparatus according to claim 1,
wherein the mechanical suction-control button is shaped so as to define a suction-control user interface surface,
wherein the mechanical inflation-control button is not shaped so as to define a user interface surface,
wherein the linking element is shaped so as to define a linking user interface surface,
wherein the input module is arranged such that when (a) the linking element is in its first spatial position and (b) the mechanical suction-control button is in its first spatial position: (a) at least a portion of the suction-control user interface surface is visible from outside the input module, and (b) depression of the suction-control user interface surface transitions the mechanical suction-control button to its second spatial position, and
wherein the input module is arranged such that when (a) the linking element is in its second spatial position and (b) the mechanical suction-control button and the mechanical inflation-control button are in their respective first spatial positions: depression of the linking user interface surface transitions both the mechanical suction-control button and the mechanical inflation-control button to their respective second spatial positions.

20. The apparatus according to claim 19, wherein, when (a) the linking element is in its first spatial position and (b) the mechanical suction-control button is in its first spatial position: at least 1 cm2 of the suction-control user interface surface is visible from outside the input module.

21. The apparatus according to claim 19, wherein the input module is arranged such that the linking element, when in its second spatial position, blocks external access to the suction-control user interface surface.

22. The apparatus according to claim 1,
wherein the mechanical inflation-control button is configured to additionally (a) assume a deflation-inducing spatial position, wherein the first spatial position is between the deflation-inducing spatial position and the second spatial position, and (b) mechanically and non-electrically increase the pressure in the interior of the inflation chamber during transition of the mechanical inflation-control button from its deflation-inducing spatial position to its first spatial position, and
wherein the input module further comprises a mechanical deflation-control button, which is arranged such that when the mechanical inflation-control button is in its first spatial position, depression of the mechanical deflation-control button transitions the mechanical inflation-control button from its first spatial position to its deflation-inducing spatial position, thereby deflating the inflatable element.

23. A method for use with a tracheal ventilation tube and a suction source, the method comprising:
providing a cleaning catheter, which is insertable into the ventilation tube and comprises (i) an elongate, flexible, tubular catheter main body, which is shaped so as to define (a) one or more distal suction orifices, (b) a suction lumen, and (c) an inflation lumen; and (ii) an inflatable element, which is mounted to the catheter main body;
providing an input module, which is coupled to the cleaning catheter, and comprises (i) an inflation module, which comprises an inflation chamber, wherein the inflation lumen couples an interior of the inflation chamber in fluid communication with an interior of the inflatable element; (ii) a flow regulator, which is shaped so as to define a suction port coupleable in fluid communication with the suction source; (iii) a mechanical suction-control button, which is configured to assume at least first and second spatial positions; (iv) a mechanical inflation-control button, which is configured to (a) assume at least first and second spatial positions, and (b) mechanically and non-electrically increase pressure in the interior of the inflation chamber during a transition of the mechanical inflation-control button from its first spatial position to its second spatial position; and (v) a reversibly-engageable linking element, which is moveable with respect to the mechanical suction-control button and the mechanical inflation-control button, and is configured to assume at least (a) a first spatial position, in which the linking element does not engage the mechanical suction-control button when the mechanical suction-control button is in its second spatial position, and (b) a second spatial position, wherein the input module is arranged such that: (i) at least when the mechanical suction-control button is in its first spatial position, the flow regulator blocks fluid communication between the suction source and the distal suction orifices, and at least when the mechanical suction-control button is in its second spatial position, the flow regulator connects the suction source and the distal suction orifices in fluid communication via the suction lumen, and (ii) when (a) the linking element is in its second spatial position and (b) the mechanical suction-control button and the mechanical inflation-control button are in their respective first spatial positions: depression of the linking element transitions both the mechanical suction-control button and the mechanical inflation-control button to their respective second spatial positions, such that the linking element engages both the mechanical suction-control button and the mechanical inflation-control button at least when the mechanical suction-control button is in its second spatial position;
coupling the suction portion in fluid communication with the suction source; and inserting the cleaning catheter, in a proximal to distal direction, into the ventilation tube inserted in a trachea of a patient, and advancing the cleaning catheter until a distal end of the catheter main body is axially disposed in the ventilation tube at a location more distal than an axial mid-point of the ventilation tube.

* * * * *